United States Patent
Cooke et al.

(10) Patent No.: US 6,825,342 B1
(45) Date of Patent: Nov. 30, 2004

(54) PLANT STARCH COMPOSITION

(75) Inventors: David Cooke, Bedfordshire (GB); Martine Debet, Northampton (GB); Michael J. Gidley, Northamptonshire (GB); Stephen A. Jobling, Huntingdon (GB); Richard Safford, Bedfordshire (GB); Christopher M. Sidebottom, Bedfordshire (GB); Roger J. Westcott, Northamptonshire (GB)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 08/945,722

(22) PCT Filed: May 3, 1996

(86) PCT No.: PCT/GB96/01075
§ 371 (c)(1),
(2), (4) Date: Dec. 18, 1997

(87) PCT Pub. No.: WO96/34968
PCT Pub. Date: Nov. 7, 1996

(30) Foreign Application Priority Data

May 5, 1995 (GB) .............................................. 9509229
Apr. 10, 1996 (GB) .............................................. 9607409

(51) Int. Cl.[7] .......................... C08B 31/00; C08B 33/00; C08B 35/00; C07H 1/00
(52) U.S. Cl. ........................ 536/102; 536/124; 536/128
(58) Field of Search ................................ 536/102, 124, 536/128

(56) References Cited

U.S. PATENT DOCUMENTS

| | | | | |
|---|---|---|---|---|
| 3,887,752 A | * | 6/1975 | Elizer | ......................... 428/378 |
| 4,608,265 A | * | 8/1986 | Zwiercan et al. | ........... 426/582 |
| 5,344,663 A | * | 9/1994 | Jewell et al. | ............... 426/549 |

FOREIGN PATENT DOCUMENTS

| | | | |
|---|---|---|---|
| JP | 6261767 | 9/1994 | ............. A23L/1/10 |
| WO | WO 90/12084 | 10/1990 | ............. C12N/5/00 |
| WO | WO 92/11375 | 7/1992 | ............. C12N/15/56 |
| WO | WO 92/11382 | 7/1992 | ............. C12P/21/00 |
| WO | WO 92/14827 | 9/1992 | ............. C12N/15/82 |
| WO | WO 94/24292 | * 10/1994 | |
| WO | WO 95/07355 | 3/1995 | ............. C12N/15/54 |
| WO | WO 95/26407 | 10/1995 | ............. C12N/15/82 |
| WO | WO 96/08261 | 3/1996 | ............. A61K/35/66 |
| WO | WO 96/19581 | 6/1996 | ............. C12N/15/56 |
| WO | WO 96/27674 | 9/1996 | ............. C12N/15/82 |
| WO | WO 96/34968 | 11/1996 | ............. C12N/15/82 |
| WO | WO 97/20040 | 6/1997 | ............. C12N/9/10 |

OTHER PUBLICATIONS

Blennow & Johansson, 1997 Phytochem. 30, 437–444.

(List continued on next page.)

*Primary Examiner*—Everett White
(74) *Attorney, Agent, or Firm*—Karen G. Kaiser

(57) ABSTRACT

Disclosed is a nucleotide sequence encoding an effective portion of a class A starch branching enzyme (SBE) obtainable from potato plants, or a functional equivalent thereof, together with, inter alia, a corresponding polypeptide, a method of altering the characteristics of a plant, a plant having altered characteristics; and starch, particularly starch obtained from a potato plant, having novel properties.

23 Claims, 75 Drawing Sheets

OTHER PUBLICATIONS

Burton, et al., "Starch Branching Enzymes Belong to Distinct Enzyme Families are Differently Expressed during Pea Embryo Development" The Plant Journal, 7(1):3–15 (1995).

Database WPI Section Ch, Week 9442 Derwent Publications Ltd., GB; Class C06, AN 94-37418 (JP 6261767).

Khoshnoodi, et al., "Characterization of the 97 and 103 kDa forms of starch branching enzymes from potato tubers" Febs Letters 332:132–138.

Koβmann et al., 1991 Mol. Gen. Genet. 230, 39–44.

Krohn, et al., "Modification of starch structure in transgenic potato" Plant Physiology 105(1):37 (1994).

Larsson, et al., "Three isoforms of starch synthase and two isoforms of branching enzyme are present in potato tuber starch" Plant Science (Shannon) 117(1–2):9–16 (1996).

Matzke & Matzke 1995 Plant Physiol. 107, 679–685.

Mizuno, et al., "Alteration of the structural properties of starch components by the lack of an isoform of starch branching enzyme in rice seeds" J. Biol. Chem. 268(25):19084–91 (1993).

Muller–Rober & Koβmann 1994 Plant Cell and Environment 17, 601–613.

Sheehy et al. 1988 PNAS 85, 8805–8809.

Takaha, et al. J. Biol. Chem. 268(2):1391–1396 (1993).

Van der Krol et al., Mol. Gen. Genet. 220, 204–212.

van der Leij, et al., "Expression of the gene encoding granule bound starch synthase after introduction in an amylose–free and a widetype potato" Abstracts VIIth International Congress on Plant Tissue and Cell Culture, Amsterdam, Jun. 24–29, No. A5–28, pp. 177 (1990).

Visser, et al., "Inhibition of the expression of the gene for granule–bound starch synthase in potato antisense constructs" Mol. Gen. Genet. 225:289–296 (1991).

Willmitzer, et al., "Starch synthesis n transgentic plants" Plant Polymeric Carbohydrates, International Symposium held in Berlin, Jul. 1–3, 1993, pp. 33–39.

Koβmann et al., Macromol. Symp. 120, 29–38 (1997).

* cited by examiner

Fig. 4a SHEET 1

Fig. 4a SHEET 2

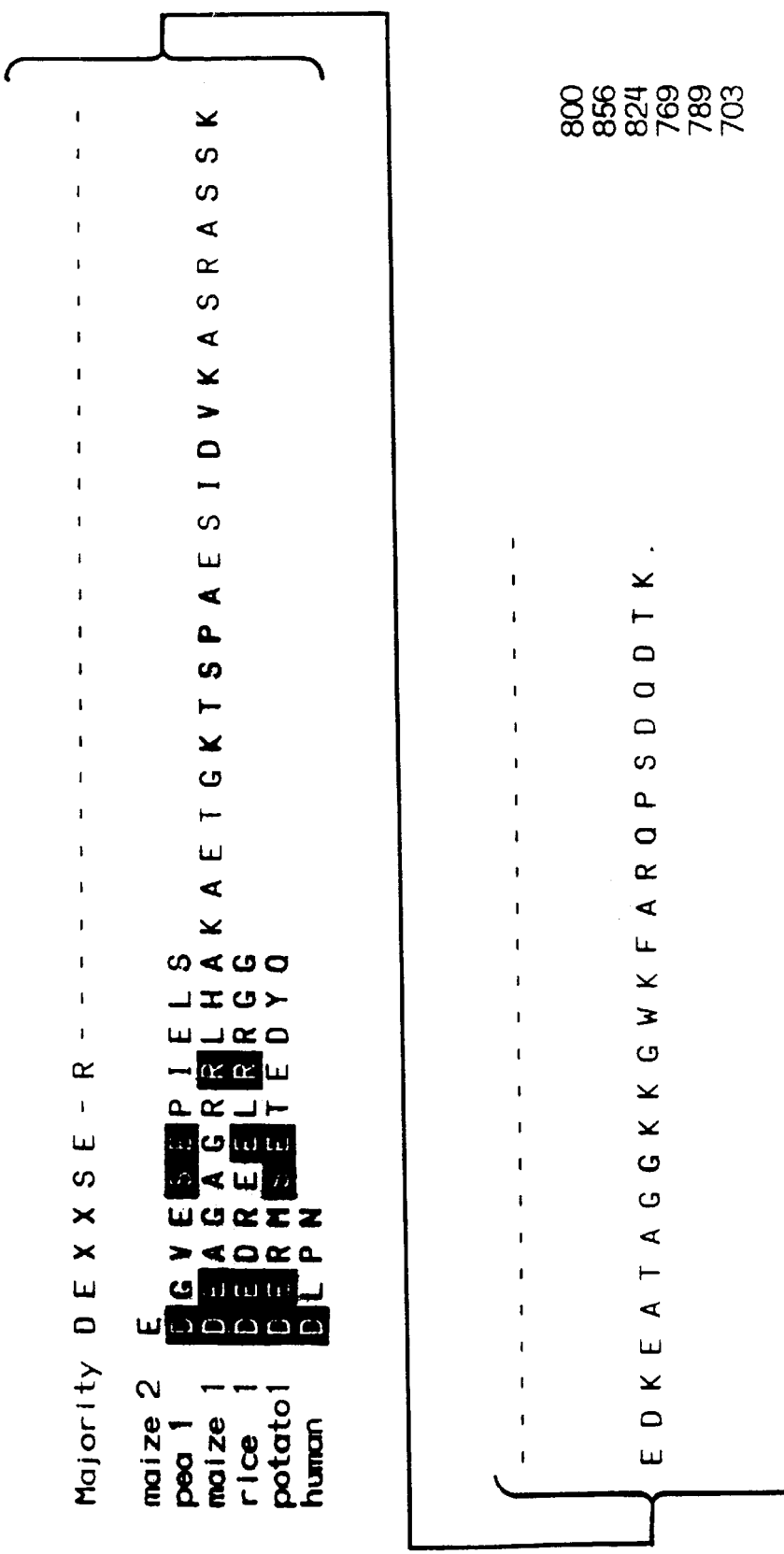
Fig. 4a SHEET 3

Fig. 4b

```
TTGATGGGGCCTTGAACTCAGCAATTTGACACTCAGTTAGTTACA
|---+----+----+----+----+----+----+----+----+----|
AACTACCCCGGAACTTGAGTCGTTAAACTGTGAGTCAATCAATGT

AAGGAATGAATAAAAGGATAGATTTGTAAAAACCCTAAGGAGAGA
|---+----+----+----+----+----+----+----+----+----|
TTCCTTACTTATTTTCCTATCTAAACATTTTGGGATTCCTCTCT
         M   N   K   R   I   D   L

GTTCCATCAGTGTACAAATCTAATGGATTCAGCAGTAATGGTGAT
|---+----+----+----+----+----+----+----+----+----|
CAAGGTAGTCACATGTTTAGATTACCTAAGTCGTCATTACCACTA
 V   P   S   V   Y   K   S   N   G   F   S   S   N   G   D

Bgl II                              EcoR I
TCACGGAAGATCTTGGCTGAAAAGTCTTCTTACAATTCCGAATTC
|---+----+----+----+----+----+----+----+----+----|
AGTGCCTTCTAGAACCGACTTTTCAGAAGAATGTTAAGGCTTAAG
 S   R   K   I   L   A   E   K   S   S   Y   N   S   E   F

ACCCAGAGTGATAGCTCCTCATCCTCAACAGACCAATTTGAGTTC
|---+----+----+----+----+----+----+----+----+----|
TGGGTCTCACTATCGAGGAGTAGGAGTTGTCTGGTTAAACTCAAG
 T   Q   S   D   S   S   S   S   S   T   D   Q   F   E   F

AGTTCAACAATGGAACACGCTAGCCAGATTAAAACTGAGAACGAT
|---+----+----+----+----+----+----+----+----+----|
TCAAGTTGTTACCTTGTGCGATCGGTCTAATTTTGACTCTTGCTA
 S   S   T   M   E   H   A   S   Q   I   K   T   E   N   D

GATTTTGCTTCATCACTACAACTACAAGAAGGTGGTAAACTGGAG
|---+----+----+----+----+----+----+----+----+----|
CTAAAACGAAGTAGTGATGTTGATGTTCTTCCACCATTTGACCTC
 D   F   A   S   S   L   Q   L   Q   E   G   G   K   L   E
```

Fig. 5 SHEET 1

BgI II

```
CTCCTATCACTTATCAGATCTCTATTTTTCTCTTAATTCCAACC
                                              90
GAGGATAGTGAATAGTCTAGAGATAAAAAGAGAATTAAGGTTGG

AGAAGAAAGATGGTGTATACACTCTCTGGAGTTCGTTTTCCTACT
                                              180
TCTTCTTTCTACCACATATGTGAGAGACCTCAAGCAAAAGGATGA
            M  V  Y  T  L  S  G  V  R  F  P  T

CGGAGGAATGCTAATGTTTCTGTATTCTTGAAAAAGCACTCTCTT
                                              270
GCCTCCTTACGATTACAAAGACATAAGAACTTTTTCGTGAGAGAA
 R  R  N  A  N  V  S  V  F  L  K  K  H  S  L

CGACCTTCTACAGTTGCAGCATCGGGGAAAGTCCTTGTGCCTGGA
                                              360
GCTGGAAGATGTCAACGTCGTAGCCCCTTTCAGGAACACGGACCT
 R  P  S  T  V  A  A  S  G  K  V  L  V  P  G

ACTGAGACATCTCCAGAAAATTCCCCAGCATCAACTGATGTAGAT
                                              450
TGACTCTGTAGAGGTCTTTTAAGGGGTCGTAGTTGACTACATCTA
 T  E  T  S  P  E  N  S  P  A  S  T  D  V  D

GACGTTGAGCCGTCAAGTGATCTTACAGGAAGTGTTGAAGAGCTG
                                              540
CTGCAACTCGGCAGTTCACTAGAATGTCCTTCACAACTTCTCGAC
 D  V  E  P  S  S  D  L  T  G  S  V  E  E  L

GAGTCTAAAACATTAAATACTTCTGAAGAGACAATTATTGATGAA
                                              630
CTCAGATTTTGTAATTTATGAAGACTTCTCTGTTAATAACTACTT
 E  S  K  T  L  N  T  S  E  E  T  I  I  D  E
```

Fig 5 SHEET 2

```
TCTGATAGGATCAGAGAGAGGGGCATCCCTCCACCTGGACTTGGT
AGACTATCCTAGTCTCTCTCCCCGTAGGGAGGTGGACCTGAACCA
 S   D   R   I   R   E   R   G   I   P   P   P   G   L   G

CACCTTGATTACAGGTATTCACAGTACAAGAAACTGAGGGAGGCA
GTGGAACTAATGTCCATAAGTGTCATGTTCTTTGACTCCCTCCGT
 H   L   D   Y   R   Y   S   Q   Y   K   K   L   R   E   A

GAAAAAATGGGTTTCACTCGTAGTGCTACAGGTATCACTTACCGT
CTTTTTTACCCAAAGTGAGCATCACGATGTCCATAGTGAATGGCA
 E   K   M   G   F   T   R   S   A   T   G   I   T   Y   R

AACAATTGGGACGCAAATGCTGACATTATGACTCGGAATGAATTT
TTGTTAACCCTGCGTTTACGACTGTAATACTGAGCCTTACTTAAA
 N   N   W   D   A   N   A   D   I   M   T   R   N   E   F

GCAATTCCTCATGGGTCCAGAGTGAAGATACGTATGGACACTCCA
CGTTAAGGAGTACCCAGGTCTCACTTCTATGCATACCTGTGAGGT
 A   I   P   H   G   S   R   V   K   I   R   M   D   T   P
```

Fig. 5 Sheet 4

Fig. 5 SHEET 3

```
                                                              Hinc II
CAGAAGATTTATGAAATAGACCCCCTTTTGACAAACTATCGTCAA
+----+----+----+----+----+----+----+----+----+ 720
GTCTTCTAAATACTTTATCTGGGGGAAAACTGTTTGATAGCAGTT
 Q  K  I  Y  E  I  D  P  L  L  T  N  Y  R  Q ATTGACAAGTATGAGGGTGGTTTGGAAGCCTTTTCTCGTGGTTAT
+----+----+----+----+----+----+----+----+----+ 810
TAACTGTTCATACTCCCACCAAACCTTCGGAAAAGAGCACCAATA
 I  D  K  Y  E  G  G  L  E  A  F  S  R  G  Y Pvu II
GAGTGGGCTCTTGGTGCCCAGTCAGCTGCCCTCATTGGAGATTTC
+----+----+----+----+----+----+----+----+----+ 900
CTCACCCGAGAACCACGGGTCAGTCGACGGGAGTAACCTCTAAAG
 E  W  A  L  G  A  Q  S  A  A  L  I  G  D  F GGTGTCTGGGAGATTTTTCTGCCAAATAATGTGGATGGTTCTCCT
+----+----+----+----+----+----+----+----+----+ 990
CCACAGACCCTCTAAAAAGACGGTTTATTACACCTACCAAGAGGA
 G  V  W  E  I  F  L  P  N  N  V  D  G  S  P TCAGGTGTTAAGGATTCCATTCCTGCTTGGATCAACTACTCTTTA
+----+----+----+----+----+----+----+----+----+ 1080
AGTCCACAATTCCTAAGGTAAGGACGAACCTAGTTGATGAGAAAT
 S  G  V  K  D  S  I  P  A  W  I  N  Y  S  L
```

Fig. 5 SHEET 4

```
CAGCTTCCTGATGAAATTCCATATAATGGAATACATTATGATCCA
GTCGAAGGACTACTTTAAGGTATATTACCTTATGTAATACTAGGT
 Q  L  P  D  E  I  P  Y  N  G  I  H  Y  D  P

CCAAAGTCGCTGAGAATATATGAATCTCATATTGGAATGAGTAGT
GGTTTCAGCGACTCTTATATACTTAGAGTATAACCTTACTCATCA
 P  K  S  L  R  I  Y  E  S  H  I  G  M  S  S

HinD III
CTTCCTCGCATAAAAAGCTTGGGTACAATGCGCTGCAAATTATG
GAAGGAGCGTATTTTTCGAACCCATGTTACGCGACGTTTAATAC
 L  P  R  I  K  K  L  G  Y  N  A  L  Q  I  M

ACAAATTTTTTTGCACCAAGCAGCCGTTTTGGAACGCCCGACGAC
TGTTTAAAAAAACGTGGTTCGTCGGCAAAACCTTGCGGGCTGCTG
 T  N  F  F  A  P  S  S  R  F  G  T  P  D  D

CTCATGGACATTGTTCACAGCCATGCATCAAATAATACTTTAGAT
GAGTACCTGTAACAAGTGTCGGTACGTAGTTTATTATGAAATCTA
 L  M  D  I  V  H  S  H  A  S  N  N  T  L  D
```

Fig. 5 Sheet 6

Fig. 5 SHEET 5

```
CCCGAAGAGGAGAGGTATATCTTCCAACACCCACGGCCAAAGAAA
|----|----|----|----|----|----|----|----|----| 1170
GGGCTTCTCCTCTCCATATAGAAGGTTGTGGGTGCCGGTTTCTTT
  P   E   E   E   R   Y   I   F   Q   H   P   R   P   K   K
```

Xmn I
```
CCGGAGCCTAAAATTAACTCATACGTGAATTTTAGAGATGAAGTT
|----|----|----|----|----|----|----|----|----| 1260
GGCCTCGGATTTTAATTGAGTATGCACTTAAAATCTCTACTTCAA
  P   E   P   K   I   N   S   Y   V   N   F   R   D   E   V

GCTATTCAAGAGCATTCTTATTACGCTAGTTTTGGTTATCATGTC
|----|----|----|----|----|----|----|----|----| 1350
CGATAAGTTCTCGTAAGAATAATGCGATCAAAACCAATAGTACAG
  A   I   Q   E   H   S   Y   Y   A   S   F   G   Y   H   V

CTTAAGTCTTTGATTGATAAAGCTCATGAGCTAGGAATTGTTGTT
|----|----|----|----|----|----|----|----|----| 1440
GAATTCAGAAACTAACTATTTCGAGTACTCGATCCTTAACAACAA
  L   K   S   L   I   D   K   A   H   E   L   G   I   V   V

GGACTGAACATGTTTGACTGCACCGATAGTTGTTACTTTCACTCT
|----|----|----|----|----|----|----|----|----| 1530
CCTGACTTGTACAAACTGACGTGGCTATCAACAATGAAAGTGAGA
  G   L   N   M   F   D   C   T   D   S   C   Y   F   H   S
```

Fig. 5 SHEET 6

Sac I

```
GGAGCTCGTGGTTATCATTGGATGTGGGATTCCCGCCTCTTTAAC
----+----+----+----+----+----+----+----+----+
CCTCGAGCACCAATAGTAACCTACACCCTAAGGGCGGAGAAATTG
 G   A   R   G   Y   H   W   M   W   D   S   R   L   F   N

TGGTGGTTGGATGCGTTCAAATTTGATGGATTTAGATTTGATGGT
----+----+----+----+----+----+----+----+----+
ACCACCAACCTACGCAAGTTTAAACTACCTAAATCTAAACTACCA
 W   W   L   D   A   F   K   F   D   G   F   R   F   D   G

ACTGGGAACTACGAGGAATACTTTGGACTCGCAACTGATGTGGAT
----+----+----+----+----+----+----+----+----+
TGACCCTTGATGCTCCTTATGAAACCTGAGCGTTGACTACACCTA
 T   G   N   Y   E   E   Y   F   G   L   A   T   D   V   D

TTCCCAGATGCAATTACCATTGGTGAAGATGTTAGCGGAATGCCG
----+----+----+----+----+----+----+----+----+
AAGGGTCTACGTTAATGGTAACCACTTCTACAATCGCCTTACGGC
 F   P   D   A   I   T   I   G   E   D   V   S   G   M   P

CGGCTGCATATGGCAATTGCTGATAAACGGATTGAGTTGCTCAAG
----+----+----+----+----+----+----+----+----+
GCCGACGTATACCGTTAACGACTATTTGCCTAACTCAACGAGTTC
 R   L   H   M   A   I   A   D   K   R   I   E   L   L   K

ACAAATAGAAGATGGTCGGAAAAGTGTGTTTCATACGCTGAAAGT
----+----+----+----+----+----+----+----+----+
TGTTTATCTTCTACCAGCCTTTTCACACAAAGTATGCGACTTTCA
 T   N   R   R   W   S   E   K   C   V   S   Y   A   E   S
```

Fig 5 Sheet 8

Fig. 5 SHEET 7

```
TATGGAAACTGGGAGGTACTTAGGTATCTTCTCTCAAATGCGAGA
----+----+----+----+----+----+----+----+----+ 1620
ATACCTTTGACCCTCCATGAATCCATAGAAGAGAGTTTACGCTCT
 Y  G  N  W  E  V  L  R  Y  L  L  S  N  A  R

GTGACATCAATGATGTATATTCACCACGGATTATCGGTGGGATTC
----+----+----+----+----+----+----+----+----+ 1710
CACTGTAGTTACTACATATAAGTGGTGCCTAATAGCCACCCTAAG
 V  T  S  M  M  Y  I  H  H  G  L  S  V  G  F
```

Hinc II

```
GCTGTTGTGTATCTGATGCTGGTCAACGATCTTATTCATGGGCTT
----+----+----+----+----+----+----+----+----+ 1800
CGACAACACATAGACTACGACCAGTTGCTAGAATAAGTACCCGAA
 A  V  V  Y  L  M  L  V  N  D  L  I  H  G  L

ACATTTTGTATTCCCGTCCAAGAGGGGGGTGTTGGCTTTGACTAT
----+----+----+----+----+----+----+----+----+ 1890
TGTAAAACATAAGGGCAGGTTCTCCCCCCACAACCGAAACTGATA
 T  F  C  I  P  V  Q  E  G  G  V  G  F  D  Y

AAACGGGATGAGGATTGGAGAGTGGGTGATATTGTTCATACACTG
----+----+----+----+----+----+----+----+----+ 1980
TTTGCCCTACTCCTAACCTCTCACCCACTATAACAAGTATGTGAC
 K  R  D  E  D  W  R  V  G  D  I  V  H  T  L

CATGATCAAGCTCTAGTCGGTGATAAAACTATAGCATTCTGGCTG
----+----+----+----+----+----+----+----+----+ 2070
GTACTAGTTCGAGATCAGCCACTATTTTGATATCGTAAGACCGAC
 H  D  Q  A  L  V  G  D  K  T  I  A  F  W  L
```

Fig. 5 SHEET 8

```
                                                              Hinc II
ATGGACAAGGATATGTATGATTTTATGGCTCTGGATAGACCGTCA
---+---------+---------+---------+---------+
TACCTGTTCCTATACATACTAAAATACCGAGACCTATCTGGCAGT
  M  D  K  D  M  Y  D  F  M  A  L  D  R  P  S Asp 718
                              Kpn I
CTTGTAACTATGGGATTAGGAGGAGAAGGGTACCTAAATTTCATG
---+---------+---------+---------+---------+
GAACATTGATACCCTAATCCTCCTCTTCCCATGGATTTAAAGTAC
  L  V  T  M  G  L  G  G  E  G  Y  L  N  F  M GAACAACACCTCTCTGATGGCTCAGTAATCCCCGGAAACCAATTC
---+---------+---------+---------+---------+
CTTGTTGTGGAGAGACTACCGAGTCATTAGGGGCCTTTGGTTAAG
  E  Q  H  L  S  D  G  S  V  I  P  G  N  Q  F Ssp I
TATTTAAGATACCGTGGGTTGCAAGAATTTGACCGGCCTATGCAG
---+---------+---------+---------+---------+
ATAAATTCTATGGCACCCAACGTTCTTAAACTGGCCGGATACGTC
  Y  L  R  Y  R  G  L  Q  E  F  D  R  P  M  Q ATATCACGAAAGGATGAAGGAGATAGGATGATTGTATTTGAAAAA
---+---------+---------+---------+---------+
TATAGTGCTTTCCTACTTCCTCTATCCTACTAACATAAACTTTTT
  I  S  R  K  D  E  G  D  R  M  I  V  F  E  K TCAGACTATCGCATAGCCTGCCTGAAGCCTGGAAAATACAAGGTT
---+---------+---------+---------+---------+
AGTCTGATAGCGTATCGGACGGACTTCGGACCTTTTATGTTCCAA
  S  D  Y  R  I  A  C  L  K  P  G  K  Y  K  V
```

Fig. 5 Sheet 10

Fig. 5 SHEET 9

```
ACATCATTAATAGATCGTGGGATAGCATTGCACAAGATGATTAGG
----+----+----+----+----+----+----+----+----+ 2160
TGTAGTAATTATCTAGCACCCTATCGTAACGTGTTCTACTAATCC
 T  S  L  I  D  R  G  I  A  L  H  K  M  I  R
```

```
         EcoR I
GGAAATGAATTCGGCCACCCTGAGTGGATTGATTTCCCTAGGGCT
----+----+----+----+----+----+----+----+----+ 2250
CCTTTACTTAAGCCGGTGGGACTCACCTAACTAAAGGGATCCCGA
 G  N  E  F  G  H  P  E  W  I  D  F  P  R  A
```

```
AGTTATGATAAATGCAGACGGAGATTTGACCTGGGAGATGCAGAA
----+----+----+----+----+----+----+----+----+ 2340
TCAATACTATTTACGTCTGCCTCTAAACTGGACCCTCTACGTCTT
 S  Y  D  K  C  R  R  R  F  D  L  G  D  A  E
```

```
TATCTTGAAGATAAATATGAGTTTATGACTTCAGAACACCAGTTC
----+----+----+----+----+----+----+----+----+ 2430
ATAGAACTTCTATTTATACTCAAATACTGAAGTCTTGTGGTCAAG
 Y  L  E  D  K  Y  E  F  M  T  S  E  H  Q  F
```

```
GGAAACCTAGTTTTTGTCTTTAATTTTCACTGGACAAAAAGCTAT
----+----+----+----+----+----+----+----+----+ 2520
CCTTTGGATCAAAAACAGAAATTAAAAGTGACCTGTTTTTCGATA
 G  N  L  V  F  V  F  N  F  H  W  T  K  S  Y
```

```
GCCTTGGACTCAGATGATCCACTTTTTGGTGGCTTCGGGAGAATT
----+----+----+----+----+----+----+----+----+ 2610
CGGAACCTGAGTCTACTAGGTGAAAAACCACCGAAGCCCTCTTAA
 A  L  D  S  D  D  P  L  F  G  G  F  G  R  I
```

Fig. 5 SHEET 10

```
                                    Ssp I
GATCATAATGCCGAATATTTCACCTTTGAAGGATGGTATGATGAT
CTAGTATTACGGCTTATAAAGTGGAAACTTCCTACCATACTACTA
 D   H   N   A   E   Y   F   T   F   E   G   W   Y   D   D

GTCTATGCACTAGTAGACAAAGAAGAAGAAGAAGAAGAAGAAGAA
CAGATACGTGATCATCTGTTTCTTCTTCTTCTTCTTCTTCTTCTT
 V   Y   A   L   V   D   K   E   E   E   E   E   E   E   E

TGAACGAACTTGTGATCGCGTTGAAAGATTTGAACGCTACATAGA
ACTTGCTTGAACACTAGCGCAACTTTCTAAACTTGCGATGTATCT

TCATGTGACACAAGGTTTGCAATTCTTTCCACTATTAGTAGTGCA
AGTACACTGTGTTCCAAACGTTAAGAAAGGTGATAATCATCACGT

EcoR I      Pst I
GATGAATTTATGTCGAATGCTGGGACGATCGAATTCCTGCAGGCC
CTACTTAAATACAGCTTACGACCCTGCTAGCTTAAGGACGTCCGG
```

Fig 5 Sheet 12

Fig. 5 SHEET 11

```
CGTCCTCGTTCAATTATGGTGTATGCACCTTGTAAAACAGCAGTG
                                                      2700
GCAGGAGCAAGTTAATACCACATACGTGGAACATTTGTCGTCAC
 R   P   R   S   I   M   V   Y   A   P   C   K   T   A   V

GAAGAAGAAGTAGCAGCAGTAGAAGAAGTAGTAGTAGAAGAAGAA
                                                      2790
CTTCTTCTTCATCGTCGTCATCTTCTTCATCATCATCTTCTTCTT
 E   E   E   V   A   A   V   E   E   V   V   V   E   E   E

Ssp I
GCTTCTTGACGTATCTGGCAATATTGCATCAGTCTTGGCGGAATT
                                                      2880
CGAAGAACTGCATAGACCGTTATAACGTAGTCAGAACCGCCTTAA

Cla I
ACGATATACGCAGAGATGAAGTGCTGAACAAACATATGTAAAATC
                                                      2970
TGCTATATGCGTCTCTACTTCACGACTTGTTTGTATACATTTTAG

GGGGGACCCCTTAGTTCT
                    3033
CCCCCTGGGGAATCAAGA
```

Fig. 5 SHEET 12

```
       ↓180         ↓190         ↓200         ↓210         ↓220
IYEIDPLLTNYRQHLDYRYSQYKKLREAIDKYEGGLEAFSRGYEKMGFTR
 : ::DP L. Y :H: .R .:Y . :   I:KYEG LE. F:: GY K. GF. R
LLNLDPTLEPYLDHFRHRMKRYVDQKMLIEKYEGPLEEFAQGYLKFGFNR
       ↑100         ↑110         ↑120         ↑130         ↑140
       ↓230         ↓240         ↓250         ↓260         ↓270
SATGITYREWALGAQSAALIGDFNNWDANADIMTRNEFGVWEIFLPNNVD
 ...  I. YREWA : AQ. A. : IGDFN. W: ::.:: M. ::: FGVW. I :P: VD
EDGCIVYREWAPAAQEAEVIGDFNGWNGSNHMMEKDQFGVWSIRIPD-VD
       ↑150         ↑160         ↑170         ↑180         ↑190
       ↓280         ↓290         ↓300         ↓310         ↓320
GSPAIPHGSRVKIRMDTPSGV-KDSIPAWINYSLQLPDEI--PYNGIHYD
 :. P. IPH. SRVK: R. .   :GV   D. IPAWI: Y: . :..:  PY: G: .. D
SKPVIPHNSRVKFRFKHGNGVWVDRIPAWIKYATADATKFAAPYDGVYWD
       ↑200         ↑210         ↑220         ↑230         ↑240
       ↓330         ↓340         ↓350         ↓360         ↓370
PPEEERYIFQHPRPKKPKSLRIYESHIGMSSPEPKINSYVNFRDEVLPRI
PP . ERY F:. PRP KP:: RIYE:H: GMSS: EP:: NSY : F D: VLPRI
PPPSERYHFKYPRPPKPRAPRIYEAHVGMSSSEPRVNSYREFADDVLPRI
       ↑250         ↑260         ↑270         ↑280         ↑290
       ↓380         ↓390         ↓400         ↓410         ↓420
KKLGYNALQIMAIQEHSYYASFGYHVTNFFAPSSRFGTPDDLKSLIDKAH
K . YN:: Q: MAI EHSYY: SFGYHVTNFFA S: R: G. P: DLK  LIDKAH
KANNYNTVQLMAIMEHSYYGSFGYHVTNFFAVSNRYGNPEDLKYLIDKAH
       ↑300         ↑310         ↑320         ↑330         ↑340
       ↓430         ↓440         ↓450         ↓460         ↓470
ELGIVVLMDIVHSHASNNTLDGLNMFDC---TDSCYFHSGARGYHWMWDS
 . LG:  VL: D: VHSHASNN. DGLN FD       ::.. YFH: G. RGYH : WDS
SLGLQVLVDVVHSHASNNVTDGLNGFDIGQGSQESYFHAGERGYHKLWDS
       ↑350         ↑360         ↑370         ↑380         ↑390
       ↓480         ↓490         ↓500         ↓510         ↓520
RLFNYGNWEVLRYLLSNARWWLDAFKFDGFRFDGVTSMMYIHHGLSVGFT
RLFNY: NWEVLR: LLSN RWWL: . :: FDGFRFDG: TSM: Y: HHG: ::: GFT
RLFNYANWEVLRFLLSNLRWWLEEYNFDGFRFDGITSMLYVHHGINMGFT
       ↑400         ↑410         ↑420         ↑430         ↑440
       ↓530         ↓540         ↓550         ↓560         ↓570
GNYEEYFGLATDVDAVVYLMLVNDLIHGLFPDAITIGEDVSGMPTFCIPV
GNY: EYF:  ATDVDAVVYLML. N: LIH : FPDA.. I: EDVSGMP. :.  PV
GNYNEYFSEATDVDAVVYLMLANNLIHKIFPDATVIAEDVSGMPGLSRPV
       ↑450         ↑460         ↑470         ↑480         ↑490
       ↓580         ↓590         ↓600         ↓610         ↓620
QEGGVGFDYRLHMAIADKRIELLK-KRDEDWRVGDIVHTLTNRRWSEKCV
 EGG: GFDYRL MAI: DK: I:  LK K. DEDW. :  ::. :LTNRR. : EKC:
SEGGIGFDYRLAMAIPDKWIDYLKNKNDEDWSMKEVTSSLTNRRYTEKCI
       ↑500         ↑510         ↑520         ↑530         ↑540
```

Fig. 6 SHEET 1

```
           ₸630       ₸640       ₸650       ₸660       ₸670
      SYAESHDQALVGDKTIAFWLMDKDMYDFMALDRPSTSLIDRGIALHKMIR
      :YAESHDQ::VGDKTIAF LMDK:MY. M:     :::::DRGIALHKMI:
      AYAESHDQSIVGDKTIAFLLMDKEMYSGMSCLTDASPVVDRGIALHKMIH
           ⊥550       ⊥560       ⊥570       ⊥580       ⊥590
           ₸680       ₸690       ₸700       ₸710       ₸720
      LVTMGLGGEGYLNFMGNEFGHPEWIDFPRAEQHLSDGSVIPGNQFSYDKC
      : TM: LGGEGYLNFMGNEFGHPEWIDFPR          GN:.SYDKC
      FFTMALGGEGYLNFMGNEFGHPEWIDFPR---------EGNNWSYDKC
           ⊥600       ⊥610       ⊥620                  ⊥630
           ₸730       ₸740       ₸750       ₸760       ₸770
      RRRFDLGDAEYLRYRGLQEFDRPMQYLEDKYEFMTSEHQFISRKDEGDRM
      RR:.: L: D: E. LRY:  ::. FDR: M:  L::K:. F:: S.. Q:: S.. D::::: 
      RRQWNLADSEHLRYKFMNAFDRAMNSLDEKFSFLASGKQIVSSMDDDNKV
           ⊥640       ⊥650       ⊥660       ⊥670       ⊥680
           ₸780       ₸790       ₸800       ₸810       ₸820
      IVFEKGNLVFVFNFHWTKSYSDYRIACLKPGKYKVALDSDDPLFGGFGRI
      : VFE: G: LVFVFNFH .::Y.: Y:::C  PGKY: VAL: SD.   FGG GR
      VVFERGDLVFVFNFHPNNTYEGYKVGCDLPGKYRVALGSDAWEFGGHGRA
           ⊥690       ⊥700       ⊥710       ⊥720       ⊥730
           ₸830             ₸840       ₸850       ₸860
      DHNAEYFT--------FEGWYDDRPRSIMVYAPCKTAVVYALVDKEEEEE
      : H:. :. FT             E.  :::RP. S:. V  : P :T V. Y    VD.     . E.
      GHDVDHFTSPEGIPGVPETNFNGRPNSFKVLSPARTCVAYYRVDERMSET
           ⊥740       ⊥750       ⊥760       ⊥770       ⊥780
           ₸870
      EEEEEEV
      E: :.::
      EDYQTDI
           ⊥790
```

Fig. 6 SHEET 2

```
        ↱10       ↱20       ↱30       ↱40
MVYTLSGVRFPTVPSVYKSNGFSSNGDRRNANVSVFLKKH--SLSRKILA
MVYT: SG: RFP. : PS: . KS   : .  DRR. : :  S FLK: :   S: SR.  L
MVYTISGIRFPVLPSLHKS---TLRCDRRASSHSFFLKNNSSSFSRTSLY
        ↰10       ↰20       ↰30       ↰40
   ↱50       ↱60       ↱70       ↱80       ↱90
EKSSYNSEFRPSTVAASGKVLVPGTQSDSSSSSTDQFEFTETSPENSPAS
. K S : SE : : ST: A. S: KVL: P. . Q  D: S S : DQ: E . : . : : E: : . .
AKFSRDSETKSSTIAESDKVLIPEDQ-DNSVSLADQLENPDITSEDAQNL
   ↰50       ↰60       ↰70       ↰80       ↰90
   ↱100      ↱110      ↱120      ↱130      ↱140
TDVDSSTMEHASQIKTENDDVEPSSDLTGSVEELDFASSLQLQEGGKLEE
. D:       TM. : : :   : . :   ,  : . . :   : .   : S : : : : : :  .
EDL---TMKDGNKYNID-ESTSSYREVGDEKGSVTSSSLVDVNTDTQ--A
      ↰100      ↰110      ↰120      ↰130        ↰140
   ↱150      ↱160      ↱170      ↱180      ↱190
SKTLNTSEETIIDESDRIRERGIPPPGLGQKIYEIDPLLTNYRQHLDYRY
. KT    S: . . :    : . .  : I       IPPPG GQKIYEIDPLL . . RQHLD: RY
KKTSVHSDKKVKVDKPKI----IPPPGSGQKIYEIDPLLQAHRQHLDFRY
        ↰150      ↰160      ↰170      ↰180
   ↱200      ↱210      ↱220      ↱230      ↱240
SQYKKLREAIDKYEGGLEAFSRGYEKMGFTRSATGITYREWALGAQSAAL
: QYK: : RE. IDKYEGGL: AFSRGYEK. GFTRSATGITYREW:  GA: SAAL
GQYKRIREEIDKYEGGLDAFSRGYEKFGFTRSATGITYREWGPGAKSAAL
       ↰190      ↰200      ↰210      ↰220      ↰230
   ↱250      ↱260      ↱270      ↱280      ↱290
IGDFNNWDANADIMTRNEFGVWEIFLPNNVDGSPAIPHGSRVKIRMDTPS
: GDFNNW: : NAD: MT: : . FGVWEIFLPNN. DGSP: IPHGSRVKI: MDTPS
VGDFNNWNPNADVMTKDAFGVWEIFLPNNADGSPPIPHGSRVKIHMDTPS
       ↰240      ↰250      ↰260      ↰270      ↰280
   ↱300      ↱310      ↱320      ↱330      ↱340
GVKDSIPAWINYSLQLPDEIPYNGIHYDPPEEERYIFQHPRPKKPKSLRI
G: KDSIPAWI: : S: Q  P: EIPYNGI. YDPPEEE: Y: F: HP: PK: P: S: RI
GIKDSIPAWIKFSVQAPGEIPYNGIYYDPPEEEKYVFKHPQPKRPQSIRI
       ↰290      ↰300      ↰310      ↰320      ↰330
   ↱350      ↱360      ↱370      ↱380      ↱390
YESHIGMSSPEPKINSYVNFRDEVLPRIKKLGYNALQIMAIQEHSYYASF
YESHIGMSSPEPKIN: Y. NFRD: VLPRIKKLGYNA: QIMAIQEHSYYASF
YESHIGMSSPEPKINTYANFRDDVLPRIKKLGYNAVQIMAIQEHSYYASF
       ↰340      ↰350      ↰360      ↰370      ↰380
   ↱400      ↱410      ↱420      ↱430      ↱440
GYHVTNFFAPSSRFGTPDDLKSLIDKAHELGIVVLMDIVHSHASNNTLDG
GYHVTNFFAPSSRFGTP: DLKSLID: AHELG: : VLMDIVHSH: SNNTLDG
GYHVTNFFAPSSRFGTPEDLKSLIDRAHELGLLVLMDIVHSHSSNNTLDG
       ↰390      ↰400      ↰410      ↰420      ↰430
```

Fig. 7 SHEET 1

```
       ↓450      ↓460      ↓470      ↓480      ↓490
LNMFDCTDSCYFHSGARGYHWMWDSRLFNYGNWEVLRYLLSNARWWLDAF
LNMFD TD:  YFH: G: RGYHWMWDSRLFNYG: WEVLRYLLSNARWWLD. :
LNMFDGTDGHYFHPGSRGYHWMWDSRLFNYGSWEVLRYLLSNARWWLDEY
       ↑440      ↑450      ↑460      ↑470      ↑480
       ↓500      ↓510      ↓520      ↓530      ↓540
KFDGFRFDGVTSMMYIHHGLSVGFTGNYEEYFGLATDVDAVVYLMLVNDL
KFDGFRFDGVTSMMY. HHGL V: FTGNY. EYFGLATDV: AVVY: MLVNDL
KFDGFRFDGVTSMMYTHHGLQVSFTGNYSEYFGLATDVEAVVYMMLVNDL
       ↑490      ↑500      ↑510      ↑520      ↑530
       ↓550      ↓560      ↓570      ↓580      ↓590
IHGLFPDAITIGEDVSGMPTFCIPVQEGGVGFDYRLHMAIADKRIELLKK
IHGLFP: A: : IGEDVSGMPTFC: P. Q: GG: GF: YRLHMA: ADK: IELLKK
IHGLFPEAVSIGEDVSGMPTFCLPTQDGGIGFNYRLHMAVADKWIELLKK
       ↑540      ↑550      ↑560      ↑570      ↑580
       ↓600      ↓610      ↓620      ↓630      ↓640
RDEDWRVGDIVHTLTNRRWSEKCVSYAESHDQALVGDKTIAFWLMDKDMY
: DEDWR: GDIVHTLTNRRW EKCV YAESHDQALVGDKT: AFWLMDKDMY
QDEDWRMGDIVHTLTNRRWLEKCVVYAESHDQALVGDKTLAFWLMDKDMY
       ↑590      ↑600      ↑610      ↑620      ↑630
       ↓650      ↓660      ↓670      ↓680      ↓690
DFMALDRPSTSLIDRGIALHKMIRLVTMGLGGEGYLNFMGNEFGHPEWID
DFMALDRPST: LIDRGIALHKMIRL: TMGLGGEGYLNFMGNEFGHPEWID
DFMALDRPSTPLIDRGIALHKMIRLITMGLGGEGYLNFMGNEFGHPEWID
       ↑640      ↑650      ↑660      ↑670      ↑680
       ↓700      ↓710      ↓720      ↓730      ↓740
FPRAEQHLSDGSVIPGNQFSYDKCRRRFDLGDAEYLRYRGLQEFDRPMQY
FPR: EQHL: : G. : : PGN: SYDKCRRRFDLGDA: YLRY: G: QEFDR: MQ.
FPRGEQHLPNGKIVPGNNNSYDKCRRRFDLGDADYLRYHGMQEFDRAMQH
       ↑690      ↑700      ↑710      ↑720      ↑730
       ↓750      ↓760      ↓770      ↓780      ↓790
LEDKYEFMTSEHQFISRKDEGDRMIVFEKGNLVFVFNFHWTKSYSDYRIA
LE: . Y. FMTSEHQ: ISRK: EGDR: I: FE: : NLVFVFNFHWT: SYSDY: : :
LEETYGFMTSEHQYISRKNEGDRVIIFERDNLVFVFNFHWTNSYSDYKVG
       ↑740      ↑750      ↑760      ↑770      ↑780
       ↓800      ↓810      ↓820      ↓830      ↓840
CLKPGKYKVALDSDDPLFGGFGRIDHNAEYFTFEGWYDDRPRSIMVYAPC
CLKPGKYK: . LDSDD. LFGGF. R: : H. AEYFT EGWYDDRPRS: : VYAP.
CLKPGKYKIVLDSDDTLFGGFNRLNHTAEYFTSEGWYDDRPRSFLVYAPS
       ↑790      ↑800      ↑810      ↑820      ↑830
       ↓850      ↓860      ↓870
KTAVVYALVDKEEEEEEEEEEEVAA
: TAVVYAL. D  E. E   E . : . V. :
RTAVVYALADGVESEPIELSDGVES
       ↑840      ↑850      ↑860
```

Fig. 7 SHEET 2

```
  1    -------------------TTG--AT-----------
  1    -------------------TTGA--------------
  1    ---------------------GA--------------
 45    AAAAACCTCCTCCACTCAGTCTTGGATCTCTCTCTCT

72    TTTCTCTTAATTCCAACCAGGCGAATGAATAAAAGGAT-A
 73    TTTCTCTTAATTCCAACCAAGG-AATGAATAAAAGGAT-A
 71    TTTCTCTTAATTCCAACCAAGG-AATGAATAAAAGAT-A
165    TTTCTCTTAATTCCAACCAAGG-AATGAATAAAAGATTA

191    TGTACAAATCTAATGGATTCAGCAGTAATGGTGATCGGAG
191    TGTACAAATCTAATGGATTCAGCAGTAATGGTGATCGGAG
189    TGTACAAATCTAATGGATTCAGCAGTAATGGTGATCGGAG
274    TGTACAAATCTAATGGATTCAGCAGTAATGGTGATCGGAG

311    AATTCCGACCTTCTACAGTTGCAGCATCGGGGAAAGTCCT
311    AATTCCGACCTTCTACAGTTGCAGCATCGGGGAAAGTCCT
309    AATCCCGACCTTCTACAATTGCAGCATCGGGGAAAGTCCT
394    AATCCCGACCTTCTACAGTTGCAGCATCGGGGAAAGTCCT

431    CAGCATCAACTGATGTAGATAGTTCAACAATGGAACACGC
431    CAGCATCAACTGATGTAGATAGTTCAACAATGGAACACGC
429    CAGCATCAACTGATGTAGATAGTTCAACAATGGAACACGC
514    CAGCATCAACTGATGTCGATAGTTCAACAATGGAACACGC

551    CATCACTACAACTACAAGAAGGTGGTAAACTGGAGGAGTC
551    CATCACTACAACTACAAGAAGGTGGTAAACTGGAGGAGTC
549    CATCACTACAACTACAAGAAGGTGGTAAACTGGAGGAGTC
634    CATCACTACAACTACAAGAAGGTGGTAAACTGGAGGAGTC

671    TTGGTCAGAAGATTTATGAAATAGACCCCCTTTTGACAAA
671    TTGGTCAGAAGATTTATGAAATAGACCCCCTTTTGACAAA
669    TTGGTCAGAAGATTTATGAAATAGACCCCCTTTTGACAAA
754    TTGGTCAGAAGATTTATGAAATAGACCCCCTTTTGACAAA

791    AAGC-TTTTCTCGTGGTTATGAAAAAATGGGTTTCACTCG
791    AAGCCTTTTCTCGTGGTTATGAAAAAATGGGTTTCACTCG
789    AAGCTTTTTCTCGTGGTTATGAAACAATGGGTTTCACTCG
874    AAGCTTTTTCTCGTGGTTATGAAAAAATGGGTTTCACTCG
```

Fig. 8 SHEET 1

Fig. 8 Sheet 2

```
-----------──GGGCCTTGAACTCAGCAATTTGACACTCAGTTAGTTAC
--------------TGGGGCCTTGAACTCAGCAATTTGACACTCAGTTAGTTAC
--------------TGGGGCCTTGAACTCAGCAATTTGACACTCAGTTAGTTAC
TCACGCTTCTCTTGGGGCCTTGAACTCAGCAATTTGACACTCAGTTAGTTAC

GATTTGTAAAAACCCTAAGGAGAGAAGAAGAAAGATGGTGTATATACTCTCT
GATTTGTAAAAACCCTAAGGAGAGAAGAAGAAAGATGGTGTATACACTCTCT
GATTTGTAAAAACCCTAAGGAGAGAAGAAGAAAGATGGTGTATACACTCTCT
GATTTG──────────AAGGAGAGAAGAAGAAAGATGGTGTATACACTCTCT

GAATGCTAATGTTTCTGTATTCTTGAAAAAGCACTCTCTTTCACGGAAGATC
GAATGCTAATGTTTCTGTATTCTTGAAAAAGCACTCTCTTTCACGGAAGATC
GAATGCTAATATTTCTGTATTCTTGAAAAACACTCTCTTTCACGGAAGATC
GAATGCTAATGTTTCTGTATTCTTGAAAAAGCACTCTCTTTCACGGAAGATC

TGTGCCTGGAACCCAGAGTGATAGCTCCTCATCCTAACAGACCAATTTGAG
TGTGCCTGGAACCCAGAGTGATAGCTCCTCATCCTAACAGACCAATTTGAG
TGTGCCTGGAATCCAGAGTGATAGCTCCTCATCCTAACAGATCAATTTGAG
TGTACCTGGAATCCAGAGTGATAGCTCCTCATCCTAACAGACCAATTTGAG

TAGCCAGATTAAAACTGAGAACGATGACGTTGAGCCGTCAAGTGATCTTACA
TAGCCAGATTAAAACTGAGAACGATGACGTTGAGCCGTCAAGTGATCTTACA
TAGCCAGATTAAAACTGAGAACGATGACGTTGAGCCGTCAAGTGATCTTACA
TAGCCAGATTAAAACTGAGAACGATGACGTTGAGCCGTCAAGTGATCTTACA

TAAAACATTAAATACTTCTGAAGAGACAATTATTGATGAATCTGATAGGATC
TAAAACATTAAATACTTCTGAAGAGACAATTATTGATGAATCTGATAGGATC
TAAAACATTAAATACTTCTGAAGAGACAATTATTGATGAATCTGATAGGATC
TAAAACATTAAATACTTCTGAAGAGACAATTATTGATGAATCTGATAGGATC

CTATCGTCAACACCTTGATTACAGGTATTCACAGTACAAGAAACTGAGGGAG
CTATCGTCAACACCTTGATTACAGGTATTCACAGTACAAGAAACTGAGGGAG
CTATCGTCAACACCTTGATTACAGGTATTCACAGTACAAGAAACTGAGGGAG
CTATCGTCAACACCTTGATTACAGGTATTCACAGTACAAGAAATGAGGGAG

TAGTGCTACAGGTATCACTTACCGTGAGTGGGCTCCTGGTGCCCAGTCAGCT
TAGTGCTACAGGTATCACTTACCGTGAGTGGGCTTTGGTGCCCAGTCAGCT
TAGTGCTACAGGTATCACTTACCGTGAGTGGGCTCCTGGTGCCCAGTCAGCT
TAGTGCTACAGGTATCACTTACCGTGAGTGGGCTCCTGGTGCCCAGTCAGCT
```

Fig. 8 Sheet 3

Fig. 8 SHEET 2

```
ACTCCTATCACTTATCAGATCTCTATTT  11con.seq
ACTCCTATCACTTATCAGATCTCTATTT  19con.seq
ACTGCCATCACTTATCAGATCTCTATTT  10con.seq
ACTCCTATCACTCATCAGATCTCTATTT  psbe2con.seq GGAGTTCGTTTTCCTACTGTTCCATCAG  11con.seq
GGAGTTCGTTTTCCTACTGTTCCATCAG  19con.seq
GGAGTTCGTTTTCCTACTGTTCCATCAG  10con.seq
GGAGTTCGTTTTCCTACTGTTCCATCAG  psbe2con.seq TTGGCTGAAAAGTCTTCTTACAATTCCG  11con.seq
TTGGCTGAAAAGTCTTCTTACAATTCCG  19con.seq
TTGGCTGAAAAGTCTTCTTACAATTCCG  10con.seq
TTGGCTGAAAAGTCTTCTTACCATTCCG  psbe2con.seq TTCACTGAGACATCTCCAGAAAATTCCC  11con.seq
TTCACTGAGACATCTCCAGAAAATTCCC  19con.seq
TTCGCTGAGACATCTCCAGAAAATTCCC  10con.seq
TTCACTGAGACAGCTCCAGAAAATTCCC  psbe2con.seq GGAAGTGTTGAAGAGCTGGATTTTGCTT  11con.seq
GGAAGTGTTGAAGAGCTGGATTTTGCTT  19con.seq
GGAAGTGTTGAAGAGCTGGATTTTGCTT  10con.seq
GGAAGTGTTGAAGATTGGATTTTGCTT   psbe2con.seq AGAGAGAGGGGCATCCCTCCACCTGGAC  11con.seq
AGAGAGAGGGGCATCCCTCCACCTGGAC  19con.seq
AGAGAGAGGGGCATCCCTCCACCTGGAC  10con.seq
AGAGAGAGGGGCATCCCTCCACCTGGAC  psbe2con.seq GCAATTGACAAGTATGAGGGTGGTTTGG  11con.seq
GCAATTGACAAGTATGAGGGTGGTTTGG  19con.seq
GCAATTGACAAGTATGAGGGTGGTTTGG  10con.seq
GCAATTGACAAGTATGAGGGTGGTTTGG  psbe2con.seq GCCCTCATTGGAGATTTCAACAATTGGG  11con.seq
GCCCTCATTGGAGATTTCAACAATTGGG  19con.seq
GCCCTCATTGCCGATTTCAACAATTGGG  10con.seq
GCTCTCATTGGAGATTTCAACAATTGGG  psbe2con.seq
```

Fig. 8
SHEET 3

```
910   ACGCAAATGCTGACATTATGACTCGGAATGAATTTGGTGTC
911   ACGCAAATGCTGACATTATGACTCGGAATGAATTTGGTGTC
909   ACGCAAATGCTGACTTTATGACTCGGAATGAATTTGGTGTC
994   ACGCAAATGCTGACATTATGACTCGGAATGAATTTGGTGTC

1030  CTCCATCAGGTGTTAAGGATTCCATTCCTGCTTGGATCAAC
1031  CTCCATCAGGTGTTAAGGATTCCATTCCTGCTTGGATCAAC
1029  CTCCATCAGGTGTTAAGGATTCCATTCCTGCTTGGATCAAC
1114  CTTCATCAGGTGTTAAGGATTCCATTCCTGCTTGGATCAAC

1150  AACACCCACGGCCAAAGAAACCAAAGTCGCTGAGAATATAT
1151  AACACCCACGGCCAAAGAAACCAAAGTCGCTGAGAATATAT
1149  AACACCCACGGCCAAAGAAACCAAAGTCGGTGAGAATATAT
1234  AACACCCACGGCCAAAGAAACCAAAGTCGCTGAGAATATAT

1270  TAAAAAA-GCTTGGGTACAATGCGCTGCCAATTATGGCTAT
1271  TAAAAAA-GCTTGGGTACAATGCGCTGCAAATTATGGCTAT
1269  TAAAAAAAGCTTGGGTACAATGCGGTGCAAATTATGGCTAT
1354  TAAAAAAC-CTTGGGTACAATGCGGTGCAAATTATGGCTAT

1389  GACGACCTTAAGTCTTCGATTGATAAAGCTCATGAGCTAGG
1390  GACGACCTTAAGTCTTTGATTGATAAAGCTCATGAGCTAGG
1389  GACGACCTTAAGTCTTTGATTGATAAAGCTCATGAGCTAGG
1473  GACGACCTTAAGTCTTTGATTGATAAAGCTCATGAGCTAGG

1509  GATAGTTGTTACTTTCACTCTGGAGCTCGTGGTTATCATTG
1510  GATAGTTGTTACTTTCACTCTGGAGCTCGTGGTTATCATTG
1509  GATAGTTGTTACTTTCACTCTGGAGCTCGTGGTTATCATTG
1593  GATAGTTGTTACTTTCACTCTGGAGCTCGTGGTTATCATTG

1628  GATGAGTTCAAATTTGATGGATTTAGATTCGATGGTGTGAC
1630  GATGCGTTCAAATTTGATGGATTTAGATTTGATGGTGTGAC
1629  GATGAGTTCAAATTTGATGGATTTAGATTTGATGGTGTGAC
1713  GATGAGTGCAAATTTGRTGGATTTAGATTTGATGGTGTGAC

1748  GTGGATGCTGTTGTGTATCTGATGCTGGTCAACGATCTTAT
1750  GTGGATGCTGTTGTGTATCTGATGCTGGTCAACGATCTTAT
1749  GTGGATGCTGTTGTGTATCTGATGCTGGTCAACGATCTTAT
1833  GTRGATGCTGCCGTGTATCTGATGCTGGCCAACGATCTTAT
```

Fig. 8
Sheet 5

Fig. 8
SHEET 4

```
TGGGAGATTTTTCTGCCAAATAATGTGGATGGTTCTCCTGCAATTC
TGGGAGATTTTTCTGCCAAATAATGTGGATGGTTCTCCTGCAATTC
TCAGAGATTTTTCTGCCAAATAATGTGGATGGTTCTCCTGCAATTC
TGGGAGATTTTTCTGCCAAATAATGTGGATGGTTCTCCTGCAATTC

TACTCTTTACAGCTTCCTGATGAAATTCCATATAATGGAATATATT
TACTCTTTACAGCTTCCTGATGAAATTCCATATAATGGAATACATT
TACTCTTTACAGCTTCCTGATGAAATTCCATATAATGGAATATATT
TACTCTTTACAGCTTCCTGATGAAATTCCATATAATGGAATATATT

GAATCTCATATTGGAATGAGTAGTCCGGAGCCTAAAATTAACTCAT
GAATCTCATATTGGAATGAGTAGTCCGGAGCCTAAAATTAACTCAT
GAATCTCATATTGGAATGAGTAGTCCGGAGCCTAAAATTAACTCAT
GAATCTCATATTGGAATGAGTAGTCCGGAGCCTAAAATTAACTCAT

TCAAGAGCATTCTTATTATGCTAGTTTTGGTTATCATGTCACAAAT
TCAAGAGCATTCTTATTACGCTAGTTTTGGTTATCATGTCACAAAT
TCAAGAGCATTCTTATTATGCTAGTTTTGGTTATCATGTCACAAAT
TCAAGAGCATTCTTATTATGCTAGTTTTGGTTATCATGTCACAAAT

AATTGTTGTTCTCATGGACATCGTTCACAGCCATGCATCAAATAAT
AATTGTTGTTCTCATGGACATTGTTCACAGCCATGCATCAAATAAT
AATTGTTGTTCTCATGGACATTGTTCACAGCCATGCATCAAATAAT
AATTGTTGTTCTCATGGACATTGTTCACAGCCATGCATCAAATAAT

GATGTGGGATTECCGCCTCTTTAACTATGGAAACTGGGAGGTACTT
GATGTGGGATTCCCGCCTCTTTAACTATGGAAACTGGGAGGTACTT
GATGTGGGATTTCCGCCTCTTTAACTATGGAAACTGGGAGGTACTT
GATGTGGGATTCCCGCCTCTTTAACTATGGAAACTGGGAGGTACTT

ATCAATGATGTATACTCACCACGGATTATCGGTGGGATTCACTGGG
ATCAATGATGTATATTCACCACGGATTATCGGTGGGATTCACTGGG
ATCAATGATGTGTACTCACCACGGATTATCGGTGGGATTCACTGGG
ATCAATGATGTATACTCACCACGGATTATCGGTGGGATTCACTGGG

TCATAGGCTTTTCCCAGATGCAATTACCATTGGTGAAGATGTTAGC
TCATGGGCTTTTCCCAGATGCAATTACCATTGGTGAAGATGTTAGC
TCATGGGCTTTTCCCAGATGCAATTACCATTGGTGAAGATGTTAGC
TCATGGGCTTTTCCCAGATGCAATTACCATTGGTGAAGATGTTAGC
```

Fig. 8 Sheet 6

Fig. 8 SHEET 5

```
CTCATGGGTCCAGAGTGAAGATACGTATGGACA  11con.seq
CTCATGGGTCCAGAGTGAAGATACGTATGGACA  19con.seq
CTCATGGGTCCAGAGTGAAGATACGTATGGACA  10con.seq
CTCATGGGTCCAGAGTGAAGATACGCATGGACA  psbe2con.seq ATGATCCACCCGAAGAGGAGAGGTATATCTTCC  11con.seq
ATGATCCACCCGAAGAGGAGAGGTATATCTTCC  19con.seq
ATGATCCACCCGAAGAGGAGAGGTATATCTTCC  10con.seq
ATGATCCACCCGAAGAGGAGAGGTATCTCTTCC  psbe2con.seq ACGTGAATTTTAGAGATGAAGTTCTTCCTCGCA  11con.seq
ACGTGAATTTTAGAGATGAAGTTCTTCCTCGCA  19con.seq
ACGTGAATTTTAGAGATGAAGTTCTTCCTCGCA  10con.seq
ACGTGAATTTTAGAGATGAAGTTCTTCCTCGCA  psbe2con.seq TTTTTTGCACCAAGCAGCCGTTTTGGAACGCCC  11con.seq
TTTTTTGCACCAAGCAGCCGTTTTGGAACGCCC  19con.seq
TTTTTTGCACCAAGCAGCCGTTTTGGAACGCCC  10con.seq
TTTTTTGCACCAAGCAGCCGTTTTGGAACGCCC  psbe2con.seq ACTTTAGATGGACTGAACATGTTTGACGGCACC  11con.seq
ACTTTAGATGGACTGAACATGTTTGACTGCACC  19con.seq
ACTTTAGATGGACTGAACATGTTTGACGGCACA  10con.seq
ACTTTAGATGGACTGAACATGTTTGACGGCACA  psbe2con.seq AGGTATCTTCTCTCAAATGCGAGATGGTGGTTG  11con.seq
AGGTATCTTCTCTCAAATGCGAGATGGTGGTTG  19con.seq
AGGTATCTTCTCTCAAATGCGAGATGGTGGTTG  10con.seq
AGGTATCTTCTCTCAAATGCGAGATGGTGGTTG  psbe2con.seq AACTACGAGGAATACTTTGGACTCGCAACTGAT  11con.seq
AACTACGAGGAATACTTTGGACTCGCAACTGAT  19con.seq
AACTACGAGGAATACTTTGGACTCGCAACTGAT  10con.seq
AACTACGAGGAATACTTTGGACTCGCAACTGAT  psbe2con.seq GGAATGCCGACATTTTGTATTCCCGTTCAAGAT  11con.seq
GGAATGCCGACATTTTGTATTCCCGTCCAAGAG  19con.seq
GGAATGCCGACATTTTGTGTTCCCGTTCAAGAT  10con.seq
GGAATGCCGACATTTTGTATTCCCGTTCAAGAT  psbe2con.seq
```

Fig. 8

```
1868  GGGGGTGTTGGCTTTGACTATCGGCTGCATATGGCAATTGC
1870  GGGGGTGTTGGCTTTGACTATCGGCTGCATATGGCAATTGC
1869  GGGGGTGTTGGCTTTGACTATCGGCTGCATATGGCAATTGC
1953  GGGGGTGTTGGCTTTGACTATCGGCTGCATATGGCAATTGC

1988  AGATGGTCGGAAAAGTGTGTTTCATACGCTGAAAGTCATGA
1990  AGATGGTCGGAAAAGTGTGTTTCATACGCTGAAAGTCATGA
1989  AGATGGTCGGAAAAGTGTGTTTCATACGCTGAAAGTCATGA
2073  AGATGGTCGGAAAAGTGTGTTTCATACGCTGAAAGTCATGA

2108  CCGCCAACATCATTAATAGATCGTGGGATAGCATTGCACAA
2110  CCGTCAACATCATTAATAGATCGTGGGATAGCATTGCACAA
2109  CCGTCAACATCATTAATAGATCGTGGGATAGCATTACACAA
2193  CCGTCAACATCATTAATAGATCGTGGGATAGCATTGCACAA

2228  TGGATTGATTTCCCTAGGGCTGACCACACCTTTCTGATGG
2230  TGGATTGATTTCCCTAGGGCTGAACAACACCTCTCTGATGG
2229  TGGATTGATTTCCCTAGGGCTGAACAACACCTCTCTGATGG
2313  TGGATTGATTTCCCTAGGGCTGAACAACACCTCTCTGATGG

2348  TACCATGGGTTACAAGAATTTGACTGGGCTATGCAGTATCT
2350  TACCGTGGGTTGCAAGAATTTGACCGCCTATGCAGTATCT
2349  TACCGTGGGTTGCAAGAATTTGACCGGGCTATGCAGTATCT
2433  TACCGTGGGTTGCAAGAATTTGACCGGGCTATGCAGTATCT

2468  GAAAGAGGAAACCTAGTTTTCGTCTTTAATTTTCACTGGAC
2470  GAAAAAGGAAACCTAGTTTTTGTCTTTAATTTTCACTGGAC
2469  GAAAAAGGAAACCTAGTTTTTGTCTTTAATTTTCACTGGAC
2553  GAAAAAGGAAACCTAGTTTTTGTCTTTAATTTTCACTGGAC

2588  TTTGGTGGCTTCGGGAGAATTGATCATAATGCCGAATATTT
2590  TTTGGTGGCTTCGGGAGAATTGATCATAATGCCGAATATTT
2589  TTTGGTGGCTTCGGGAGAATTGATCATAATGCCGAATATTT
2673  TTTGGTGGCTTCGGGAGAATTGATCATAATGCCGAATCTTT

2708  CTAGTAGACAAACTAGAAG-------------------------
2710  CTAGTAGACAAAGAAGAAGAAGAAGAAGAAGAAGAAGAAGA
2709  CTAGTAGACAAAGAAGAAGAAGAAGAAGAAGAAG--------
2793  CTAGTAGACAAAGAAGAAGAAGAAGAAGAAG---   -------
```

Fig. 8 Sheet 8

Fig. 8 SHEET 7

```
TGATAAATGGATTGAGTTGCTCAAGAAACGGGATGAGGATTGGAGA
TGATAAACGGATTGAGTTGCTCAAGAAACGGGATGAGGATTGGAGA
TGATAAATGGATTGAGTTGCTCAAGAAACGGGATGAGGATTGGAGA
TGATAAATGGATTGAGTTGCTCAAGAAACGGGATGAGGATTGGAGA

TCAAGCTCTAGTCGGTGATAAAACTATAGCATTCTGGCTGATGGAC
TCAAGCTCTAGTCGGTGATAAAACTATAGCATTCTGGCTGATGGAC
TCAAGCTCTAGTCGGTGATAAAACTATAGCATTCTGGCTGATGGAC
TCAAGCTCTAGTCGGTGATAAAACTATAGCATTCTGGCTGATGGAC

GATGATTAGGCTTGTAACTATGGGATTAGGAGGAGAAGGGTACCTA
GATGATTAGGCTTGTAACTATGGGATTAGGAGGAGAAGGGTACCTA
GATGATTAGGCTTGTAACTATGGGATTAGGAGGAGAAGGGTACCTA
GATGATTAGGCTTGTAACTATGGGATTAGGAGGAGAAGGGTACCTA

CTCAGTAATTCCCGGAAACCAATTCAGTTATGATAAATGCAGACGG
CTCAGTAATCCCCGGAAACCAATTCAGTTATGATAAATGCAGACGG
CTCAGTAATTCCCAGAAACCAATTCAGTTATGATAAATGCAGACGG
CTCAGTAATTCCCGGAAACCAATTCAGTTATGATAAATGCAGACGG

TGAAGATAAATATGAGTTTATGACTTCAGAACACCAGTTCATATCA
TGAAGATAAATATGAGTTTATGACTTCAGAACACCAGTTCATATCA
TGAAGATAAATATGAGTTTATGACTTCAGAACACCAGTTCATATCA
TGAAGATAAATATGAGTTTATGACTTCAGAACACCAGTTCATATCA

AAATAGCTATTCAGACTATCGCATAGGCTGCCTGAAGCCTGGAAAA
AAAAAGCTATTCAGACTATCGCATACCTGCCTGAAGCCTGGAAAA
AAAAGGCTATTCAGACTATCGCATAGGCTGCCTGAAGCCTGGAAAA
AAAAAGCTATTCAGACTATCGCATAGGCTGCCTGAAGCCTGGAAAA

CACCTCTGAAGGATCGTATGATGATCGTCCTTGTTCAATTATGGTG
CACCTTTGAAGGATGGTATGATGATCGTCCTCGTTCAATTATGGTG
CACCTTTGAAGGATGGTATGATGATCGTCCTCGTTCAATTATGGTG
CACCTTTGAAGGATGGTATGATGATCGTCCTCGTTCAATTATGGTG

-----TAGCAGTAGTAGAAGAACCCATTG------AAGAATGAACG
AGAAGTAGCACCAGTAGAAGAAGTAGTAGTAGAAGAAGAATGAACG
-----TAGCAGTAGTAGAAGAAGTAGTAGTAGAAGAAGAATGAACG
-----TAGCAGTAGTAGAAGAAGTAGTAGTAGAAGAAGAATGAACG
```

Fig. 8 Sheet 9

Fig. 8 SHEET 8

```
GTGGGTGATATTGTTCATACACTGACAAATAGA  11con.seq
GTGGGTGATATTGTTCATACACTGACAAATAGA  19con.seq
GTGGGTGATATTGTTCATACACTGACAAATAGA  10con.seq
GTGGGTGATATTGTTCATACACTGACAAATAGA  psbe2con.seq AAGGATATGTATGATTTTATGGCTCTGGATAGA  11con.seq
AAGGATATGTATGATTTTATGGCTCTGGATAGA  19con.seq
AAGGATATGTATGATTTTATGGCTCTGGATAGA  10con.seq
AAGGATATGTATGATTTTATGGCTUTGGATAGA  psbe2con.seq AATTTCATGGGAAATGAATTCGGCCACCCTGAG  11con.seq
AATTTCATGGGAAATGAATTCGGCCACCCTGAG  19con.seq
AATTTCATGGGAAATGAATTCGGCCACCCTGAG  10con.seq
AATTTCATGGGAAATGAATTCGGCCACCCTGAG  psbe2con.seq AGATTTGACCTGGGAGATGCAGAATATTTAAGA  11con.seq
AGATTTGACCTGGGAGATGCAGAATATTTAAGA  19con.seq
AGATTTGACCTGGGAGATGCAGAATATTTAAGA  10con.seq
AGATTTGACCTGGGAGATGCAGAATATTTAAGA  psbe2con.seq CGAAAGGATGAAGGAGATAGGATGATTGTATTT  11con.seq
CGAAAGGATGAAGGAGATAGGATGATTGTATTT  19con.seq
CGAAAGGATGAAGGAGATAGGATGATTGTATTT  10con.seq
CGAAAGGATGAAGGAGATAGGATGATTGTATTT  psbe2con.seq TACAAGGTTCTCTTGGACTCAGATGATCCACTT  11con.seq
TACAAGGTTGCCTTGGACTCAGATGATCCACTT  19con.seq
TACAAGGTTGCCTTGGACTCAGATGATCCACTT  10con.seq
TACAAGGTTGCCTTGGACTCAGATGATCCACTT  psbe2con.seq TATGCACCTAGTAGAACAGCAGTGGTCTATGCA  11con.seq
TATGCACCTTGTAAAACAGCAGTGGTCTATGCA  19con.seq
TATGCACCTAGTAGAACAGCAGTGGTCTATGCA  10con.seq
TATGCACCTAGTAGAACAGCAGTGGTCTATGCA  psbe2con.seq AACTTGTGATCGCGTTGAAAGATTTGAACGTTA  11con.seq
AACTTGTGATCGCGTTGAAAGATTTGAACG---  19con.seq
AACTTGTGATCGCGTTGAAAGATTTGAACG---  10con.seq
AACTTGTGATCGCGTTGAAAGATTTGAACG---  psbe2con.seq
```

Fig. 8
SHEET 9

```
2795 CTTGGTCATCCACATAGAGCTTCTTGAC--------------
2827 ---------CTACATAGAGCTTCTTGACGTATCTGGCAATAT
2814 ---------CCACATAGAGCTTCTTGACGTATCTGGCAATAT
2895 ---------CTACATAGAGCTTCTTGACGTATCTGGCAATAT

2898 AGAGATGAAGTGCTGAACAAA--CATATGTAAAATCGATGAA
2937 AGAGATGAAGTGCTGAACAAA--CATATGTAAAATCGATGAA
2924 AGAGATGAAGTGCTGAACAAAAACATATGTAAAATCGATGAA
3005 AGAGATGAAGTGCTGAACAAA--CATATGTAAAATCGATGAA 2975
3012
3003
3123 GCCCACTAGAAATCAATTATGTGAGACCTAAAAAACAATAAC
```

Fig. 8 Sheet 11

Fig. 8 SHEET 10

```
---ATCAGTCTTGGCGGAATTCCATGTGACAACAAGGTTTGCACTT
TGCATCAGTCTTGGCGGAATTTCATGTGACAC-AAGGTTTGCAATT
TGCATTAGTCTTGGCGGAATTTCATGTGACAA-CAGGTTTGCAATT
TGCATCAGTCTTGGCGGAATTTCATGTGACAA-AAGGTTTGCAATT

TTTATGTCGAATGCTGGGACGATCGAATTCCTGCAGCC
TTTATGTCGAATGCTGGGACGATCGAATTCCTGCAG
TTTATGTCGAATGCTGGGACGATCGAATTCCTGCAGCC
TTTATGTCGAATGCTGGGACGGGCTTCAGCAGGTTTTGCTTAGTGA

CATAAAATGGAAATAGTGCTGATCTAATGATGTTTTAANCCNNNNA
```

Fig. 8 Sheet 12

Fig. 8 SHEET 11

```
CTTTCCACTATTAGTAGTCCACCGATATACGC  11con.seq
CTTTCCACTATTAGTAGTGCAACGATATACGC  19con.seq
CTTTCCACTATTAGTAGTGCAACGATATACGC  10con.seq
CTTTCCACTATTAGTAGTGCAACGATATACGC  psbe2con.seq 11con.seq
                                  19con.seq
                                  10con.seq
GTTCTGTAAATTGTCATCTCTTTANATGTACA  psbe2con.seq 11con.seq
                                  19con.seq
                                  10con.seq
AAAAAAAAAAAAAAAACTCGAG            psbe2con.seq
```

Fig. 8  SHEET 12

```
GGATGCTAATGTTTCTGTATTCTTGAAAAAGCACTCTCTTTCACGG
CCTACGATTACAAAGACATAAGAACTTTTTCGTGAGAGAAAGTGCC
    A  N  V  S  V  F  L  K  K  H  S  L  S  R

TTCTACAGTTGCAGCATCGGGGAAAGTCCTTGTGCCTGGAAYCCAG
AAGATGTCAACGTCGTAGCCCCTTTCAGGAACACGGACCTTRGGTC
    S  T  V  A  A  S  G  K  V  L  V  P  G  ?  Q

GACATCTCCAGAAAATTCCCCAGCATCAACTGATGTAGATAGTTCA
CTGTAGAGGTCTTTTAAGGGGTCGTAGTTGACTACATCTATCAAGT
    T  S  P  E  N  S  P  A  S  T  D  V  D  S  S

TGAGCCGTCAAGTGATCTTACAGGAAGTGTTGAAGAGCTGGATTTT
ACTCGGCAGTTCACTAGAATGTCCTTCACAACTTCTCGACCTAAAA
    E  P  S  S  D  L  T  G  S  V  E  E  L  D  F

TAAAACATTAAATACTTCTGAAGAGACAATTATTGATGAATCTGAT
ATTTTGTAATTTATGAAGACTTCTCTGTTAATAACTACTTAGACTA
    K  T  L  N  T  S  E  E  T  I  I  D  E  S  D

Hinc II
GATTTATGAAATAGACCCCCTTTTGACAAACTATCGTCAACACCTT
CTAAATACTTTATCTGGGGGAAAACTGTTTGATAGCAGTTGTGGAA
    I  Y  E  I  D  P  L  L  T  N  Y  R  Q  H  L
```

Fig. 9 Sheet 2

Fig. 9 SHEET 1

Bgl II

```
AAGATCTTGGCTGAAAAGTCTTCTTACAATTCCGAATCCCGACC
────┼────┼────┼────┼────┼────┼────┼────┼────┼ 90
TTCTAGAACCGACTTTTCAGAAGAATGTTAAGGCTTAGGGCTGG
  K  I  L  A  E  K  S  S  Y  N  S  E  S  R  P

AGTGATAGCTCCTCATCCTCAACAGACCAATTTGAGTTCACTGA
────┼────┼────┼────┼────┼────┼────┼────┼────┼ 180
TCACTATCGAGGAGTAGGAGTTGTCTGGTTAAACTCAAGTGACT
  S  D  S  S  S  S  T  D  Q  F  E  F  T  E

ACAATGGAACACGCTAGCCAGATTAAAACTGAGAACGATGACGT
────┼────┼────┼────┼────┼────┼────┼────┼────┼ 270
TGTTACCTTGTGCGATCGGTCTAATTTTGACTCTTGCTACTGCA
  T  M  E  H  A  S  Q  I  K  T  E  N  D  D  V

GCTTCATCACTACAACTACAAGAAGGTGGTAAACTGGAGGAGTC
────┼────┼────┼────┼────┼────┼────┼────┼────┼ 360
CGAAGTAGTGATGTTGATGTTCTTCCACCATTTGACCTCCTCAG
  A  S  S  L  Q  L  Q  E  G  G  K  L  E  E  S

AGGATCAGAGAGAGGGGCATCCCTCCACCTGGACTTGGTCAGAA
────┼────┼────┼────┼────┼────┼────┼────┼────┼ 450
TCCTAGTCTCTCTCCCCGTAGGGAGGTGGACCTGAACCAGTCTT
  R  I  R  E  R  G  I  P  P  P  G  L  G  Q  K

GATTACAGGTATTCACAGTACAAGAAACTGAGGGAGGCAATTGA
────┼────┼────┼────┼────┼────┼────┼────┼────┼ 540
CTAATGTCCATAAGTGTCATGTTCTTTGACTCCCTCCGTTAACT
  D  Y  R  Y  S  Q  Y  K  K  L  R  E  A  I  D
```

Fig. 9 SHEET 2

```
                              HinD III
CAAGTATGAGGGTGGTTTGGAAGCTTTTTCTCGTGGTTATGAAAAA
GTTCATACTCCCACCAAACCTTCGAAAAAGAGCACCAATACTTTTT
  K  Y  E  G  G  L  E  A  F  S  R  G  Y  E  K

Pvu II
GGCTCCTGGTGCCCAGTCAGCTGCCCTCATTGGAGATTTCAACAAT
CCGAGGACCACGGGTCAGTCGACGGGAGTAACCTCTAAAGTTGTTA
  A  P  G  A  Q  S  A  A  L  I  G  D  F  N  N

CTGGGAGATTTTCTGCCAAATAATGTGGATGGTTCTCCTGCAATT
GACCCTCTAAAAGACGGTTTATTACACCTACCAAGAGGACGTTAA
  W  E  I  F  L  P  N  N  V  D  G  S  P  A  I

TGTTAAGGATTCCATTCCTGCTTGGATCAACTACTCTTTACAGCTT
ACAATTCCTAAGGTAAGGACGAACCTAGTTGATGAGAAATGTCGAA
  V  K  D  S  I  P  A  W  I  N  Y  S  L  Q  L

AGAGGAGAGGTATRTCTTCCAACACCCACGGCCAAAGAAACCAAAG
TCTCCTCTCCATAYAGAAGGTTGTGGGTGCCGGTTTCTTTGGTTTC
  E  E  R  Y  ?  F  Q  H  P  R  P  K  K  P  K
```

Fig. 9 Sheet 4

Fig. 9 SHEET 3

```
ATGGGTTTCACTCGTAGTGCTACAGGTATCACTTACCGTGAGTG
----+----+----+----+----+----+----+----+----+ 630
TACCCAAAGTGAGCATCACGATGTCCATAGTGAATGGCACTCAC
 M  G  F  T  R  S  A  T  G  I  T  Y  R  E  W

TGGGACGCAAATGCTGACATTATGACTCGGAATGAATTTGGTGT
----+----+----+----+----+----+----+----+----+ 720
ACCCTGCGTTTACGACTGTAATACTGAGCCTTACTTAAACCACA
 W  D  A  N  A  D  I  M  T  R  N  E  F  G  V

CCTCATGGGTCCAGAGTGAAGATACGYATGGACACTCCATCAGG
----+----+----+----+----+----+----+----+----+ 810
GGAGTACCCAGGTCTCACTTCTATGCRTACCTGTGAGGTAGTCC
 P  H  G  S  R  V  K  I  R  M  D  T  P  S  G

CCTGATGAAATTCCATATAATGGAATATATTATGATCCACCCGA
----+----+----+----+----+----+----+----+----+ 900
GGACTACTTTAAGGTATATTACCTTATATAATACTAGGTGGGCT
 P  D  E  I  P  Y  N  G  I  Y  Y  D  P  P  E

TCGCTGAGAATATATGAATCTCATATTGGAATGAGTAGTCCGGA
----+----+----+----+----+----+----+----+----+ 990
AGCGACTCTTATATACTTAGAGTATAACCTTACTCATCAGGCCT
 S  L  R  I  Y  E  S  H  I  G  M  S  S  P  E
```

Fig. 9 SHEET 4

```
                                                    Xmn I
GCCTAAAATTAACTCATACGTGAATTTTAGAGATGAAGTTCTTCCT
---------------------------------------------
CGGATTTTAATTGAGTATGCACTTAAAATCTCTACTTCAAGAAGGA
  P   K   I   N   S   Y   V   N   F   R   D   E   V   L   P

TCAAGAGCATTCTTATTATGCTAGTTTTGGTTATCATGTCACAAAT
---------------------------------------------
AGTTCTCGTAAGAATAATACGATCAAAACCAATAGTACAGTGTTTA
  Q   E   H   S   Y   Y   A   S   F   G   Y   H   V   T   N

GTCTTTGATTGATAAAGCTCATGAGCTAGGAATTGTTGTTCTCATG
---------------------------------------------
CAGAAACTAACTATTTCGAGTACTCGATCCTTAACAACAAGAGTAC
  S   L   I   D   K   A   H   E   L   G   I   V   V   L   M

GAACATGTTTGACGGCACAGATAGTTGTTACTTTCACTCTGGAGCT
---------------------------------------------
CTTGTACAAACTGCCGTGTCTATCAACAATGAAAGTGAGACCTCGA
  N   M   F   D   G   T   D   S   C   Y   F   H   S   G   A

AAACTGGGAGGTACTTAGGTATCTTCTCTCAAATGCGAGATGGTGG
---------------------------------------------
TTTGACCCTCCATGAATCCATAGAAGAGAGTTTACGCTCTACCACC
  N   W   E   V   L   R   Y   L   L   S   N   A   R   W   W

ATCAATGATGTATACTCACCACGGATTATCGGTGGGATTCACTGGG
---------------------------------------------
TAGTTACTACATATGAGTGGTGCCTAATAGCCACCCTAAGTGACCC
  S   M   M   Y   T   H   H   G   L   S   V   G   F   T   G
```

Fig. 9 Sheet 6

Fig. 9 SHEET 5

```
CGCATAAAAAASCTTGGGTACAATGCGGTGCAAATTATGGCTAT
                                                          1080
GCGTATTTTTSGAACCCATGTTACGCCACGTTTAATACCGATA
  R  I  K  ?  L  G  Y  N  A  V  Q  I  M  A  I

TTTTTTGCACCAAGCAGCCGTTTTGGAACGCCCGACGACCTTAA
                                                          1170
AAAAAACGTGGTTCGTCGGCAAAACCTTGCGGGCTGCTGGAATT
  F  F  A  P  S  S  R  F  G  T  P  D  D  L  K

GACATTGTTCACAGCCATGCATCAAATAATACTTTAGATGGACT
                                                          1260
CTGTAACAAGTGTCGGTACGTAGTTTATTATGAAATCTACCTGA
  D  I  V  H  S  H  A  S  N  N  T  L  D  G  L
```

Sac I

```
CGTGGTTATCATTGGATGTGGGATTCCCGCCTCTTTAACTATGG
                                                          1350
GCACCAATAGTAACCTACACCCTAAGGGCGGAGAAATTGATACC
  R  G  Y  H  W  M  W  D  S  R  L  F  N  Y  G

TTGGATGAGTTCAAATTTGATGGATTTAGATTTGATGGTGTGAC
                                                          1440
AACCTACTCAAGTTTAAACTACCTAAATCTAAACTACCACACTG
  L  D  E  F  K  F  D  G  F  R  F  D  G  V  T

AACTACGAGGAATACTTTGGACTCGCAACTGATGTGGATGCTGT
                                                          1530
TTGATGCTCCTTATGAAACCTGAGCGTTGACTACACCTACGACA
  N  Y  E  E  Y  F  G  L  A  T  D  V  D  A  V
```

Fig. 9 SHEET 6

```
                        Hinc II
TGTGTATCTGATGCTGGTCAACGATCTTATTCACGGGCTTTTCCCA
ACACATAGACTACGACCAGTTGCTAGAATAAGTGCCCGAAAAGGGT
 V  Y  L  M  L  V  N  D  L  I  H  G  L  F  P TTGTATTCCCGTTCAAGATGGGGGTGTTGGCTTTGACTATCGGCTG
AACATAAGGGCAAGTTCTACCCCCACAACCGAAACTGATAGCCGAC
 C  I  P  V  Q  D  G  G  V  G  F  D  Y  R  L GGATGAGGATTGGAGAGTGGGTGATATTGTTCATACACTGACAAAT
CCTACTCCTAACCTCTCACCCACTATAACAAGTATGTGACTGTTTA
 D  E  D  W  R  V  G  D  I  V  H  T  L  T  N TCAAGCTCTAGTCGGTGATAAAACTATAGCATYCTGGCTGATGGAC
AGTTCGAGATCAGCCACTATTTTGATATCGTARGACCGACTACCTG
 Q  A  L  V  G  D  K  T  I  A  ?  W  L  M  D ATTAATAGATCGTGGGATAGCATTGCACAAGATGATTAGGCTTGTA
TAATTATCTAGCACCCTATCGTAACGTGTTCTACTAATCCGAACAT
 L  I  D  R  G  I  A  L  H  K  M  I  R  L  V
```

Fig. 9 Sheet 8

Fig. 9 SHEET 7

```
GATGCAATTACCATTGGTGAAGATGTTAGCGGAATGCCGACATT
─────┼─────┼─────┼─────┼─────┼─────┼─────┼──── 1620
CTACGTTAATGGTAACCACTTCTACAATCGCCTTACGGCTGTAA
  D   A   I   T   I   G   E   D   V   S   G   M   P   T   F
```

Nde I
```
CATATGGCAATTGCTGATAAATGGATTGAGTTGCTCAAGAAACG
─────┼─────┼─────┼─────┼─────┼─────┼─────┼──── 1710
GTATACCGTTAACGACTATTTACCTAACTCAACGAGTTCTTTGC
  H   M   A   I   A   D   K   W   I   E   L   L   K   K   R
```

```
AGAAGATGGTCGGAAAAGTGTGTTTCATMCGCTGAAAGTCATGA
─────┼─────┼─────┼─────┼─────┼─────┼─────┼──── 1800
TCTTCTACCAGCCTTTTCACACAAAGTAKGCGACTTTCAGTACT
  R   R   W   S   E   K   C   V   S   ?   A   E   S   H   D
```

Hinc II
```
AAGGATATGTATGATTTTATGGCTCTGGATAGACCGTCAACATC
─────┼─────┼─────┼─────┼─────┼─────┼─────┼──── 1890
TTCCTATACATACTAAAATACCGAGACCTATCTGGCAGTTGTAG
  K   D   M   Y   D   F   M   A   L   D   R   P   S   T   S
```

Asp 718
                      Kpn I
```
ACTATGGGATTAGGAGGAGAAGGGTACCTAAATTTCATGGGAAA
─────┼─────┼─────┼─────┼─────┼─────┼─────┼──── 1980
TGATACCCTAATCCTCCTCTTCCCATGGATTTAAAGTACCCTTT
  T   M   G   L   G   G   E   G   Y   L   N   F   M   G   N
```

Fig. 9 SHEET 8

EcoR I
```
TGAATTCGGCCACCCTGAGTGGATTGATTTCCCTAGGGCTGARCAA
ACTTAAGCCGGTGGGACTCACCTAACTAAAGGGATCCCGACTYGTT
  E  F  G  H  P  E  W  I  D  F  P  R  A  E  Q
```

Ssp I
```
TGATAAATGCAGACGGAGATTTGACCTGGGAGATGCAGAATATTTA
ACTATTTACGTCTGCCTCTAAACTGGACCCTCTACGTCTTATAAAT
  D  K  C  R  R  R  F  D  L  G  D  A  E  Y  L
```

```
TGAAGATAAATATGAGTTTATGACTTCAGAACACCAGTTCATATCA
ACTTCTATTTATACTCAAATACTGAAGTCTTGTGGTCAAGTATAGT
  E  D  K  Y  E  F  M  T  S  E  H  Q  F  I  S
```

```
CCTAGTTTTGTCTTTAATTTTCACTGGACAAATAGCTATTCAGAC
GGATCAAAACAGAAATTAAAAGTGACCTGTTTATCGATAAGTCTG
  L  V  F  V  F  N  F  H  W  T  N  S  Y  S  D
```

```
GGACTCAGATGATCCACTTTTTGGTGGCTTCGGGAGAATTGATCAT
CCTGAGTCTACTAGGTGAAAAACCACCGAAGCCCTCTTAACTAGTA
  D  S  D  D  P  L  F  G  G  F  G  R  I  D  H
```

```
YCGYYCAATTATGGTGTATGCACCTAGTAGAACAGCAGTGGTCTAT
RGCRRGTTAATACCACATACGTGGATCATCTTGTCGTCACCAGATA
  R  ?  I  M  V  Y  A  P  S  R  T  A  V  V  Y
```

```
NGAAGAATTTT
—————————→ 2531
NCTTCTTAAAA
  E  E  F
```

Fig 9 Sheet 10

Fig 9 SHEET 9

```
CACCTCTCTGATGGCTCAGTAATTCCCGGAAACCAATTCAGTTA
----+----+----+----+----+----+----+----+----+ 2070
GTGGAGAGACTACCGAGTCATTAAGGGCCTTTGGTTAAGTCAAT
 H  L  S  D  G  S  V  I  P  G  N  Q  F  S  Y
```

Nco I

```
AGATACCATGGGTTGCAAGAATTTGACCGGGCTATGCAGTATCT
----+----+----+----+----+----+----+----+----+ 2160
TCTATGGTACCCAACGTTCTTAAACTGGCCCGATACGTCATAGA
   R  Y  H  G  L  Q  E  F  D  R  A  M  Q  Y  L
```

```
CGAAAGGATGAAGGAGATAGGATGATTGTATTTGAAARAGGAAA
----+----+----+----+----+----+----+----+----+ 2250
GCTTTCCTACTTCCTCTATCCTACTAACATAAACTTTYCCTTT
   R  K  D  E  G  D  R  M  I  V  F  E  ?  G  N
```

```
TATCGCATAGGCTGCCTGAAGCCTGGAAAATACAAGGTTGGCTT
----+----+----+----+----+----+----+----+----+ 2340
ATAGCGTATCCGACGGACTTCGGACCTTTTATGTTCCAACCGAA
   Y  R  I  G  C  L  K  P  G  K  Y  K  V  G  L
```

Ssp I

```
AATGCCGAATATTTCACCTCTGAAGGATCGTATGATGATCGYCC
----+----+----+----+----+----+----+----+----+ 2430
TTACGGCTTATAAAGTGGAGACTTCCTAGCATACTACTAGCRGG
   N  A  E  Y  F  T  S  E  G  S  Y  D  D  R  P
```

```
GCACTAGTAGACAAANTAGAAGNAGAAGAAGAAGAAGAANCCGN
----+----+----+----+----+----+----+----+----+ 2520
CGTGATCATCTGTTTNATCTTCNTCTTCTTCTTCTTNGGCN
   A  L  V  D  K  ?  E  ?  E  E  E  E  E  ?  ?
```

Fig. 9 SHEET 10

```
                    10            20            30
 1   --GATGGGGCCTTGAACTCAGCAATTTGACACTCAGT
 1   TTGATGGG-CCTTGAACTCAGCAATTTGACACTCAGT
 1   TTGATGGGGCCTTGAACTCAGCAATTTGACACTCAGT
 1   T-----------------------------------
 1   ------------------------------------

80            90           100
 69  TTTTTCTCTTAATTCCAACCAAGG-AATGAATAAAAA
 70  TTTTTCTCTTAATTCCAACCAGGGGAATGAATAAAAG
 71  TTTTTCTCTTAATTCCAACCAAGG-AATGAATAAAAG
  7  ------------------------------AAGAG
  1  ------------------------------

150           160           170
138  GAAAGATGGTGTATACACTCTCTGGAGTTCGTTTTCC
140  GAAAGATGGTGTATATACTCTCTGGAGTTCGTTTTCC
140  GAAAGATGGTGTATACACTCTCTGGAGTTCGTTTTCC
 33  --------------------------------TCT
  1  ------------------------------

220           230           240
208  CAGCAGTAATGGTGATCGGAGGAATGCTAATATTTCT
210  CAGCAGTAATGGTGATCGGAGGAATGCTAATGTTTCT
210  CAGCAGTAATGGTGATCGGAGGAATGCTAATGTTTCT
 48  CA---------------------------------
  1  ---------------------GGATGCTAATGTTTCT 290           300           310   *
278  ATCTTGGCTGAAAAGTCTTCTTACAATTCCGAATCCC
280  ATCTTGGCTGAAAAGTCTTCTTACAATTCCGAATTCC
280  ATCTTGGCTGAAAAGTCTTCTTACAATTCCGAATTCC
 57  ATCTTGGCTGAAAAGTCTTCTTACAATTCCGAATTCC
 50  ATCTTGGCTGAAAAGTCTTCTTACAATCCGAATCCC
                                        *
```

Fig. 10 Sheet 2

Fig. 10 SHEET 1

```
          40        50        60        70
          |         |         |         |
TAGTTACACTGCCATCACTTATCAGATCTCTAT   10con. seq
TAGTTACACTCCTATCACTTATCAGATCTCTAT   11con. seq
TAGTTACACTCCTATCACTTATCAGATCTCTAT   19con. seq
-----------CATTA-----------------   86CON. SEQ
---------------------------------   pcrsbe2con. seq 110       120       130       140
          |         |         |         |
GATAGATTTGTAAAAACCCTAAGGAGAGAAGAA   10con. seq
GATAGATTTGTAAAAACCCTAAGGAGAGAAGAA   11con. seq
GATAGATTTGTAAAAACCCTAAGGAGAGAAGAA   19con. seq
GAGAAATT------AACTATGAGAGGA------   86CON. SEQ
---------------------------------   pcrsbe2con. seq 180       190       200       210
          |         |         |         |
TACTGTTCCATCAGTGTACAAATCTAATGGATT   10con. seq
TACTGTTCCATCAGTGTACAAATCTAATGGATT   11con. seq
TACTGTTCCATCAGTGTACAAATCTAATGGATT   19con. seq
CACCAT--CACCA-------------------T   86CON. SEQ
---------------------------------   pcrsbe2con. seq 250       260       270       280
          |         |         |         |
GTATTCTTGAAAAAACACTCTCTTTCACGGAAG   10con. seq
GTATTCTTGAAAAAGCACTCTCTTTCACGGAAG   11con. seq
GTATTCTTGAAAAAGCACTCTCTTTCACGGAAG   19con. seq
-----------------------CCATGG--G   86CON. SEQ
GTATTCTTGAAAAAGCACTCTCTTTCACGGAAG   pcrsbe2con. seq 320       330       340       350
          |         |         |         |
GACCTTCTACAATTGCAGCATCGGGGAAAGTCC   10con. seq
GACCTTCTACAGTTGCAGCATCGGGGAAAGTCC   11con. seq
GACCTTCTACAGTTGCAGCATCGGGGAAAGTCC   19con. seq
GACCTTCTACAGTTGCAGCATCGGGGAAAGTCC   86CON. SEQ
GACCTTCTACAGTTGCAGCATCGGGGAAAGTCC   pcrsbe2con. seq
```

Fig. 10 SHEET 2

```
              360 *       370         380
          ┌─────────────────────────────────────┐
    348   │ TTGTGCCTGGAA T CCAGAGTGATAGCTCCTCATCCTC
    350   │ TTGTGCCTGGAACCCAGAGTGATAGCTCCTCATCCTC
    350   │ TTGTGCCTGGAACCCAGAGTGATAGCTCCTCATCCTC
    127   │ TTGTGCCTGGAACCCAGAGTGATAGCTCCTCATCCTC
    120   │ TTGTGCCTGGAA Y CCAGAGTGATAGCTCCTCATCCTC 430        440         450
          ┌─────────────────────────────────────┐
    418   │ AGAAAATTCCCCAGCATCAACTGATGTAGATAGTTCA
    420   │ AGAAAATTCCCCAGCATCAACTGATGTAGATAGTTCA
    420   │ AGAAAATTCCCCAGCATCAACTGATGTAGATAGTTCA
    197   │ AGAAAATTCCCCAGCATCAACTGATGTAGATAGTTCA
    190   │ AGAAAATTCCCCAGCATCAACTGATGTAGATAGTTCA 500        510         520
          ┌─────────────────────────────────────┐
    488   │ AACGATGACGTTGAGCCGTCAAGTGATCTTACAGGAA
    490   │ AACGATGACGTTGAGCCGTCAAGTGATCTTACAGGAA
    490   │ AACGATGACGTTGAGCCGTCAAGTGATCTTACAGGAA
    267   │ AACGATGACGTTGAGCCGTCAAGTGATCTTACAGGAA
    260   │ AACGATGACGTTGAGCCGTCAAGTGATCTTACAGGAA 570        580         590
          ┌─────────────────────────────────────┐
    558   │ AACTACAAGAAGGTGGTAAACTGGAGGAGTCTAAAAC
    560   │ AACTACAAGAAGGTGGTAAACTGGAGGAGTCTAAAAC
    560   │ AACTACAAGAAGGTGGTAAACTGGAGGAGTCTAAAAC
    337   │ AACTACAAGAAGGTGGTAAACTGGAGGAGTCTAAAAC
    330   │ AACTACAAGAAGGTGGTAAACTGGAGGAGTCTAAAAC 640        650         660
          ┌─────────────────────────────────────┐
    628   │ ATCTGATAGGATCAGAGAGAGGGGCATCCCTCCACCT
    630   │ ATCTGATAGGATCAGAGAGAGGGGCATCCCTCCACCT
    630   │ ATCTGATAGGATCAGAGAGAGGGGCATCCCTCCACCT
    407   │ ATCTGATAGGATCAGAGAGAGGGGCATCCCTCCACCT
    400   │ ATCTGATAGGATCAGAGAGAGGGGCATCCCTCCACCT
```

Fig. 10 Sheet 4

Fig. 10 SHEET 3

```
           390       400       410       420
    AACAGATCAATTTGAGTTCGCTGAGACATCTCC  10con. seq
    AACAGACCAATTTGAGTTCACTGAGACATCTCC  11con. seq
    AACAGACCAATTTGAGTTCACTGAGACATCTCC  19con. seq
    AACAAACCAATTTGAGTTCACTGAGACATCTCC  86CON. SEQ
    AACAGACCAATTTGAGTTCACTGAGACATCTCC  pcrsbe2con. seq 460       470       480       490
    ACAATGGAACACGCTAGCCAGATTAAAACTGAG  10con. seq
    ACAATGGAACACGCTAGCCAGATTAAAACTGAG  11con. seq
    ACAATGGAACACGCTAGCCAGATTAAAACTGAG  19con. seq
    ACAATGGAACACGCTAGCCAGATTAAAACTGAG  86CON. SEQ
    ACAATGGAACACGCTAGCCAGATTAAAACTGAG  pcrsbe2con. seq 530       540       550       560
    GTGTTGAAGAGCTGGATTTTGCTTCATCACTAC  10con. seq
    GTGTTGAAGAGCTGGATTTTGCTTCATCACTAC  11con. seq
    GTGTTGAAGAGCTGGATTTTGCTTCATCACTAC  19con. seq
    GTGTTGAAGAGCTGGATTTTGCTTCATCACTAC  86CON. SEQ
    GTGTTGAAGAGCTGGATTTTGCTTCATCACTAC  pcrsbe2con. seq 600       610       620       630
    ATTAAATACTTCTGAAGAGACAATTATTGATGA  10con. seq
    ATTAAATACTTCTGAAGAGACAATTATTGATGA  11con. seq
    ATTAAATACTTCTGAAGAGACAATTATTGATGA  19con. seq
    ATTAAATACTTCTGAAGAGACAATTATTGATGA  86CON. SEQ
    ATTAAATACTTCTGAAGAGACAATTATTGATGA  pcrsbe2con. seq 670       680       690       700
    GGACTTGGTCAGAAGATTTATGAAATAGACCCC  10con. seq
    GGACTTGGTCAGAAGATTTATGAAATAGACCCC  11con. seq
    GGACTTGGTCAGAAGATTTATGAAATAGACCCC  19con. seq
    GGACTTGGTCAGAAGATTTATGAAATAGACCCC  86CON. SEQ
    GGACTTGGTCAGAAGATTTATGAAATAGACCCC  pcrsbe2con. seq
```

Fig.10 SHEET 4

```
                    710       720       730
        ┌──────────────────────────────────────────┐
    698 │ CTTTTGACAAACTATCGTCAACACCTTGATTACAGGT     │
    700 │ CTTTTGACAAACTATCGTCAACACCTTGATTACAGGT     │
    700 │ CTTTTGACAAACTATCGTCAACACCTTGATTACAGGT     │
    477 │ CTTTTGACAAACTATCGTCAACACCTTGATTACAGGT     │
    470 │ CTTTTGACAAACTATCGTCAACACCTTGATTACAGGT     │
        └──────────────────────────────────────────┘

780       790       800
        ┌──────────────────────────────────────────┐
    768 │ ACAAGTATGAGGGTGGTTTGGAAGCTTTTCTCGTGG      │
    770 │ ACAAGTATGAGGGTGGTTTGGAAGC-TTTTCTCGTGG     │
    770 │ ACAAGTATGAGGGTGGTTTGGAAGCCTTTTCTCGTGG     │
    547 │ ACAAGTATGAGGGTGGTTTGGAAGCTTTTCTCGTGG      │
    540 │ ACAAGTATGAGGGTGGTTTGGAAGCTTTTCTCGTGG      │
        └──────────────────────────────────────────┘

850       860       870
        ┌──────────────────────────────────────────┐
    838 │ AGGTATCACTTACCGTGAGTGGGCTCCTGGTGCCCAG     │
    839 │ AGGTATCACTTACCGTGAGTGGGCTCCTGGTGCCCAG     │
    840 │ AGGTATCACTTACCGTGAGTGGGCTCTTGGTGCCCAG     │
    617 │ AGGTATCACTTACCGTGAGTGGGCTCCTGGTGCCCAG     │
    610 │ AGGTATCACTTACCGTGAGTGGGCTCCTGGTGCCCAG     │
        └──────────────────────────────────────────┘

920       930       940
        ┌──────────────────────────────────────────┐
    908 │ GACGCAAATGCTGACTTTATGACTCGGAATGAATTTG     │
    909 │ GACGCAAATGCTGACATTATGACTCGGAATGAATTTG     │
    910 │ GACGCAAATGCTGACATTATGACTCGGAATGAATTTG     │
    687 │ GACGCAAATGCTGACATTATGACTCGGAATGAATTTG     │
    680 │ GACGCAAATGCTGACATTATGACTCGGAATGAATTTG     │
        └──────────────────────────────────────────┘

990      1000      1010
        ┌──────────────────────────────────────────┐
    978 │ ATGGTTCTCCTGCAATTCCTCATGGGTCCAGAGTGAA     │
    979 │ ATGGTTCTCCTGCAATTCCTCATGGGTCCAGAGTGAA     │
    980 │ ATGGTTCTCCTGCAATTCCTCATGGGTCCAGAGTGAA     │
    757 │ ATGGTTCTCCTGCAATTCCTCATGGGTCCAGAGTGAA     │
    750 │ ATGGTTCTCCTGCAATTCCTCATGGGTCCAGAGTGAA     │
        └──────────────────────────────────────────┘
```

Fig. 10 Sheet 6

Fig. 10 SHEET 5

```
           740         750         760         770
        ATTCACAGTACAAGAAACTGAGGGAGGCAATTG  10con. seq
        ATTCACAGTACAAGAAACTGAGGGAGGCAATTG  11con. seq
        ATTCACAGTACAAGAAACTGAGGGAGGCAATTG  19con. seq
        ATTCACAGTACAAGAAACTGAGGGAGGCAATTG  86CON. SEQ
        ATTCACAGTACAAGAAACTGAGGGAGGCAATTG  pcrsbe2con. seq 810         820         830         840
        TTATGAAAGAATGGGTTTCACTCGTAGTGCTAC  10con. seq
        TTATGAAAAAATGGGTTTCACTCGTAGTGCTAC  11con. seq
        TTATGAAAAAATGGGTTTCACTCGTAGTGCTAC  19con. seq
        TTATGAAAAAATGGGTTTCACTCGTAGTGCTAC  86CON. SEQ
        TTATGAAAAAATGGGTTTCACTCGTAGTGCTAC  pcrsbe2con. seq 880         890         900         910
        TCAGCTGCCCTCATTGGGGATTTCAACAATTGG  10con. seq
        TCAGCTGCCCTCATTGGAGATTTCAACAATTGG  11con. seq
        TCAGCTGCCCTCATTGGAGATTTCAACAATTGG  19con. seq
        TCAGCTGCCCTCATTGGAGATTTCAACAATTGG  86CON. SEQ
        TCAGCTGCCCTCATTGGAGATTTCAACAATTGG  pcrsbe2con. seq 950         960         970         980
        GTGTCTGAGAGATTTTTCTGCCAAATAATGTGG  10con. seq
        GTGTCTGGGAGATTTTTCTGCCAAATAATGTGG  11con. seq
        GTGTCTGGGAGATTTTTCTGCCAAATAATGTGG  19con. seq
        GTGTCTGGGAGATTTTTCTGCCAAATAATGTGG  86CON. SEQ
        GTGTCTGGGAGATTTTTCTGCCAAATAATGTGG  pcrsbe2con. seq 1020        1030        1040        1050
        GATACGTATGGACACTCCATCAGGTGTTAAGGA  10con. seq
        GATACGTATGGACACTCCATCAGGTGTTAAGGA  11con. seq
        GATACGTATGGACACTCCATCAGGTGTTAAGGA  19con. seq
        GATACGTATGGACACTCCATCAGGTGTTAAGGA  86CON. SEQ
        GATACGYATGGACACTCCATCAGGTGTTAAGGA  pcrsbe2con. seq
```

Fig. 10 SHEET 6

```
         1060      1070      1080
1048  TTCCATTCCTGCTTGGATCAACTACTCTTTACAGCTT
1049  TTCCATTCCTGCTTGGATCAACTACTCTTTACAGCTT
1050  TTCCATTCCTGCTTGGATCAACTACTCTTTACAGCTT
 827  TTCCATTCCTGCTTGGATCAACTACTC--TACAGCTT
 820  TTCCATTCCTGCTTGGATCAACTACTCTTTACAGCTT 1130      1140      1150
1118  GATCCACCCGAAGAGGAGAGGTATATCTTCCAACACC
1119  GATCCACCCGAAGAGGAGAGGTATATCTTCCAACACC
1120  GATCCACCCGAAGAGGAGAGGTATATCTTCCAACACC
 895  GATCCACCCGAAGAGGAGAGGTATATCTTCCAACACC
 890  GATCCACCCGAAGAGGAGAGGTATRTCTTCCAACACC 1200      1210      1220
1188  ATGAATCTCATATTGGAATGAGTAGTCCGGAGCCTAA
1189  ATGAATCTCATATTGGAATGAGTAGTCCGGAGCCTAA
1190  ATGAATCTCATATTGGAATGAGTAGTCCGGAGCCTAA
 965  ATGAATCTCATATTGGAATGAGTAGTCCGGAGCCTAA
 960  ATGAATCTCATATTGGAATGAGTAGTCCGGAGCCTAA 1270      1280      1290
1258  TCTTCCTCGCATAAAAAAAGCTTGGGTACAATGCGGT
1259  TCTTCCTCGCATAAAAAA-GCTTGGGTACAATGCGCT
1260  TCTTCCTCGCATAAAAAA-GCTTGGGTACAATGCGCT
1035  TCTTCCTCGCATAAAAAA-GCTTGGGTACAATGCGCT
1030  TCTTCCTCGCATAAAAAA-SCTTGGGTACAATGCGGT 1340      1350      1360
1328  TGCTAGTTTTGGTTATCATGTCACAAATTTTTTTGCA
1328  TGCTAGTTTTGGTTATCATGTCACAAATTTTTTTGCA
1329  CGCTAGTTTTGGTTATCATGTCACAAATTTTTTTGCA
1104  TGCTAGTTTTGGTTATCATGTCACAAATTTTTTTGCA
1099  TGCTAGTTTTGGTTATCATGTCACAAATTTTTTTGCA
```

Fig. 10 Sheet 8

Fig. 10 SHEET 7

```
      1090        1100        1110        1120
CCTGATGAAATTCCATATAATGGAATATATTAT  10con. seq
CCTGATGAAATTCCATATAATGGAATATATTAT  11con. seq
CCTGATGAAATTCCATATAATGGAATACATTAT  19con. seq
CCTGATGAAATTCCATATAATGGAATATATTAT  86CON. SEQ
CCTGATGAAATTCCATATAATGGAATATATTAT  pcrsbe2con. seq 1160        1170        1180        1190
CACGGCCAAAGAAACCAAAGTCGCTGAGAATAT  10con. seq
CACGGCCAAAGAAACCAAAGTCGCTGAGAATAT  11con. seq
CACGGCCAAAGAAACCAAAGTCGCTGAGAATAT  19con. seq
CACGGCCAAAGAAACCAAAGTCGCTGAGAATAT  86CON. SEQ
CACGGCCAAAGAAACCAAAGTCGCTGAGAATAT  pcrsbe2con. seq 1230        1240        1250        1260
AATTAACTCATACGTGAATTTTAGAGATGAAGT  10con. seq
AATTAACTCATACGTGAATTTTAGAGATGAAGT  11con. seq
AATTAACTCATACGTGAATTTTAGAGATGAAGT  19con. seq
AATTAACTCATACGTGAATTTTAGAGATGAAGT  86CON. SEQ
AATTAACTCATACGTGAATTTTAGAGATGAAGT  pcrsbe2con. seq 1300        1310        1320        1330
GCAAATTATGGCTATTCAAGAGCATTCTTATTA  10con. seq
GCGAATTATGGCTATTCAAGAGCATTCTTATTA  11con. seq
GCAAATTATGGCTATTCAAGAGCATTCTTATTA  19con. seq
GCAAATTATGGCTATTCAAGAGCATTCTTATTA  86CON. SEQ
GCAAATTATGGCTATTCAAGAGCATTCTTATTA  pcrsbe2con. seq 1370        1380        1390        1400
CCAAGCAGCCGTTTTGGAACGCCCGACGACCTT  10con. seq
CCAAGCAGCCGTTTTGGAACGCCCGACGACCTT  11con. seq
CCAAGCAGCCGTTTTGGAACGCCCGACGACCTT  19con. seq
CCAAGCAGCCGTTTTGGAACGCCCGACGACCTT  86CON. SEQ
CCAAGCAGCCGTTTTGGAACGCCCGACGACCTT  pcrsbe2con. seq
```

Fig. 10 SHEET 8

```
              1410        1420        1430
1398  AAGTCTTTGATTGATAAAGCTCATGAGCTAGGAATTG
1398  AAGTCTTCGATTGATAAAGCTCATGAGCTAGGAATTG
1399  AAGTCTTTGATTGATAAAGCTCATGAGCTAGGAATTG
1174  AAGTCTTTGATTGATAAAGCTCATGAGCTAGGAATTG
1169  AAGTCTTTGATTGATAAAGCTCATGAGCTAGGAATTG 1480        1490        1500
1468  CAAATAATACTTTAGATGGACTGAACATGTTTGACGG
1468  CAAATAATACTTTAGATGGACTGAACATGTTTGACGG
1469  CAAATAATACTTTAGATGGACTGAACATGTTTGACTG
1244  CAAATAATACTTTAGATGGACTGAACATGTTTGACGG
1239  CAAATAATACTTTAGATGGACTGAACATGTTTGACGG 1550        1560        1570
1538  TGGTTATCATTGGATGTGGGATTTCCGCCTCTTTAAC
1538  TGGTTATCATTGGATGTGGGATT-CCGCCTCTTTAAC
1539  TGGTTATCATTGGATGTGGGATTCCCGCCTCTTTAAC
1314  TGGTTATCATTGGATGTGGGATTCCCGCCTTTTAAC
1309  TGGTTATCATTGGATGTGGGATTCCCGCCTCTTTAAC 1620        1630        1640
1608  TCAAATGCGAGATGGTGGTTGGATGAGTTCAAATTTG
1607  TCAAATGCGAGATGGTGGTTGGATGAGTTCAAATTTG
1609  TCAAATGCGAGATGGTGGTTGGATGCGTTCAAATTTG
1384  TCAAATGCGAGATGGTGGTTGGATGAGTTCAAATTTG
1379  TCAAATGCGAGATGGTGGTTGGATGAGTTCAAATTTG 1690        1700        1710
1678  TGTGTACTCACCACGGATTATCGGTGGGATTCACTGG
1677  TGTATACTCACCACGGATTATCGGTGGGATTCACTGG
1679  TGTATATTCACCACGGATTATCGGTGGGATTCACTGG
1454  TGTATACTCACCACGGATTATCGGTGGGATTCACTGG
1449  TGTATACTCACCACGGATTATCGGTGGGATTCACTGG
```

Fig. 10 Sheet 10

Fig. 10 SHEET 9

```
     1440        1450        1460        1470
TTGTTCTCATGGACATTGTTCACAGCCATGCAT  10con. seq
TTGTTCTCATGGACATCGTTCACAGCCATGCAT  11con. seq
TTGTTCTCATGGACATTGTTCACAGCCATGCAT  19con. seq
TTGTTCTCATGGACATTGTTCACAGCCATGCAT  86CON. SEQ
TTGTTCTCATGGACATTGTTCACAGCCATGCAT  pcrsbe2con. seq 1510        1520        1530        1540
CACAGATAGTTGTTACTTTCACTCTGGAGCTCG  10con. seq
CACCGATAGTTGTTACTTTCACTCTGGAGCTCG  11con. seq
CACCGATAGTTGTTACTTTCACTCTGGAGCTCG  19con. seq
CACCGATAGTTGTTACTTTCACTCTGGAGCTCG  86CON. SEQ
CACAGATAGTTGTTACTTTCACTCTGGAGCTCG  pcrsbe2con. seq 1580        1590        1600        1610
TATGGAAACTGGGAGGTACTTAGGTATCTTCTC  10con. seq
TATGGAAACTGGGAGGTACTTAGGTATCTTCTC  11con. seq
TATGGAAACTGGGAGGTACTTAGGTATCTTCTC  19con. seq
TATGGAAACTGGGAGGTACTTAGGTATCTTCTC  86CON. SEQ
TATGGAAACTGGGAGGTACTTAGGTATCTTCTC  pcrsbe2con. seq 1650        1660        1670        1680
ATGGATTTAGATTTGATGGTGTGACATCAATGA  10con. seq
ATGGATTTAGATTCGATGGTGTGACATCAATGA  11con. seq
ATGGATTTAGATTTGATGGTGTGACATCAATGA  19con. seq
ATGGATTTAGATTTGATGGTGTGACATCAATGA  86CON. SEQ
ATGGATTTAGATTTGATGGTGTGACATCAATGA  pcrsbe2con. seq 1720        1730        1740        1750
GAACTACGAGGAATACTTTGGACTCGCAACTGA  10con. seq
GAACTACGAGGAATACTTTGGACTCGCAACTGA  11con. seq
GAACTACGAGGAATACTTTGGACTCGCAACTGA  19con. seq
GAACTACGAGGAATACTTTGGACTCGCAACTGA  86CON. SEQ
GAACTACGAGGAATACTTTGGACTCGCAACTGA  pcrsbe2con. seq
```

Fig. 10 SHEET 10

```
                  1760      1770      1780
1748  TGTGGATGCTGTTGTGTATCTGATGCTGGTCAACGAT
1747  TGTGGATGCTGTTGTGTATCTGATGCTGGTCAACGAT
1749  TGTGGATGCTGTTGTGTATCTGATGCTGGTCAACGAT
1524  TGTGGATGCTGTTGTGTATCTGATGCTGGTCAACGAT
1519  TGTGGATGCTGTTGTGTATCTGATGCTGGTCAACGAT 1830      1840      1850
1818  ATTGGTGAAGATGTTAGCGGAATGCCGACATTTTGTG
1817  ATTGGTGAAGATGTTAGCGGAATGCCGACATTTTGTA
1819  ATTGGTGAAGATGTTAGCGGAATGCCGACATTTTGTA
1594  ATTGGTGAAGATGTTAGCGGAATGCCGACATTTTGTA
1589  ATTGGTGAAGATGTTAGCGGAATGCCGACATTTTGTA 1900      1910      1920
1888  ATCGGCTGCATATGGCAATTGCTGATAAATGGATTGA
1887  ATCGGCTGCATATGGCAATTGCTGATAAATGGATTGA
1889  ATCGGCTGCATATGGCAATTGCTGATAAACGGATTGA
1664  ATCGGCTGCATATGGCAATTGCTGATAAATGGATTGA
1659  ATCGGCTGCATATGGCAATTGCTGATAAATGGATTGA 1970      1980      1990
1958  GGGTGATATTGTTCATACACTGACAAATAGAAGATGG
1957  GGGTGATATTGTTCATACACTGACAAATAGAAGATGG
1959  GGGTGATATTGTTCATACACTGACAAATAGAAGATGG
1734  GGGTGATATTGTTCATACACTGACAAATAGAAGATGG
1729  GGGTGATATTGTTCATACACTGACAAATAGAAGATGG 2040      2050      2060
2028  GATCAAGCTCTAGTCGGTGATAAAACTATAGCATTCT
2027  GATCAAGCTCTAGTCGGTGATAAAACTATAGCATTCT
2029  GATCAAGCTCTAGTCGGTGATAAAACTATAGCATTCT
1804  GATCAAGCTCTAGTCGGTGATAAAACTATAGCATTCT
1799  GATCAAGCTCTAGTCGGTGATAAAACTATAGCATYCT
```

Fig. 10 Sheet 12

Fig. 10 SHEET 11

```
          1790          1800          1810          1820
           |             |             |             |
CTTATTCATGGGCTTTTCCCAGATGCAATTACC  10con. seq
CTTATTCATAGGCTTTTCCCAGATGCAATTACC  11con. seq
CTTATTCATGGGCTTTTCCCAGATGCAATTACC  19con. seq
CTTATTCATGGGCTTTTCCCAGATGCAATTACC  86CON. SEQ
CTTATTCACGGGCTTTTCCCAGATGCAATTACC  pcrsbe2con. seq 1860          1870          1880          1890
           |             |             |             |
TTCCCGTTCAAGATGGGGGTGTTGGCTTTGACT  10con. seq
TTCCCGTTCAAGATGGGGGTGTTGGCTTTGACT  11con. seq
TTCCCGTCCAAGAGGGGGGTGTTGGCTTTGACT  19con. seq
TTCCCGTTCAAGATGGGGGTGTTGGCTTTGACT  86CON. SEQ
TTCCCGTTCAAGATGGGGGTGTTGGCTTTGACT  pcrsbe2con. seq 1930          1940          1950          1960
           |             |             |             |
GTTGCTCAAGAAACGGGATGAGGATTGGAGAGT  10con. seq
GTTGCTCAAGAAACGGGATGAGGATTGGAGAGT  11con. seq
GTTGCTCAAGAAACGGGATGAGGATTGGAGAGT  19con. seq
GTTGCTCAAGAAACGGGATGAGGATTGGAGAGT  86CON. SEQ
GTTGCTCAAGAAACGGGATGAGGATTGGAGAGT  pcrsbe2con. seq 2000          2010          2020          2030
           |             |             |             |
TCGGAAAAGTGTGTTTCATACGCTGAAAGTCAT  10con. seq
TCGGAAAAGTGTGTTTCATACGCTGAAAGTCAT  11con. seq
TCGGAAAAGTGTGTTTCATACGCTGAAAGTCAT  19con. seq
TCGGAAAAGTGTGTTTCATACGCTGAAAGTCAT  86CON. SEQ
TCGGAAAAGTGTGTTTCATMCGCTGAAAGTCAT  pcrsbe2con. seq 2070          2080          2090          2100
           |             |             |             |
GGCTGATGGACAAGGATATGTATGATTTTATGG  10con. seq
GGCTGATGGACAAGGATATGTATGATTTTATGG  11con. seq
GGCTGATGGACAAGGATATGTATGATTTTATGG  19con. seq
GGCTGATGGACAAGGATATGTATGATTTTATGG  86CON. SEQ
GGCTGATGGACAAGGATATGTATGATTTTATGG  pcrsbe2con. seq
```

Fig. 10

```
             2110    *    2120        2130
2098  CTCTGGATAGACCGTCAACATCATTAATAGATCGTGG
2097  CTCTGGATAGACCGCCAACATCATTAATAGATCGTGG
2099  CTCTGGATAGACCGTCAACATCATTAATAGATCGTGG
1874  CTCTGGATAGACCGCCAACATCATTAATAGATCGTGG
1869  CTCTGGATAGACCGYCAACAYCATTAATAGATCGTGG
                    *

2180        2190        2200
2168  TATGGGATTAGGAGGAGAAGGGTACCTAAATTTCATG
2167  TATGGGATTAGGAGGAGAAGGGTACCTAAATTTCATG
2169  TATGGGATTAGGAGGAGAAGGGTACCTAAATTTCATG
1944  TATGGGATTAGGAGGAGAAGGGTACCTAAATTTCATG
1939  TATGGGATTAGGAGGAGAAGGGTACCTAAATTTCATG

2250    *    2260        2270
2238  TTCCCTAGGGCTGAACAACACCTCTCTGATGGCTCAG
2237  TTCCCTAGGGCTGAGCACACCTTTCTGATGGCTCAG
2239  TTCCCTAGGGCTGAACAACACCTCTCTGATGGCTCAG
2014  TTCCCTAGGGCTGAACAACACCTCTCTGATGACTCAG
2009  TTCCCTAGGGCTGARCAACACCTCTCTGATGGCTCAG
                    *

2320        2330        2340
2308  GCAGACGGAGATTTGACCTGGGAGATGCAGAATATTT
2307  GCAGACGGAGATTTGACCTGGGAGATGCAGAATATTT
2309  GCAGACGGAGATTTGACCTGGGAGATGCAGAATATTT
2084  GCAGACGGAGATTTGACCTGGGAGATGCAGAATATTT
2079  GCAGACGGAGATTTGACCTGGGAGATGCAGAATATTT 2390        2400        2410
2378  TATGCAGTATCTTGAAGATAAATATGAGTTTATGACT
2377  TATGCAGTATCTTGAAGATAAATATGAGTTTATGACT
2379  TATGCAGTATCTTGAAGATAAATATGAGTTTATGACT
2154  TATGCAGTATCTTGAAGATAAATATGAGTTTATGACT
2149  TATGCAGTATCTTGAAGATAAATATGAGTTTATGACT
```

Fig. 10 Sheet 14

Fig. 10 SHEET 13

```
        2140      2150      2160      2170
GATAGCATTACACAAGATGATTAGGCTTGTAAC  10con. seq
GATAGCATTGCACAAGATGATTAGGCTTGTAAC  11con. seq
GATAGCATTGCACAAGATGATTAGGCTTGTAAC  19con. seq
GATAGCATTGCACAAGATGATTAGGCTTGTAAC  86CON. SEQ
GATAGCATTGCACAAGATGATTAGGCTTGTAAC  pcrsbe2con. seq 2210      2220      2230      2240
GGAAATGAATTCGGCCACCCTGAGTGGATTGAT  10con. seq
GGAAATGAATTCGGCCACCCTGAGTGGATTGAT  11con. seq
GGAAATGAATTCGGCCACCCTGAGTGGATTGAT  19con. seq
GGAAATGAATTCGGCCACCCTGAGTGGATTGAT  86CON. SEQ
GGAAATGAATTCGGCCACCCTGAGTGGATTGAT  pcrsbe2con. seq 2280      2290      2300      2310
TAATTCCCAGAAACCAATTCAGTTATGATAAAT  10con. seq
TAATTCCCGGAAACCAATTCAGTTATGATAAAT  11con. seq
TAATCCCCGGAAACCAATTCAGTTATGATAAAT  19con. seq
TAATTCCCGGAAACCAATTCAGTTATGATAAAT  86CON. SEQ
TAATTCCCGGAAACCAATTCAGTTATGATAAAT  pcrsbe2con. seq 2350      2360      2370      2380
AAGATACCGTGGGTTGCAAGAATTTGACCGGGC  10con. seq
AAGATACCATGGGTTACAAGAATTTGACTGGGC  11con. seq
AAGATACCGTGGGTTGCAAGAATTTGACCGGCC  19con. seq
AAGATACCGTGGGTTGCAAGAATTTGACCGGGC  86CON. SEQ
AAGATACCATGGGTTGCAAGAATTTGACCGGGC  pcrsbe2con. seq 2420      2430      2440      2450
TCAGAACACCAGTTCATATCACGAAAGGATGAA  10con. seq
TCAGAACACCAGTTCATATCACGAAAGGATGAA  11con. seq
TCAGAACACCAGTTCATATCACGAAAGGATGAA  19con. seq
TCAGAACACCAGTTCATATCACGAAAGGATGAA  86CON. SEQ
TCAGAACACCAGTTCATATCACGAAAGGATGAA  pcrsbe2con. seq
```

Fig. 10 SHEET 14

```
              2460        2470    *  2480
       2448  GGAGATAGGATGATTGTATTTGAAAAAGGAAACCTAG
       2447  GGAGATAGGATGATTGTATTTGAAAGAGGAAACCTAG
       2449  GGAGATAGGATGATTGTATTTGAAAAAGGAAACCTAG
       2224  GGAGATAGGATGATTGTATTTGAAAAAGGAAACCTAG
       2219  GGAGATAGGATGATTGTATTTGAAARAGGAAACCTAG
                                       *

2530        2540        2550
       2518  ATTCAGACTATCGCATAGGCTGCCTGAAGCCTGGAAA
       2517  ATTCAGACTATCGCATAGGCTGCCTGAAGCCTGGAAA
       2519  ATTCAGACTATCGCATAGCCTGCCTGAAGCCTGGAAA
       2294  ATTCAGACTATCGCATAGGCTGCCTGAAGCCTGGAAA
       2289  ATTCAGACTATCGCATAGGCTGCCTGAAGCCTGGAAA 2600        2610        2620
       2588  TTTTGGTGGCTTCGGGAGAATTGATCATAATGCCGAA
       2587  TTTTGGTGGCTTCGGGAGAATTGATCATAATGCCGAA
       2589  TTTTGGTGGCTTCGGGAGAATTGATCATAATGCCGAA
       2364  TTTTGGTGGCTTCGGGAGAATTGATCATAATGCCGAA
       2359  TTTTGGTGGCTTCGGGAGAATTGATCATAATGCCGAA 2670        2680    * 2690
       2658  CCTCGTTCAATTATGGTGTATGCACCTAGTAGAACAG
       2657  CCTTGTTCAATTATGGTGTATGCACCTAGTAGAACAG
       2659  CCTCGTTCAATTATGGTGTATGCACCTTGTAAAACAG
       2434  CCTCGTTCAATTATGGTGTATGCACCTTGTAGAACAG
       2429  CCTCGTTCAATTATGGTGTATGCACCTAGTAGAACAG
                                       *

2740        2750        2760
       2722  ------AAGAAGAAGAAGAAGAAGTAGCAGTAGT
       2722  ---------------------AGAAGTAGCAGTAGT
       2729  AAGAAGAAGAAGAAGAAGAAGAAGTAGCAGCAGT
       2501  AAGAAGAAGAAGAAGAAGAAGAAGTAGCAGTAGT
       2499  NAGAAGAAGAAGAAGAAN----------------
```

Fig. 10 Sheet 16

Fig. 10 SHEET 15

```
         2490      2500      2510   ✱  2520
         |         |         |         |
TTTTTGTCTTTAATTTTCACTGGACAAAAGGCT   10con. seq
TTTTCGTCTTTAATTTTCACTGGACAAATAGCT   11con. seq
TTTTTGTCTTTAATTTTCACTGGACAAAAAGCT   19con. seq
TTTTTGTCTTTAATTTTCACTGGACAAAAAGCT   86CON. SEQ
TTTTTGTCTTTAATTTTCACTGGACAAATAGCT   pcrsbe2con. seq
                                ✱

2560      2570      2580      2590
         |         |         |         |
ATACAAGGTTGCCTTGGACTCAGATGATCCACT   10con. seq
ATACAAGGTTGTCTTGGACTCAGATGATCCACT   11con. seq
ATACAAGGTTGCCTTGGACTCAGATGATCCACT   19con. seq
ATACAAGGTTGCCTTGGACTCAGATGATCCACT   86CON. SEQ
ATACAAGGTTGGCTTGGACTCAGATGATCCACT   pcrsbe2con. seq 2630   ✱ 2640   ✱ 2650      2660
         |         |         |         |
TATTTCACCTTTGAAGGATGGTATGATGATCGT   10con. seq
TATTTCACCTCTGAAGGATCGTATGATGATCGT   11con. seq
TATTTCACCTTTGAAGGATGGTATGATGATCGT   19con. seq
TATTTCACCTTTGAAGGATGGTATGATGATCGT   86CON. SEQ
TATTTCACCTCTGAAGGATCGTATGATGATCGT   pcrsbe2con. seq
                ✱         ✱

2700      2710      2720      2730
         |         |         |         |
CAGTGGTCTATGCACTAGTAGACAAAG-----   10con. seq
CAGTGGTCTATGCACTAGTAGACAAACT---   11con. seq
CAGTGGTCTATGCACTAGTAGACAAAGAAGAAG   19con. seq
CAGTGGTCTATGCACTAGTAGACAAAG--AAG   86CON. SEQ
CAGTGGTCTATGCACTAGTAGACAAANTAGAAG   pcrsbe2con. seq 2770      2780      2790      2800
         |         |         |         |
AGAAGAAGTAGTAGTAGAAGAAGAATGAACGAA   10con. seq
AGAAGAACCCATTG------AAGAATGAACGAA   11con. seq
AGAAGAAGTAGTAGTAGAAGAAGAATGAACGAA   19con. seq
AGAAGAAGTAGTAGTAGAAGAAGAATGAACGAA   86CON. SEQ
---------------CCGNNGAAGAAT-------   pcrsbe2con. seq
```

Fig. 10

```
                    2810          2820          2830
2786  CTTGTGATCGCGTTGAAAGATTTGAACGCCACATAGA
2764  CTTGTGATCGCGTTGAAAGATTTGAACGTTACTTGG-
2799  CTTGTGATCGCGTTGAAAGATTTGAACGCTACATAGA
2571  CTTGTG
2529  ------------------------------------
```

```
                    2880          2890          2900
2856  CTTGGCGGAATTTCATGTGACAACA-GGTTTGCAATT
2829  CTTGGCGGAATTGCATGTGACAACAAGGTTTGCAGTT
2869  CTTGGCGGAATTTCATGTGACACAA-GGTTTGCAATT
2576  
2529  -------------------------------------
```

```
                    2950          2960          2970
2925  GAGATGAAGTGCTGAACAAAAACATATGTAAAATCGA
2899  GAGATGAAGTGCTGAACAAA--CATATGTAAAATCGA
2938  GAGATGAAGTGCTGAACAAA--CATATGTAAAATCGA
2576  
2529  --------------------- ---------------
```

```
                    3020          3030
2995  CCTGCAG-----------------CC
2967  CCTGCAG-----------------CC
3006  CCTGCAGGCCGGGGGACCCCTTAGTTCT
2576  
2529  --------------------------T
```

Fig. 10 Sheet 18

Fig. 10 SHEET 17

```
     2840      2850      2860      2870
GCTTCTTGACGTATCTGGCAATATTGCATTAGT  10con. seq
--TCATCCACATA--GAGCTTCTTGACATCAGT  11con. seq
GCTTCTTGACGTATCTGGCAATATTGCATCAGT  19con. seq
                                   86CON. SEQ
--------------------------------   pcrsbe2con. seq 2910      2920      2930      2940
CTTTCCACTATTAGTAGTGCAACGATATACGCA  10con. seq
CTTTCCACTATTAGTAGTCCACCGATATACGCA  11con. seq
CTTTCCACTATTAGTAGTGCAACGATATACGCA  19con. seq
                                   86CON. SEQ
--------------------------------   pcrsbe2con. seq 2980      2990      3000      3010
TGAATTTATGTCGAATGCTGGGACGATCGAATT  10con. seq
TGAATTTATGTCGAATGCTGGGACGATCGAATT  11con. seq
TGAATTTATGTCGAATGCTGGGACGATCGAATT  19con. seq
                                   86CON. SEQ
--------------------------------   pcrsbe2con. seq
```

10con. seq
                                    11con. seq
                                    19con. seq
                                    86CON. SEQ
                                    pcrsbe2con. seq

Fig. 10 SHEET 18

Fig. 12 SHEET 1

```
                    NcoI
                    BstXI
TCATTAAAGAGGAGAAATTAACTATGAGAGGATCTCACCATCACCATCACCATGGGATCT
————————+————————+————————+————————+————————+————————+  60
AGTAATTTCTCCTCTTTAATTGATACTCTCCTAGAGTGGTAGTGGTAGTGGTACCCTAGA
                      M  R  G  S  H  H  H  H  H  H  G  I

EcoRI
TGGCTGAAAAGTCTTCTTACAATTCCGAATTCCGACCTTTCTACAGTTGCAGCATCGGGGA
————————+————————+————————+————————+————————+————————+  120
ACCGACTTTTCAGAAGAATGTTAAGGCTTAAGGCTGGAAAGATGTCAACGTCGTAGCCCCT
   L  A  E  K  S  S  Y  N  S  E  F  R  P  S  T  V  A  A  S  G

AAGTCCTTGTGCCTGGAACCCAGAGTGATAGCTCCTCATCCTCAACAAACCAATTTGAGT
————————+————————+————————+————————+————————+————————+  180
TTCAGGAACACGGACCTTGGGTCTCACTATCGAGGAGTAGGAGTTGTTTGGTTAAACTCA
   K  V  L  V  P  G  T  Q  S  D  S  S  S  S  T  N  Q  F  E

TCACTGAGACATCTCCAGAAAATTCCCCAGCATCAACTGATGTAGATAGTTCAACAATGG
————————+————————+————————+————————+————————+————————+  240
AGTGACTCTGTAGAGGTCTTTTAAGGGGTCGTAGTTGACTACATCTATCAAGTTGTTACC
   F  T  E  T  S  P  E  N  S  P  A  S  T  D  V  D  S  S  T  M
```

Fig. 12 SHEET 2

```
AACACGCTAGCCAGATTAAAAACTGAGAACGATGACGTTGAGCCGTCAAGTGATCTTACAG      300
TTGTGCGATCGGTCTAATTTTTGACTCTTGCTACTGCAACTCGGCAGTTCACTAGAATGTC
 E  H  A  S  Q  I  K  T  E  N  D  D  V  E  P  S  S  D  L  T

GAAGTGTTGAAGAGCTTGCTTCATCACTACAAGAAGGTAAACTGG                      360
CTTCACAACTTCTCGACCTAAAACGAAGTAGTGATGTTGATGTTCTTCCACCATTTGACC
 G  S  V  E  E  L  D  F  A  S  S  L  Q  E  G  G  K  L

AGGAGTCTAAAAACATTAAATACTTTCTGAAGAGACAATTATTGATGAATCTGATAGGATCA   420
TCCTCAGATTTTGTAATTTATGAAAGACTTCTCTGTTAATAACTACTTAGACTATCCTAGT
 E  E  S  K  T  L  N  T  S  E  E  T  I  I  D  E  S  D  R  I

GAGAGAGGGCATCCCCTCCACCTGGACTTGGTCAGAAGATTTATGAAATAGACCCCCTTT     480
CTCTCTCCCCGTAGGGAGGTGGACCTGAACCAGTCTTCTAAATACTTTATCTGGGGAAA
 R  E  R  G  I  P  P  P  G  L  G  Q  K  I  Y  E  I  D  P  L
                              Hinc II TGACAAACTATCGTCAACACCTTGATTACACAGTATTCACAGTACAAGAAACTGAGGGAGG   540
ACTGTTTGATAGCAGTTGTGGAACTAATGTCCATAAGTGTCATGTTCTTTGACTCCCTCC
 L  T  N  Y  R  Q  H  L  D  Y  R  Y  S  Q  Y  K  K  L  R  E
```

Fig 12
SHEET 3

```
                HinD III
CAATTGACAAGTATGAGGGTGGTTTGGAAGCTTTTTCTCGTGGTTATGAAAAATGGGTT
         +         +         +         +         +         + 600
GTTAACTGTTCATACTCCCACCAAACCTTCGAAAAGAGCACCAATACTTTTTACCCAA
 A  I  D  K  Y  E  G  G  L  E  A  F  S  R  G  Y  E  K  M  G

Pvu II
TCACTCGTAGTGCTACAGGTATCACTTACCGTGAGTGGGCTCCTGGTGCCCAGTCAGCTG
         +         +         +         +         +         + 660
AGTGAGCATCACGATGTCCATAGTGAATGGCACTCACCCGAGGACCACGGGTCAGTCGAC
 F  T  R  S  A  T  G  I  T  Y  R  E  W  A  P  G  A  Q  S  A

CCCTCATTGGAGAGATTTCAACAATTGGGACGCAAATGCTGACATTATGACTCGGAATGAAT
         +         +         +         +         +         + 720
GGGAGTAACCTCTAAAGTTGTTAACCCTGCGTTTACGACTGTAATACTGAGCCTTACTTA
 A  L  I  G  D  F  N  N  W  D  A  N  A  D  I  M  T  R  N  E

TTGGTGTCTGGGAGATTTTTCTGCCAAATAATGTGGATGGTTCTCCTGCAATTCCTCATG
         +         +         +         +         +         + 780
AACCACAGACCCTCTAAAAGACGGTTTATTACACCTACCAAGAGGACGTTAAGGAGTAC
 F  G  V  W  E  I  F  L  P  N  N  V  D  G  S  P  A  I  P  H
```

Fig. 12
SHEET 4

```
SnaB I
GGTCCAGAGTGAAGATACGTATGGACACTCCATCAGGTGTTAAGGATTCCATTCCTGCTT
                                                              840
CCAGGTCTCACTTCTATGCATACCTGTGAGGTAGTCCACAATTCCTAAGGTAAGGACGAA
G  S  R  V  K  I  R  M  D  T  P  S  G  V  K  D  S  I  P  A

GGATCAACTACTCTTCACAGCTTCCTGATGAAATTCCATATAATGGAATATATTATGATC
                                                              900
CCTAGTTGATGAGAAGTGTCGAAGGACTACTTTAAGGTATATTACCTTATATAATACTAG
W  I  N  Y  S  S  Q  L  P  D  E  I  P  Y  N  G  I  Y  Y  D

CACCCGAAGAGGAGAGGTATATCTTCCAACACCCACGGCCAAAGAAACCAAAGTCGCTGA
                                                              960
GTGGGCTTCTCCTCTCCATATAGAAGGTTGTGGGTGCCGGTTTCTTTGGTTTCAGCGACT
P  P  E  E  E  R  Y  I  F  Q  H  P  R  P  K  K  P  K  S  L

GAATATATGAATCTCATATATTGGAATGAGTAGTCCGGAGCCTAAAAATTAACTCATACGTGA
                                                              1020
CTTATATACTTAGAGTATAACCTTACTCATCAGGCCTCGGATTTTAATTGAGTATGCACT
R  I  Y  E  S  H  I  G  M  S  S  P  E  P  K  I  N  S  Y  V
```

Fig. 12
SHEET 5

```
                    XmnI              HinDIII
ATTTTAGAGAGATGAAGTTCTTCCTCGCATAAAAAAGCTTGGGTACAATGCGGGTGCAAATTA
                                                              1080
TAAAATCTCTACTTCAAGAAGGAGCGTATTTTTCGAACCCATGTTACGCCCACGTTTAAT
 N  F  R  D  E  V  L  P  R  I  K  K  L  G  Y  N  A  V  Q  I

TGGCTATTCAAGAGCATTCTTATTATGCTAGTTTTGGTTATCATGTCACAAATTTTTTG
                                                              1140
ACCGATAAGTTCTCGTAAGAATAATACGATCAAAACCAATAGTACAGTGTTTAAAAAAC
 M  A  I  Q  E  H  S  Y  Y  A  S  F  G  Y  H  V  T  N  F  F

CACCAAGCAGCCGTTTGGAACGCCCGAGACGCCTTAAGTCTTTGATTGATAAAGCTCATG
                                                              1200
GTGGTTCGTCGGCAAAACCTTGCGGGCTCTGCGGAATTCAGAAACTAACTATTTCGAGTAC
 A  P  S  S  R  F  G  T  P  D  D  L  K  S  L  I  D  K  A  H
                                                     NsiI

AGCTAGGAATTGTTGTTCTCATGGACATTGTTCACAGCCATGCATCAAATAATACTTTAG
                                                              1260
TCGATCCTTAACAACAAGAGTACCTGTAACAAGTGTCGGTACGTAGTTTATTATGAAATC
 E  L  G  I  V  V  L  M  D  I  V  H  S  H  A  S  N  N  T  L
```

```
                                     SacI
ATGGACTGAACATGTTTGACGGCACCGATAGTTGTTACTTTCACTCTGGAGCTCGTGGTT
                                                                 1320
TACCTGACTTGTACAAACTGCCGTGGCTATCAACAATGAAAGTGAGACCTCGAGCACCAA
 D  G  L  N  M  F  D  G  T  D  S  C  Y  F  H  S  G  A  R  G

ATCATTGGATGTGTGGGATTCCCGCCTTTTTAACTATGGAAACTGGGAGGTACTTAGGTATC
                                                                 1380
TAGTAACCTACACCCTAAGGGCGGAAAAATTGATACCTTTGACCCTCCATGAATCCATAG
 Y  H  W  M  D  S  R  L  F  N  Y  G  N  W  E  V  L  R  Y

TTCTCTCAAATGCGAGATGGTTGGATGAGTTCAAATTTGATGGATTTAGATTTGATG
                                                                 1440
AAGAGAGTTTACGCTCTACCAACCTACTCAAGTTTAAATCTAAACTAC
 L  L  S  N  A  R  W  W  L  D  E  F  K  F  D  G  F  R  F  D

GTGTGACATCAATGATGTATACTCACCACGGATTATCGGTGGGATTCACTGGGAACTACG
                                                                 1500
CACACTGTAGTTACTACATATGAGTGGTGCCTAATAGCCACCCTAAGTGACCCTTGATGC
 G  V  T  S  M  M  Y  T  H  H  G  L  S  V  G  F  T  G  N  Y
```

Fig. 12
SHEET 6

Fig 12
SHEET 7

```
                                                           Hinc II
AGGAATACTTTGGACTCGCAACTGATGTGTATCTGATGCTGGTCAACG
                                                                    1560
TCCTTATGAAACCTGAGCGTTGACTACACCTACGACAACACATAGACTACGACCAGTTGC
 E  E  Y  F  G  L  A  T  D  V  D  A  V  V  Y  L  M  L  V  N ATCTTATTCATGGGCTTTTCCCAGATGCAATTACCATTGGTGAAGATGTTAGCGGAATGC
                                                                    1620
TAGAATAAGTACCCGAAAAGGGTCTACGTTAATGGTAACCACTTCTACAATCGCCTTACG
 D  L  I  H  G  L  F  P  D  A  I  T  I  G  E  D  V  S  G  M CGACATTTTGTATTCCCGTTCAAGATGGGGGTGTTTGGCTTTGACTATCGGCTGCATATGG
                                                                    1680
GCTGTAAAACATAAGGGCAAGTTCTACCCCCACAAACCGAAACTGATAGCCGACGTATACC
 P  T  F  C  I  P  V  Q  D  G  G  V  G  F  D  Y  R  L  H  M CAATTGCTGATAAATGATTGAGTTGCTCAAGAAAACGGGATGAGGATTGGAGAGTGGGTG
                                                                    1740
GTTAACGACTATTTACCTAACTCAACGAGTTCTTTGCCTACTCCTAACCTCTCCACCCAC
 A  I  A  D  K  W  I  E  L  L  K  K  R  D  E  D  W  R  V  G ATATTGTTCATACACTGACAAATAGAAGATGGTCGGAAAAGTGTTTCATACGCTGAAA
                                                                    1800
TATAACAAGTATGTGACTGTTTATCTTCTACCAGCCTTTTCACACAAAGTATGCGACTTT
 D  I  V  H  T  L  T  N  R  R  W  S  E  K  C  V  S  Y  A  E
```

Fig 12
SHEET 8

```
GTCATGATCAAGCTCTAGTCGGTGATAAAACTATAGCATTCTGGCTGATGGACAAGGATA
CAGTACTAGTTCGAGATCAGCCACTATTTTGATATCGTAAGACCGACTACCTGTTCCTAT    1860
 S  H  D  Q  A  L  V  G  D  K  T  I  A  F  W  L  M  D  K  D

TGTATGATTTTATGGCTCTGGATAGACCGCCAACATCATTAATAGATCGTGGGATAGCAT
ACATACTAAAATACCGAGACCTATCTGGCGGTTGTAGTAATTATCTAGCACCCTATCGTA    1920
 M  Y  D  F  M  A  L  D  R  P  P  T  S  L  I  D  R  G  I  A
                                                      Asp 718
                                                       Kpn I

TGCACAAGATGATTAGGCTTGTAACTATGGGATTAGGAGGAGAAGGTACCTAAATTTCA
ACGTGTTCTACTAATCCGAACATTGATACCCTAATCCTCCTCTTCCCATGGATTTAAAGT    1980
 L  H  K  M  I  R  L  V  T  M  G  L  G  G  E  G  Y  L  N  F
                              EcoR I

TGGGAAATGAATTCGGCCACCTGAGTGGATTGATTTCCCTAGGGCTGAACAACACCTCT
ACCCTTTACTTAAGCCGGTGGACTCACCTAACTAAAGGGATCCCGACTTGTTGTGGAGA    2040
 M  G  N  E  F  G  H  P  E  W  I  D  F  P  R  A  E  Q  H  L
```

Fig. 12
SHEET 9

```
TTGCCTTGGACTCAGATGATCCACTTTTTGGTGGCTTCGGGGAGAATTGATCATAATGCCG
    ----+----+----+----+----+----+----+----+----+----+----+----+  2400
AACGGAACCTGAGTCTACTAGGTGAAAAACCACCGAAGCCCTCTTAACTAGTATTACGGC
 V  A  L  D  S  D  D  P  L  F  G  G  F  G  G  R  I  D  H  N  A

SspI
AATATTTCACCTTTGAAGGATGGTATGATGATCGTCCTCGTTCAATTATGGTGTATGCAC
    ----+----+----+----+----+----+----+----+----+----+----+----+  2460
TTATAAAGTGGAAACTTCCTACCATACTACTAGCAGGAGCAAGTTAATACCACATACGTG
 E  Y  F  T  F  E  G  W  Y  D  D  R  P  R  S  I  M  V  Y  A

CTTGTAGAACAGCAGTGGTCTATGCACTAGTAGACAAAGAAGAAGAAGAAGAAGAAGAAG
    ----+----+----+----+----+----+----+----+----+----+----+----+  2520
GAACATCTTGTCGTCACCAGATACGTGATCATCTGTTTCTTCTTCTTCTTCTTCTTCTTC
 P  C  R  T  A  V  V  Y  A  L  V  D  K  E  E  E  E  E  E  E  E

AAGAAGAAGTAGCAGTAGTAGAAGAAGTAGTAGAAGAAGAATGAACGAACTTGTG
    ----+----+----+----+----+----+----+----+----+----+---→  2578
TTCTTCTTCATCGTCATCATCTTCTTCATCATCATCTTCTTCTTACTTGCTTGAACAC
 E  E  E  V  A  V  V  E  E  V  V  E  E  E  E
```

Fig 12
SHEET 10

PLANT STARCH COMPOSITION

FIELD OF THE INVENTION

This invention relates to novel nucleotide sequences, polypeptides encoded thereby, vectors and host cells and host organisms comprising one or more of the novel sequences, and to a method of altering one or more characteristics of an organism. The invention also relates to starch having novel properties and to uses thereof.

BACKGROUND OF THE INVENTION

Starch is the major form of carbon reserve in plants, constituting 50% or more of the dry weight of many storage organs—e.g. tubers, seeds of cereals. Starch is used in numerous food and industrial applications. In many cases, however, it is necessary to modify the native starches, via chemical or physical means, in order to produce distinct properties to suit particular applications. It would be highly desirable to be able to produce starches with the required properties directly in the plant, thereby removing the need for additional modification. To achieve this via genetic engineering requires knowledge of the metabolic pathway of starch biosynthesis. This includes characterisation of genes and encoded gene products which catalyse the synthesis of starch. Knowledge about the regulation of starch biosynthesis raises the possibility of "re-programming" biosynthetic pathways to create starches with novel properties that could have new commercial applications.

The commercially useful properties of starch derive from the ability of the native granular form to swell and absorb water upon suitable treatment. Usually heat is required to cause granules to swell in a process known as gelatinization, which has been defined (W A Atwell et al, Cereal Foods World 33, 306–311, 1988) as " . . . the collapse (disruption) of molecular order within the starch granule manifested in irreversible changes in properties such as granular swelling; native crystallite melting, loss of birefringence, and starch solubilization. The point of initial gelaltinization and the range over which it occurs is governed by starch concentration, method of observation, granule type, and heterogeneities within the granule population under observation". A number of techniques are available for the determination of gelatinization as induced by heating, a convenient and accurate method being differential scanning calorimetry, which detects the temperature range and enthalpy associated with the collapse of molecular orders within the granule. To obtain accurate and meaningful results, the peak and/or onset temperature of the endotherm observed by differential scanning calorimetry is usually determined.

The consequence of the collapse of molecular orders within starch granules is that the granules are capable of taking up water in a process known as pasting, which has been defined (W A Atwell et al, Cereal Foods World 33, 306–311, 1988) as " . . . the phenomenon following gelatinization in the dissolution of starch. It involves granular swelling, exudation of molecular components from the granule, and eventually, total disruption of the granules". The best method of evaluating pasting properties is considered to be the viscoamylograph (Atwell et al, 1988 cited above) in which the viscosity of a stirred starch suspension is monitored under a defined time/temperature regime. A typical viscoamylograph profile for potato starch shows an initial rise in viscosity, which is considered to be due to granule swelling. In addition to the overall shape of the viscosity response in a viscoamylograph, a convenient quantitative measure is the temperature of initial viscosity development (onset). FIG. 1 shows such a typical viscosity profile for potato starch, during and after cooking, and includes stages A–D which correspond to viscosity onset (A), maximum viscosity (B), complete dispersion (C) and reassociation of molecules (or retrogradation, D). In the figure, the dotted line represents viscosity (in stirring number units) of a 10% w/w starch suspension and the unbroken line shows the temperature in degrees centigrade. At a certain point, defined by the viscosity peak, granule swelling is so extensive that the resulting highly expanded structures are susceptible to mechanically-induced fragmentation under the stirring conditions used. With increased heating and holding at 95° C., further reduction in viscosity is observed due to increased fragmentation of swollen granules. This general profile has previously always been found for native potato starch.

After heating starches in water to 95° C. and holding at that temperature (for typically 15 minutes), subsequent cooling to 50° C. results in an increase in viscosity due to the process of retrogradation or set-back. Retrogradation (or set-back) is defined (Atwell et al., 1988 cited above) as " . . . a process which occurs when the molecules comprising gelatinised starch begin to reassociate in an ordered structure . . . ". At 50° C., it is primarily the amylose component which reassociates, as indicated by the increase in viscoamylograph viscosity for starch from normal maize (21.6% amylose) compared with starch from waxy maize (1.1% amylose) as shown in FIG. 2. FIG. 2 is a viscoamylograph of 10% w/w starch suspensions from waxy maize (solid line), conventional maize (dots and dashes), high amylose variety (HYLON® V starch, dotted line) and a very high amylose variety (HYLON® VII starch, crosses). The temperature profile is also shown by a solid line, as in FIG. 1. The extent of viscosity increase in the viscoamylograph on cooling and holding at 50° C. depends on the amount of amylose which is able to reassociate due to its exudation from starch granules during the gelatinization and pasting processes. A characteristic of amylose-rich starches from maize plants is that very little amylose is exuded from granules by gelatinization and pasting up to 95° C., probably due to the restricted swelling of the granules. This is illustrated in FIG. 2 which shows low viscosities for a high amylose (44.9%) starch (HYLON® V starch) from maize during gelatinization and pasting at 95° C. and little increase in viscosity on cooling and holding at 50° C. This effect is more extreme for a higher amylose content (58%, as in HYLON® VII starch), which shows even lower viscosities in the viscoamylograph test (FIG. 2). For commercially-available high amylose starches (currently available from maize plants, such as those described above), processing at greater than 100° C. is usually necessary in order to generate the benefits of high amylose contents with respect to increased rates and strengths of reassociation, but use of such high temperatures is energetically unfavourable and costly. Accordingly, there is an unmet need for starches of high amylose content which can be processed below 100° C. and still show enhanced levels of reassociation, as indicated for example by viscoamylograph measurements.

The properties of potato starch are useful in a variety of both food and non-food (paper, textiles, adhesives etc.) applications. However, for many applications, properties are not optimum and various chemical and physical modifications well known in the art are undertaken in order to improve useful properties. Two types of property manipulation which would be of use are: the controlled alteration of gelatinization and pasting temperatures; and starches which suffer less granular fragmentation during pasting than conventional starches.

Currently the only ways of manipulating the gelatinization and pasting temperatures of potato starch are by the inclusion of additives such as sugars, polyhydroxy compounds of salts (Evans & Haisman, Starke 34, 224–231, 1982) or by extensive physical or chemical pre-treatments (e.g. Stute, Starke 44, 205–214, 1992). The reduction of granule fragmentation during pasting can be achieved either by extensive physical pretreatments (Stute, Starke 44, 205–214, 1992) or by chemical cross-linking. Such processes are inconvenient and inefficient. It is therefore desirable to obtain plants which produce starch which intrinsically possesses such advantageous properties.

Starch consists of two main polysaccharides, amylose and amylopectin. Amylose is a generally linear polymer containing α-1,4 linked glucose units, while amylopectin is a highly branched polymer consisting of a α-1,4 linked glucan backbone with α-1,6 linked glucan branches. In most plant storage reserves amylopectin constitutes about 75% of the starch content. Amylopectin is synthesized by the concerted action of soluble starch synthase and starch branching enzyme [α-1,4 glucan: α-1,4 glucan 6-glycosyltransferase, EC 2.4.1.18]. Starch branching enzyme (SBE) hydrolyses α-1,4 linkages and rejoins the cleaved glucan, via an α-1,6 linkage, to an acceptor chain to produce a branched structure. The physical properties of starch are strongly affected by the relative abundance of amylose and amylopectin, and SBE is therefore a crucial enzyme in determining both the quantity and quality of starches produced in plant systems.

In most plants studied to date e.g. maize (Boyer & Preiss, 1978 Biochem. Biophys. Res. Comm. 80, 169–175), rice (Smyth, 1988 Plant Sci. 57, 1–8) and pea (Smith, Planta 175, 270–279), two forms of SBE have been identified, each encoded by a separate gene. A recent review by Burton et al., (1995 The Plant Journal 7, 3–15) has demonstrated that the two forms of SBE constitute distinct classes of the enzyme such that, in general, enzymes of the same class from different plants may exhibit greater similarity than enzymes of different classes from the same plant. In their review, Burton et al. termed the two respective enzyme families class "A" and class "B", and the reader is referred thereto (and to the references cited therein) for a detailed discussion of the distinctions between the two classes. One general distinction of note would appear to be the presence, in class A SBE molecules, of a flexible N-terminal domain, which is not found in class B molecules. The distinctions noted by Burton et al. are relied on herein to define class A and class B SBE molecules, which terms are to be interpreted accordingly.

However in potato, only one isoform of the SBE molecule (belonging to class B) has thus far been reported and only one gene cloned (Blennow & Johansson, 1991 Phytochem. 30, 437–444, and Koβmann el al., 1991 Mol. Gen. Genet. 230, 39–44). Further, published attempts to modify the properties of starch in potato plants (by preventing expression of the single known SBE) have generally not succeeded (e.g. Müller-Rober & Koβmann 1994 Plant Cell and Environment 17, 601–613).

SUMMARY OF THE INVENTION

In a first aspect the invention provides a nucleotide sequence encoding an effective portion of a class A starch branching enzyme (SBE) obtainable from potato plants.

Preferably the nucleotide sequence encodes a polypeptide comprising an effective portion of the amino acid sequence shown in FIG. 5 (excluding the sequence MNKRIDL, which does not represent part of the SBE molecule), or a functional equivalent thereof (which term is discussed below). The amino acid sequence shown in FIG. 5 (Seq ID No. 15) includes a leader sequence which directs the polypeptide, when synthesised in potato cells, to the amyloplast. Those skilled in the art will recognise that the leader sequence is removed to produce a mature enzyme and that the leader sequence is therefore not essential for enzyme activity. Accordingly, an "effective portion" of the polypeptide is one which possesses sufficient SBE activity to complement the branching enzyme mutation in E. coli KV 832 cells (described below) and which is active when expressed in E. coli in the phosphorylation stimulation assay. An example of an incomplete polypeptide which nevertheless constitutes an "effective portion" is the mature enzyme lacking the leader sequence. By analogy with the pea class A SBE sequence, the potato class A sequence shown in FIG. 5 probably possesses a leader sequence of about 48 amino acid residues, such that the N terminal amino acid sequence is thought to commence around the glutamic acid residue (E) at position 49 (EKSSYN . . . etc.). Those skilled in the art will appreciate that an effective portion of the enzyme may well omit other parts of the sequence shown in the figure without substantial detrimental effect. For example, the C-terminal glutamic acid-rich region could be reduced in length, or possibly deleted entirely, without abolishing class A SBE activity. A comparison with other known SBE sequences, especially other class A SBE sequences (see for example, Burton et al, 1995 cited above), should indicate those portions which are highly conserved (and thus likely to be essential for activity) and those portions which are less well conserved (and thus are more likely to tolerate sequence changes without substantial loss of enzyme activity).

Conveniently the nucleotide sequence will comprise substantially nucleotides 289 to 2790 of the DNA sequence (Seq ID No. 14) shown in FIG. 5 (which nucleotides encode the mature enzyme) or a functional equivalent thereof, and may also include further nucleotides at the 5' or 3' end. For example, for ease of expression, the sequence will desirably also comprise an in-frame ATG start codon, and may also encode a leader sequence. Thus, in one embodiment, the sequence further comprises nucleotides 145 to 288 of the sequence shown in FIG. 5. Other embodiments are nucleotides 228 to 2855 of the sequence labelled "psbe2con.seq" in FIG. 8, and nucleotides 57 to 2564 of the sequence shown in FIG. 12 (preferably comprising an in-frame ATG start codon, such as the sequence of nucleotides 24 to 56 in the same Figure), or functional equivalents of the aforesaid sequences.

The term "functional equivalent" as applied herein to nucleotide sequences is intended to encompass those sequences which differ in their nucleotide composition to that shown in FIG. 5 but which, by virtue of the degeneracy of the genetic code, encode polypeptides having identical or substantially identical amino acid sequences. It is intended that the term should also apply to sequences which are sufficiently homologous to the sequence of the invention that they can hybridise to the complement thereof under stringent hybridisation conditions—such equivalents will preferably possess at least 85%, more preferably at least 90%, and most preferably at least 95% sequence homology with the sequence of the invention as exemplified by nucleotides 289 to 2790 of the DNA sequence shown in FIG. 5. It will be apparent to those skilled in the art that the nucleotide sequence of the invention may also find useful application when present as an "antisense" sequence. Accordingly, functionally equivalent sequences will also include those sequences which can hybridise, under stringent hybridisation conditions, to the sequence of the invention (rather than the complement thereof). Such "antisense" equivalents will preferably possess at least 85%, more preferably at least 90%, and most preferably 95% sequence homology with the complement of the sequence of the invention as exemplified by nucleotides 289 to 2790 of the DNA sequence shown in FIG. 5. Particular functional equivalents are shown, for example, in FIGS. 8 and 10 (if one disregards the various frameshift mutations noted therein).

The invention also provides vectors, particularly expression vectors, comprising the nucleotide sequence of the invention. The vector will typically comprise a promoter and one or more regulatory signals of the type well known to those skilled in the art. The invention also includes provision of cells transformed (which term encompasses transduction and transfection) with a vector comprising the nucleotide sequence of the invention.

The invention further provides a class A SBE polypeptide, obtainable from potato plants. In particular the invention provides the polypeptide in substantially pure form, especially in a form free from other plant-derived (especially potato plant-derived) components, which can be readily accomplished by expression of the relevant nucleotide sequence in a suitable non-plant host (such as any one of the yeast strains routinely used for expression purposes, e.g. Pichia spp. or *Saccharomyces* spp). Typically the enzyme will substantially comprise the sequence of amino acid residues 49 to 882 shown in FIG. 5 (disregarding the sequence MNKRIDL, which is not part of the enzyme), or a functional equivalent thereof. The polypeptide of the invention may be used in a method of modifying starch in vitro, comprising treating starch under suitable conditions (e.g. appropriate temperature, pH, etc.) with an effective amount of the polypeptide according to the invention.

The term "functional equivalent", as applied herein to amino acid sequences, is intended to encompass amino acid sequences substantially similar to that shown in FIG. 5, such that the polypeptide possesses sufficient activity to complement the branching enzyme mutation in *E. coli* KV 832 cells (described below) and which is active in *E. coli* in the phosphorylation stimulation assay. Typically such functionally equivalent amino acid sequences will preferably possess at least 85%, more preferably at least 90%, and most preferably at least 95% sequence identity with the amino acid sequence of the mature enzyme (i.e. minus leader sequence) shown in FIG. 5. Those skilled in the art will appreciate that conservative substitutions may be made generally throughout the molecule without substantially affecting the activity of the enzyme. Moreover, some non-conservative substitutions may be tolerated, especially in the less highly conserved regions of the molecule. Such substitutions may be made, for example, to modify slightly the activity of the enzyme. The polypeptide may, if desired, include a leader sequence, such as that exemplified by residues 1 to 48 of the amino acid sequence shown in FIG. 5, although other leader sequences and signal peptides and the like are known and may be included.

A portion of the nucleotide sequence of the invention has been introduced into a plant and found to affect the characteristics of the plant. In particular, introduction of the sequence of the invention, operably linked in the antisense orientation to a suitable promoter, was found to reduce the amount of branched starch molecules in the plant. Additionally, it has recently been demonstrated in other experimental systems that "sense suppression" can also occur (i.e. expression of an introduced sequence operably linked in the sense orientation can interfere, by some unknown mechanism, with the expression of the native gene), as described by Matzke & Matzke (1995 Plant Physiol. 107, 679–685). Any one of the methods mentioned by Matzke & Matzke could, in theory, be used to affect the expression in a host of a homologous SBE gene.

It is believed that antisense methods are mainly operable by the production of antisense mRNA which hybridises to the sense mRNA, preventing its translation into functional polypeptide, possibly by causing the hybrid RNA to be degraded (e.g. Sheehy et al., 1988 PNAS 85, 8805–8809; Van der Krol et al., Mol. Gen. Genet. 220, 204–212). Sense suppression also requires homology between the introduced sequence and the target gene, but the exact mechanism is unclear. It is apparent however that, in relation to both antisense and sense suppression, neither a full length nucleotide sequence, nor a "native" sequence is essential. Preferably the "effective portion" used in the method will comprise at least one third of the full length sequence, but by simple trial and error other fragments (smaller or larger) may be found which are functional in altering the characteristics of the plant.

Thus, in a further aspect the invention provides a method of altering the characteristics of a plant, comprising introducing into the plant an effective portion of the sequence of the invention operably linked to a suitable promoter active in the plant. Conveniently the sequence will be linked in the anti-sense orientation to the promoter. Preferably the plant is a potato plant. Conveniently, the characteristic altered relates to the starch content and/or starch composition of the plant (i.e. amount and/or type of starch present in the plant). Preferably the method of altering the characteristics of the plant will also comprise the introduction of one or more further sequences, in addition to an effective portion of the sequence of the invention. The introduced sequence of the invention and the one or more further sequences (which may be sense or antisense sequences) may be operably linked to a single promoter (which would ensure both sequences were transcribed at essentially the same time), or may be operably linked to separate promoters (which may be necessary for optimal expression). Where separate promoters are employed they may be identical to each other or different. Suitable promoters are well known to those skilled in the art and include both constitutive and inducible types. Examples include the CaMV 35S promoter (e.g. single or tandem repeat) and the patatin promoter. Advantageously the promoter will be tissue-specific. Desirably the promoter will cause expression of the operably linked sequence at substantial levels only in the tissue of the plant where starch synthesis and/or starch storage mainly occurs. Thus, for example, where the sequence is introduced into a potato plant, the operably linked promoter may be tuber-specific, such as the patatin promoter.

Desirably, for example, the method will also comprise the introduction of an effective portion of a sequence encoding a class B SBE, operably linked in the antisense orientation to a suitable promoter active in the plant. Desirably the further sequence will comprise an effective portion of the sequence encoding the potato class B SBE molecule. Conveniently the further sequence will comprise an effective portion of the sequence described by Blennow & Johansson (1991 Phytochem. 30, 437–444) or that disclosed in WO92/11375. More preferably, the further sequence will comprise at least an effective portion of the sequence disclosed in International Patent Application No. WO 95/26407. Use of antisense sequences against both class A and class B SBE in combination has now been found by the present inventors to result in the production of starch having very greatly altered properties (see below). Those skilled in the art will appreciate the possibility that, if the plant already comprises a sense or antisense sequence which efficiently inhibits the class B SBE activity, introduction of a sense or antisense sequence to inhibit class A SBE activity (thereby producing a plant with inhibition of both class A and class B activity) might alter greatly the properties of the starch in the plant, without the need for introduction of one or more further sequences. Thus the sequence of the invention is conveniently introduced into plants already having low levels of class A and/or class B SBE activity, such that the inhibition resulting from the introduction of the sequence of the invention is likely to have a more pronounced effect.

The sequence of the invention, and the one or more further sequences if desired, can be introduced into the plant by any one of a number of well-known techniques (e.g. Agrobacterium-mediated transformation, or by "biolistic" methods). The sequences are likely to be most effective in inhibiting SBE activity in potato plants, but theoretically could be introduced into any plant. Desirable examples include pea, tomato, maize, wheat, rice, barley, sweet potato and cassava plants. Preferably the plant will comprise a natural gene encoding an SBE molecule which exhibits reasonable homology with the introduced nucleic acid sequence of the invention.

In another aspect, the invention provides a plant cell, or a plant or the progeny thereof, which has been altered by the method defined above. The progeny of the altered plant may be obtained, for example, by vegetative propagation, or by crossing the altered plant and reserving the seed so obtained. The invention also provides parts of the altered plant, such as storage organs. Conveniently, for example, the invention provides tubers comprising altered starch, said tubers being obtained from an altered plant or the progeny thereof. Potato tubers obtained from altered plants (or the progeny thereof) will be particularly useful materials in certain industrial applications and for the preparation and/or processing of foodstuffs and may be used, for example, to prepare low-fat waffles and chips (amylose generally being used as a coating to prevent fat uptake), and to prepare mashed potato (especially "instant" mashed potato) having particular characteristics.

In particular relation to potato plants, the invention provides a potato plant or part thereof which, in its wild type possesses an effective SBE A gene, but which plant has been altered such that there is no effective expression of an SBE A polypeptide within the cells of at least part of the plant. The plant may have been altered by the method defined above, or may have been selected by conventional breeding to be deleted for the class A SBE gene, presence or absence of which can be readily determined by screening samples of the plants with a nucleic acid probe or antibody specific for the potato class A gene or gene product respectively.

The invention also provides starch extracted from a plant altered by the method defined above, or the progeny of such a plant, the starch having altered properties compared to starch extracted from equivalent. but unaltered, plants. The invention further provides a method of making altered starch, comprising altering a plant by the method defined above and extracting therefrom starch having altered properties compared to starch extracted from equivalent, but unaltered, plants. Use of nucleotide sequences in accordance with the invention has allowed the present inventors to produce potato starches having a wide variety of novel properties.

In particular the invention provides the following: a plant (especially a potato plant) altered by the method defined above, containing starch which, when extracted from the plant, has an elevated endotherm peak temperature as judged by DSC, compared to starch extracted from a similar, but unaltered, plant; a plant (especially a potato plant) altered by the method defined above, containing starch which, when extracted from the plant, has an elevated viscosity onset temperature (conveniently elevated by 10–25° C.) as judged by viscoamylograph compared to starch extracted from a similar, but unaltered, plant; a plant (especially a potato plant) altered by the method defined above, containing starch which, when extracted from the plant. has a decreased peak viscosity (conveniently decreased by 240–700 SNUs) as judged by viscoamylograph compared to starch extracted from a similar, but unaltered, plant; a plant (especially a potato plant) altered by the method defined above, containing starch which, when extracted from the plant, has an increased pasting viscosity (conveniently increased by 37–260 SNUs) as judged by viscoamylograph compared to starch extracted from a similar, but unaltered, plant; a plant (especially a potato plant) altered by the method defined above, containing starch which, when extracted from the plant, has an increased set-back viscosity (conveniently increased by 224–313 SNUs) as judged by viscoamylograph compared to starch extracted from a similar, but unaltered, plant; a plant (especially a potato plant) altered by the method defined above, containing starch which, when extracted from the plant, has a decreased set-back viscosity as judged by viscoamylograph compared to starch extracted from a similar, but unaltered, plant; and a plant (especially a potato plant) altered by the method defined above, containing starch which, when extracted from the plant, has an elevated amylose content as judged by iodometric assay (i.e. by the method of Morrison & Laignelet 1983, cited above) compared to starch extracted from a similar, but unaltered, plant. The invention also provides for starch obtainable or obtained from such plants as aforesaid.

In particular the invention provides for starch which, as extracted from a potato plant by wet milling at ambient temperature, has one or more of the following properties, as judged by viscoamylograph analysis performed according to the conditions defined below: viscosity onset temperature in the range 70–95° C. (preferably 75–95° C.); peak viscosity in the range 500–12 stirring number units; pasting viscosity in the range 214–434 stirring number units; set-back viscosity in the range 450–618 or 14–192 stirring number units; or displays no significant increase in viscosity during viscoamylograph. Peak, pasting and set-back viscosities are defined below. Viscosity onset temperature is the temperature at which there is a sudden, marked increase in viscosity from baseline levels during viscoamylograph, and is a term well-known to those skilled in the art.

In other particular embodiments, the invention provides starch which as extracted from a potato plant by wet milling at ambient temperature has a peak viscosity in the range 200–500 SNUs and a set-back viscosity in the range 275–618 SNUs as judged by viscoamylograph according to the protocol defined below; and starch which as extracted from a potato plant by wet milling at ambient temperature has a viscosity which does not decrease between the start of the heating phase (step 2) and the start of the final holding phase (step 5) and has a set-back viscosity of 303 SNUs or less as judged by viscoamylograph according to the protocol defined below.

For the purposes of the present invention, viscoamylograph conditions are understood to pertain to analysis of a 10% (w/w) aqueous suspension of starch at atmospheric pressure, using a Newport Scientific Rapid Visco Analyser with a heating profile of: holding at 50° C. for 2 minutes (step 1), heating from 50 to 95° C. at a rate of 1.5° C. per minute (step 2), holding at 95° C. for 15 minutes (step 3), cooling from 95 to 50° C. at a rate of 1.5° C. per minute (step 4), and then holding at 50° C. for 15 minutes (step 5). Peak viscosity may be defined for present purposes as the maximum viscosity attained during the heating phase (step 2) or the holding phase (step 3) of the viscoamylograph. Pasting viscosity may be defined as the viscosity attained by the starch suspensions at the end of the holding phase (step 3) of the viscoamylograph. Set-back viscosity may be defined as the viscosity of the starch suspension at the end of step 5 of the viscoamylograph.

In yet another aspect the invention provides starch from a potato plant having an apparent amylose content (% w/w) of at least 35%, as judged by iodometric assay according to the method described by Morrison & Laignelet (1983 J. Cereal Science 1, 9–20). The iodometric assay is conducted by dissolving the starch in urea-dimethylsuphoxide ("UDMSO"), and aliquots of the solution are used to determine total amylose (measured on lipid-free starch, precipitated from urea-dimethylsulphoxide solution with ethanol). UDMSO may be obtained by mixing 9 volumes of dimethylsulphoxide with 1 volume of 6-M urea. Aliquots of the starch-UDMSO solution are then treated with $I_2$—KI reagent (2 mg $I_2$, 20 mg KI/ml) at different concentrations at constant temperature and followed via colorimetry in order to determine the Blue Value. The Blue Value is defined as the absorbance/cm at 635 nm of 10 mg anhydrous starch in 100 ml dilute $I_2$—KI solution at 20° C. Amylose content is calculated from the Blue Value according to the regression equation: amylose (%)=(28.414×Blue Value)−6.218. Preferably the starch will have an amylose content of at least 40%, more preferably at least 50%, and most preferably at least 66%. Starch obtained directly from a potato plant and having such properties has not hitherto been produced. Indeed, as a result of the present invention, it is now possible to generate in vivo potato starch which has some properties analogous to the very high amylose starches (e.g. HYLON® VII starch) obtainable from maize.

Starches with high (at least 35%) amylose contents find commercial application as, amongst other reasons, the amylose component of starch reassociates more strongly and rapidly than the amylopectin component during retrogradation processes. This may result, for example, in pastes with higher viscosities, gels of greater cohesion, or films of greater strength for starches with high (at least 35%) compared with normal (less than 35%) amylose contents. Alternatively, starches may be obtained with very high amylose contents, such that the granule structure is substantially preserved during heating, resulting in starch suspensions which demonstrate substantially no increase in viscosity during cooking (i.e. there is no significant viscosity increase during viscoamylograph conditions defined above). Such starches typically exhibit a viscosity increase of less than 10% (preferably less than 5%) during viscoamylograph under the conditions defined above.

In commerce, these valuable properties are currently obtained from starches of high amylose content derived from maize plants. It would be of commercial value to have an alternative source of high amylose starches from potato as other characteristics such as granule size, organoleptic properties and textural qualities may distinguish application performances of high amylose starches from maize and potato plants.

Thus high amylose starch obtained by the method of the present invention may find application in many different technological fields, which may be broadly categorised into two groups: food products and processing; and "Industrial" applications. Under the heading of food products, the novel starches of the present invention may find application as, for example, films, barriers, coatings or gelling agents. In general, high amylose content starches absorb less fat during frying than starches with low amylose content, thus the high amylose content starches of the invention may be advantageously used in preparing low fat fried products (e.g. potato chips, crisps and the like). The novel starches may also be employed with advantage in preparing confectionery and in granular and retrograded "resistant" starches. "Resistant" starch is starch which is resistant to digestion by α-amylase. As such, resistant starch is not digested by α-amylases present in the human small intestine, but passes into the colon where it exhibits properties similar to soluble and insoluble dietary fibre. Resistant starch is thus of great benefit in foodstuffs due to its low calorific value and its high dietary fibre content. Resistant starch is formed by the retrogradation (akin to recrystallization) of amylose from starch gels. Such retrogradation is inhibited by amylopectin. Accordingly, the high amylose starches of the present invention are excellent starting materials for the preparation of resistant starch. Suitable methods for the preparation of resistant starch are well-known to those skilled in the art and include, for example, those described in U.S. Pat. Nos. 5,051,271 and 5,281,276. Conveniently the resistant starches provided by the present invention comprise at least 5% total dietary fibre, as judged by the method of Prosky et al., (1985 J. Assoc. Off. Anal. Chem. 68, 677), mentioned in U.S. Pat. No. 5,281, 276.

Under the heading of "Industrial" applications, the novel starches of the invention may be advantageously employed, for example, in corrugating adhesives, in biodegradable products such as loose fill packaging and foamed shapes, and in the production of glass fibers and textiles.

Those skilled in the art will appreciate that the novel starches of the invention may, if desired, be subjected in vitro to conventional enzymatic, physical and/or chemical modification, such as cross-linking, introduction of hydrophobic groups (e.g. octenyl succinic acid, dodecyl succinic acid), or derivatization (e.g. by means of esterification or etherification).

In yet another aspect the invention provides high (35% or more) amylose starches which generate paste viscosities greater than those obtained from high amylose starches from maize plants after processing at temperatures below 100° C. This provides the advantage of more economical starch gelatinization and pasting treatments through the use of lower processing temperatures than are currently required for high amylose starches from maize plants.

The invention will now be further described by way of illustrative example and with reference to the drawings, of which:

FIG. 4a shows the amino acid alignment of the C-terminal portion of starch branching enzyme isoforms from various sources; amino acid residues matching the consensus sequence are shaded;

FIG. 4b shows the alignment of DNA sequences of various starch branching enzyme isoforms which encode a conserved amino acid sequence;

FIG. 5 shows the DNA sequence (Seq ID No. 14) and predicted amino acid sequence (Seq ID No. 15) of a full length potato class A SBE cDNA clone obtained by PCR;

FIG. 6 shows a comparison of the most highly conserved part of the amino acid sequences of potato class A (uppermost sequence) and class B (lowermost sequence) SBE molecules;

FIG. 7 shows a comparison of the amino acid sequence of the full length potato class A (uppermost sequence) and pea (lowermost sequence) class A SBE molecules;

FIG. 8 shows a DNA alignment of various full length potato class A SBE clones obtained by the inventors;

FIG. 9 shows the DNA sequence of a potato class A SBE clone determined by direct sequencing of PCR products, together with the predicted amino acid sequence;

FIG. 10 is a multiple DNA alignment of various full length potato SBE A clones obtained by the inventors;

FIG. 12 shows the DNA sequence and predicted amino acid sequence of the full length potato class A SBE clone as present in the plasmid pSJ90.

EXAMPLES

Figure 1:
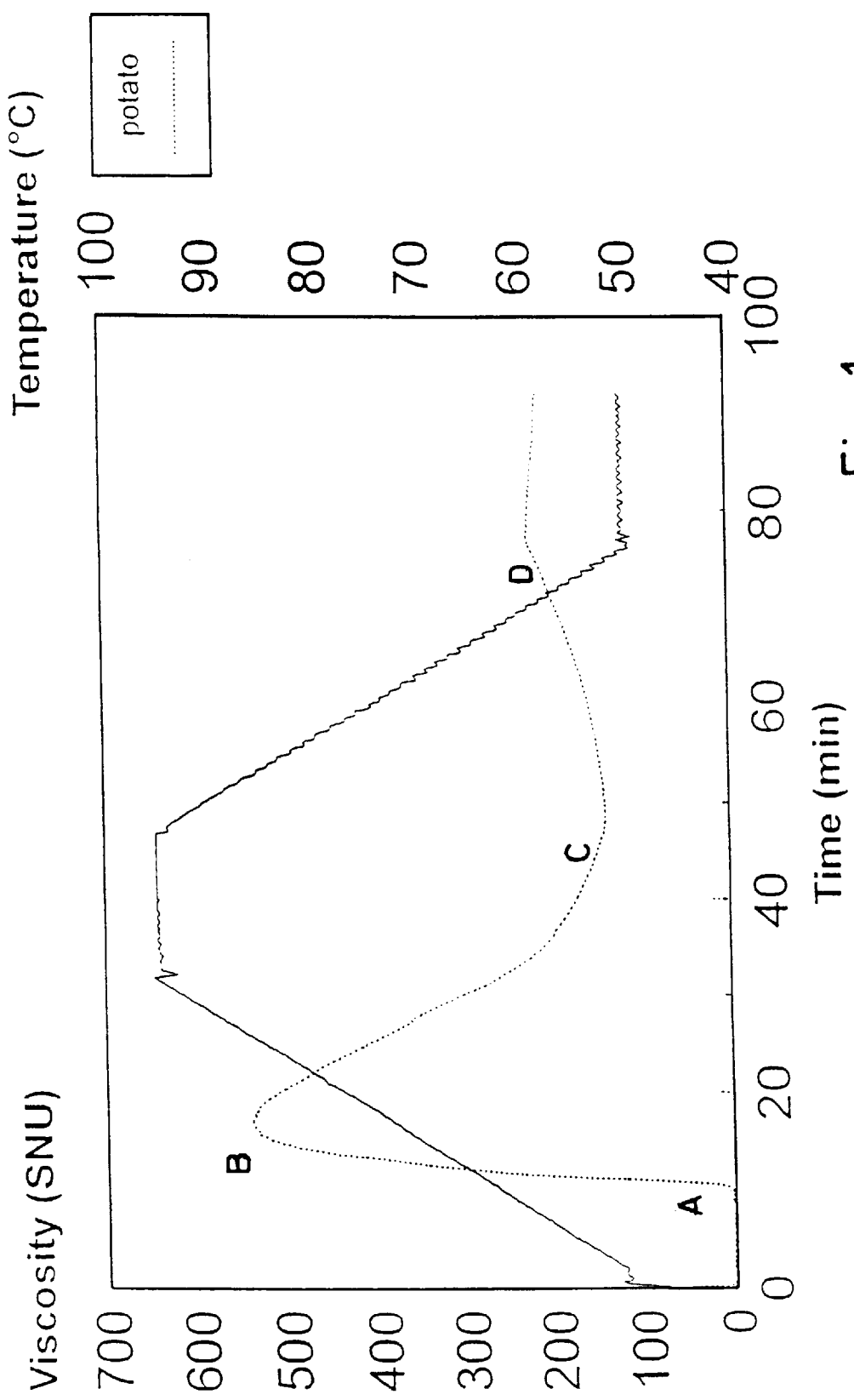
FIG. 1 shows a typical viscoamylograph for a 10% w/w suspension of potato starch.

Prosky Method for Determining Dietary Fiber in Foods According to Prosky, et al., J. Assoc. Off.

Anal. Chem., 68, 677 (1985)

Reagents:

(a) Ethanol 95% v/v, technical grade.
(b) Ethanol 78%. Place 207 ml water into a 1 L volume flask. Dilute to volume with 95% EtOH. Mix and dilute to volume again with 95% EtOH if necessary. Mix
(c) Acetone, reagent grade.
(d) Phosphate buffer, 0.05M, pH 6.0. Dissolve 0.875 g Na phosphate dibasic, anhydride ($Na_2HPO_4$) (or 1.097 g dihydrate) and 6.05 g Na phosphate monobasic monohydrate ($NaH_2PO_4$) (or 6.84 g dihydrate) in a ca 700 ml $H_2O$. Dilute to 1 L with $H_2O$. Check pH with pH meter.
(e) Termamyl (heat stable .alpha.-amylase) solution—No. 120 L, Novo Laboratories, Inc., Wilton Conn. 06897. Keep refrigerated.
(f) Protease. No. P-5380, Sigma Chemical Company. Keep refrigerated.
(g) Amyloglucosidase. No. A-9268, Sigma Chemical Company. Keep refrigerated. Alternatively, a kit containing all 3 enzymes (pretested) is available from Sigma Chemical Company, Catalog No. KR-185.
(h) Sodium hydroxide solution, 0.171N. Dissolve 6.84 g NaOH ACS in ca 700 ml water in 1 L. volume flask. Dilute to volume with water.
(i) Phosphoric acid solution, 0.205M. Dissolve 23.64 g $H_3PO_4$ ACS (85%) in water in 1 L volume flask. Dilute to volume with water.
(j) Celite C-211, acid-washed. Fisher Scientific Company.

Method

Run blank through entire procedure along with samples to measure any contribution from reagents to residue. Homogenize sample and dry overnight in 70° C. vacuum oven, cool in desiccator, and dry-mill portion of sample to 0.3–0.5 mm mesh. Weigh duplicate 1 g samples, accurate to 0.1 mg, into 400 ml, tall-form beakers. Sample weights should not differ by>20 mg. Add 50 ml pH 6.0 phosphate buffer to each beaker. Check pH and adjust if necessary. Add 0.1 ml Termanyl solution. Cover beaker with Aluminum foil and place in boiling water bath 15 minutes. Shake gently at 5 minute intervals. Increase incubation time when number of beakers in boiling water bath makes it difficult for beaker contents to reach internal temperature of 100° C. Use thermometer to ascertain that 100° is attained at 15 minutes. Total of 30 minutes in water bath should be sufficient. Cool solutions to room temperature. Adjust to pH 7.5.+−.0.1 by adding 10 ml 0.171N NaOH solution. Add 5 mg protease. (Protease sticks to spatula, so it may be preferable to prepare enzyme solution just before use with ca 0.1 ml phosphate buffer and pipet required amount).

Cover beaker with aluminum foil. Incubate 30 minutes at 60° C. with continuous agitation. Cool. Add 10 ml 0.205M $H_3PO_4$ solution to adjust pH to 4.5.+−.0.2. Add 0.3 ml amyloglucosidase, cover with aluminum foil and incubate 30 minutes at 60.degree. C. (Measure volume before heating.) Let precipitate form at room temperature for 60 minutes. Weigh crucible containing Celite to nearest 0.1 mg, then wet and redistribute bed of Celite in crucible by using stream of 78% EtOH from wash bottle. Apply suction to draw Celite onto fritted glass as even mat. Maintain suction and quantitatively transfer precipitate from enzyme digest to crucible. Wash residue successively with three 20 ml portions of 78% EtOH, two 10 ml portions of 95% EtOH, and two 10 ml portions of acetone. Gum may form with some samples, trapping liquid. If so, break surface film with spatula to improve filtration. Time for filtration and washing will vary from 0.1–6 hours, averaging 1.2 hour per sample. Long filtration times can be avoided by careful intermittent suction throughout filtration.

Dry crucible containing residue overnight in 70° C. vacuum oven or 105° C. air oven. Cool in desiccator and weigh to nearest 0.1 mg. Subtract crucible and Celite weight to determine weight of residue. Analyze residue from sample of set of duplicates for protein and ash. Subtract protein and ash values from residue to obtain TDF.

Determination of Blank

Blank=(mg blank residue−(% protein in blank+% ash in blank)× mg blank residue)/100 Determination of TDF (%):

TDF%-mg residue−[((%protein in residue+% ash in residue)×mg residue)−blank)×100/(mg sample (wt))]

EXAMPLE 1

Cloning of Potato Class A SBE

Figure 3:
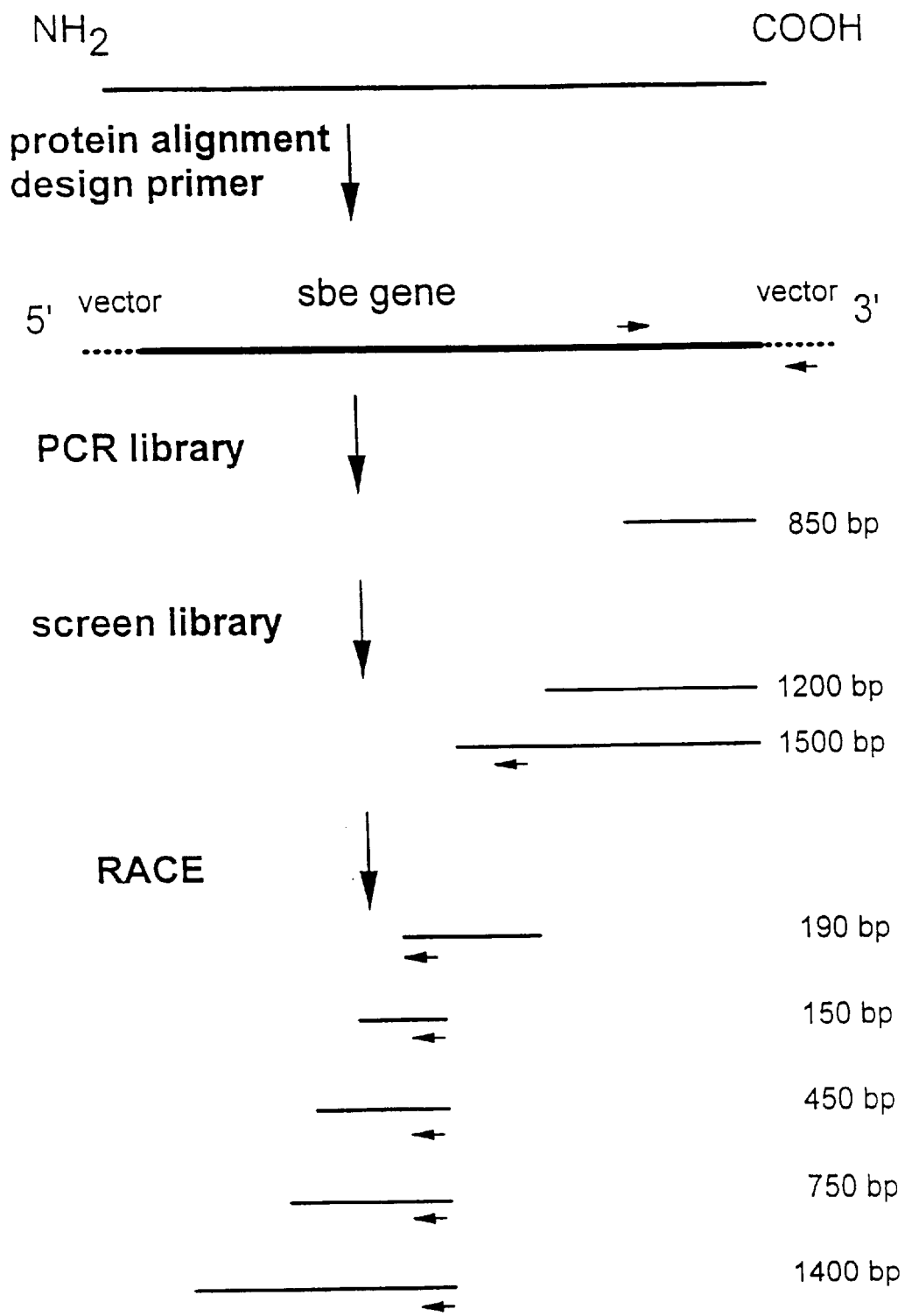
FIG. 3 is a schematic representation of the cloning strategy used by the present inventors.
Figure 4A:
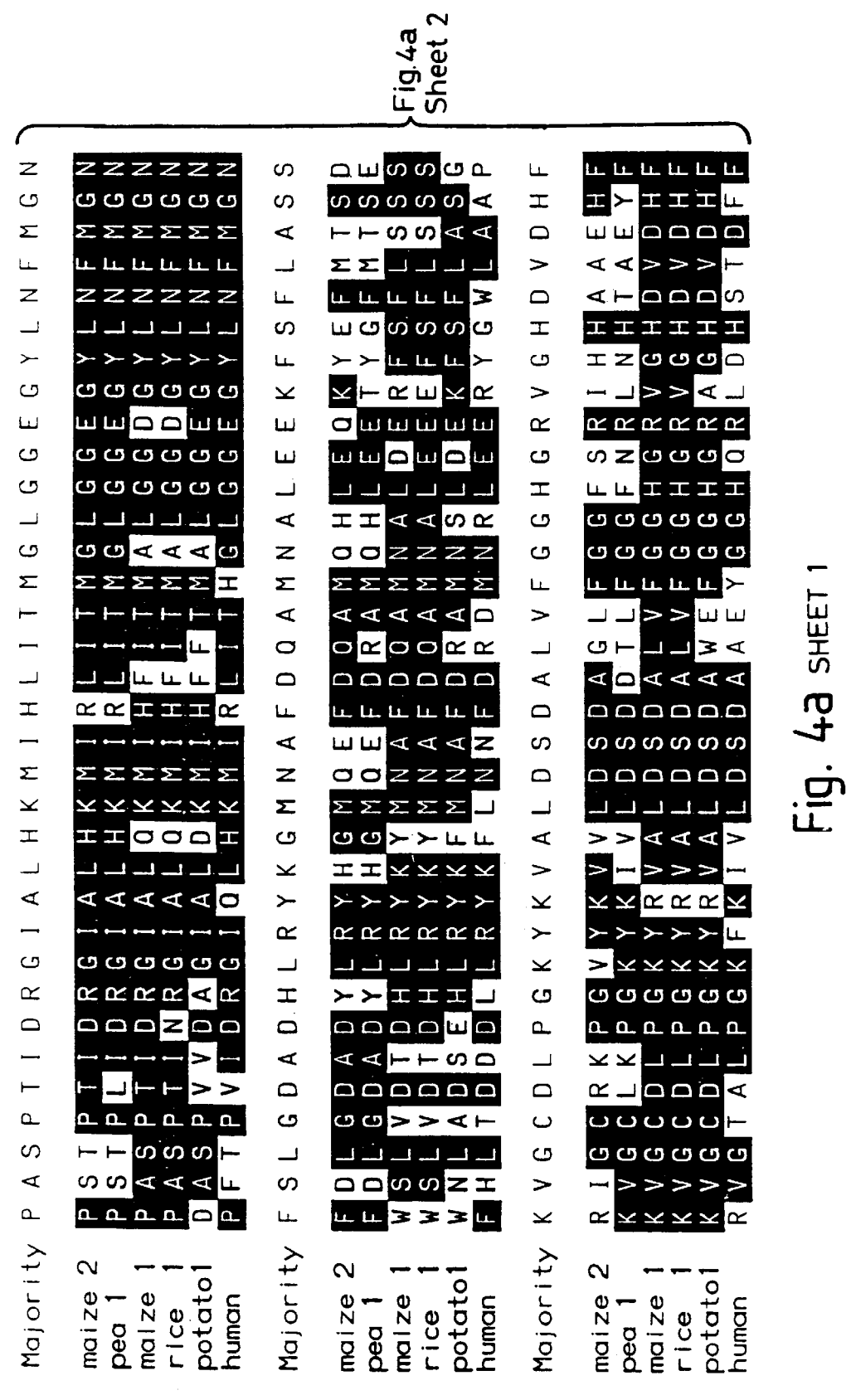
Figure 4A:
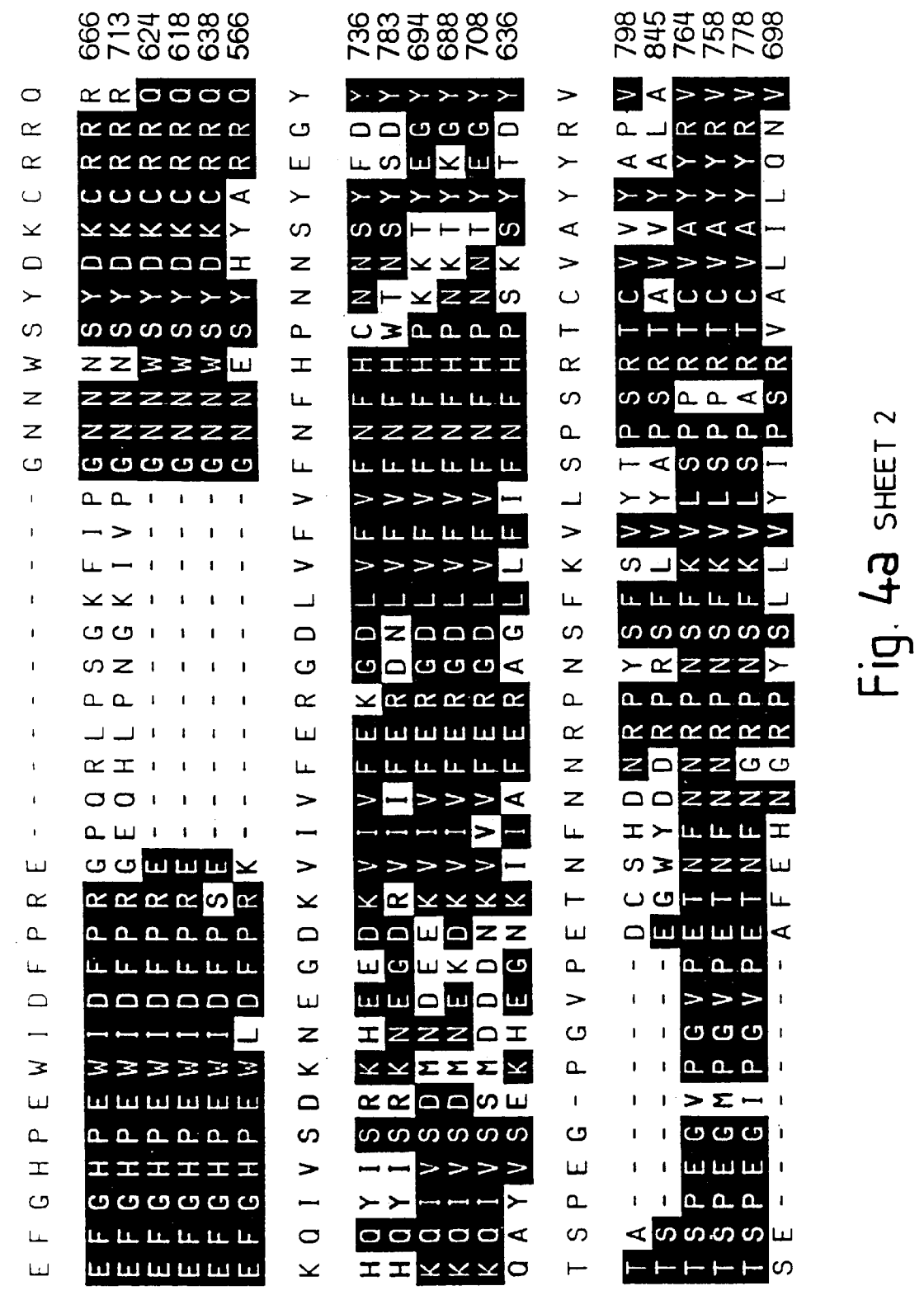
Figure 4B:
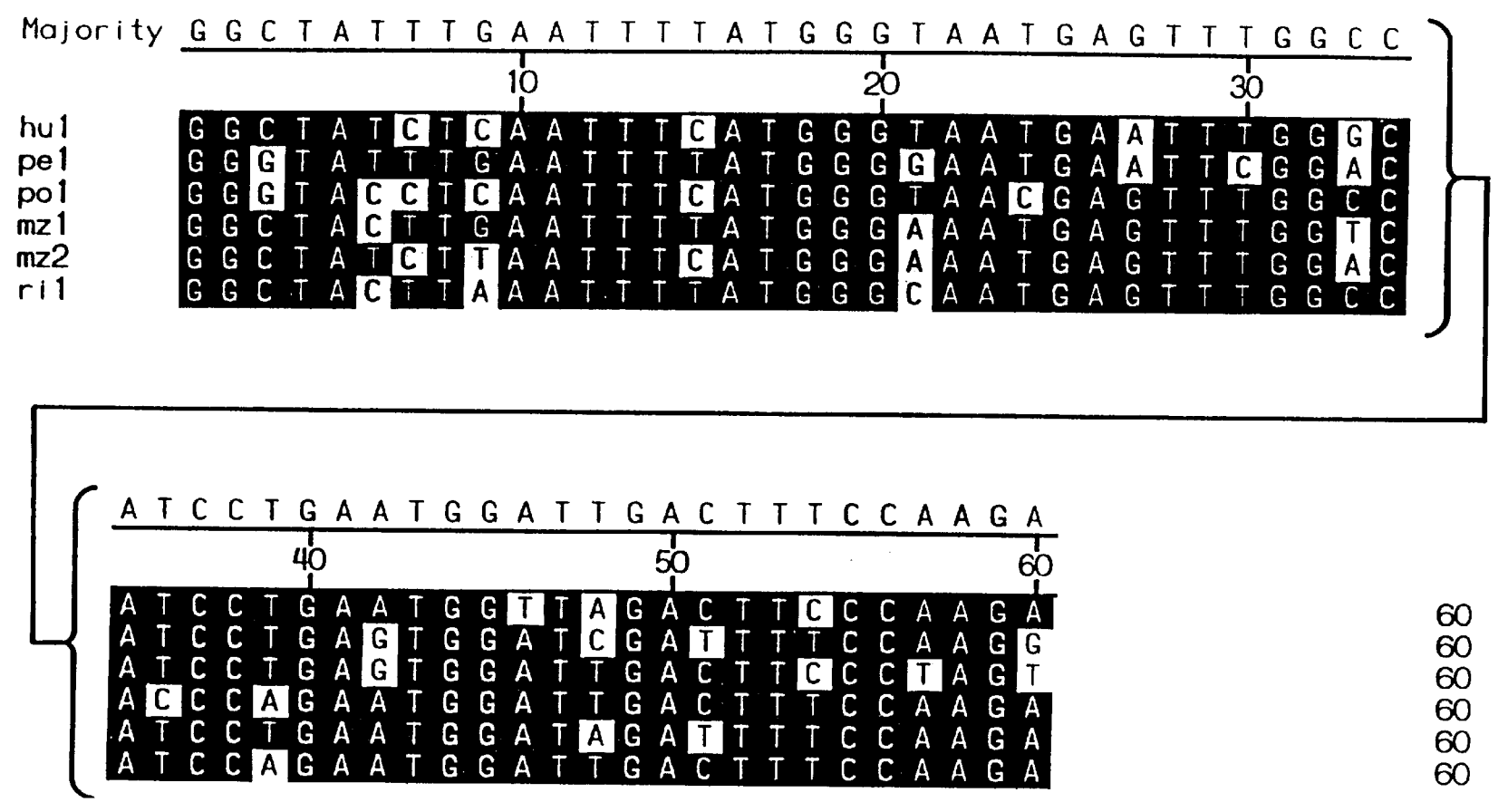

The strategy for cloning the second form of starch branching enzyme from potato is shown in FIG. 3. The small arrowheads represent primers used by the inventors in PCR and RACE protocols. The approximate size of the fragments isolated is indicated by the numerals on the right of the Figure. By way of explanation, a comparison of the amino acid sequences of several cloned plant starch branching enzymes (SBE) from maize (class A), pea (class A), maize (class B), rice (class B) and potato (class B), as well as human glycogen branching enzyme, allowed the inventors to identify a region in the carboxy-terminal one third of the protein which is almost completely conserved (GYLNFMGNEFGHPEWIDFPR) (FIG. 4a). A multiple alignment of the DNA sequences (human, pea class A, potato class B, maize class B, maize class A and rice class B, respectively) corresponding to this region is shown in FIG. 4b and was used to design an oligo which would potentially hybridize to all known plant starch branching enzymes: AATTT(C/T)ATGGGIAA(C/T)GA(A/G)TT(C/T)GG (Seq ID No. 20).

Library PCR

The initial isolation of a partial potato class A SBE cDNA clone was from an amplified potato tuber cDNA library in the λZap vector (Stratagene). One half μL of a potato cDNA library (titre 2.3×10⁹pfu/mL) was used as template in a 50 μL reaction containing 100 pmol of a 16 fold degenerate POTSBE primer and 25 pmol of a T7 primer (present in the λZap vector 3' to the cDNA sequences—see FIG. 3), 100 μM dNTPs, 2.5 U Taq polymerase and the buffer supplied with the Taq polymerase (Stratagene). All components except the enzyme were added to a 0.5 mL microcentrifuge tube, covered with mineral oil and incubated at 94° C. for 7 minutes and then held at 55° C., while the Taq polymerase was added and mixed by pipetting. PCR was then performed by incubating for 1 min at 94° C., 1 min at 58° C. and 3 minutes at 72° C., for 35 cycles. The PCR products were extracted with phenol/chloroform, ethanol precipitated and resuspended in TE pH 8.0 before cloning into the T/A cloning vector pT7BlueR (Invitrogen).

Several fragments between 600 and 1300 bp were amplified. These were isolated from an agarose gel and cloned into the pT7BlueR T/A cloning vector. Restriction mapping of 24 randomly selected clones showed that they belonged to several different groups (based on size and presence/absence of restriction sites). Initially four clones were chosen for sequencing. Of these four, two were found to correspond to the known potato class B SBE sequence, however the other two, although homologous, differed significantly and were more similar to the pea class A SBE sequence, suggesting that they belonged to the class A family of branching enzymes (Burton et al., 1995 The Plant Journal, cited above). The latter two clones (~800bp) were sequenced fully. They both contained at the 5' end the sequence corresponding to the degenerate oligonucleotide used in the PCR and had a predicted open reading frame of 192 amino acids. The deduced amino acid sequence was highly homologous to that of the pea class A SBE.

The ~800 bp PCR derived cDNA fragment (corresponding to nucleotides 2281 to 3076 of the psbe2 con.seq sequence shown in FIG. 8) was used as a probe to screen the potato tuber cDNA library. From one hundred and eighty thousand plaques, seven positives were obtained in the primary screen. PCR analysis showed that five of these clones were smaller than the original 800 bp cDNA clone, so these were not analysed further. The two other clones (designated 3.2.1 and 3.1.1) were approximately 1200 and 1500 bp in length respectively. These were sequenced from their 5' ends and the combined consensus sequence aligned with the sequence from the PCR generated clones. The cDNA clone 3.2.1 was excised from the phage vector and plasmid DNA was prepared and the insert fully sequenced. Several attempts to obtain longer clones from the library were unsuccessful, therefore clones containing the 5' end of the full length gene were obtained using RACE (rapid amplification of cDNA ends).

Rapid Amplification of cDNA Ends (RACE) and PCR Conditions

RACE was performed essentially according to Frohman (1992 Amplifications 11–15). Two μg of total RNA from mature potato tubers was heated to 65° C. for 5 min and quick cooled on ice. The RNA was then reverse transcribed in a 20 μL reaction for 1 hour at 37° C. using BRL's M-MLV reverse transcriptase and buffer with 1 mM DTT, 1 mM dNTPs, 1 U/μL RNAsin (Promega) and 500 pmol random hexamers (Pharmacia) as primer. Excess primers were removed on a Centricon 100 column and cDNA was recovered and precipitated with isopropanol. cDNA was A-tailed in a volume of 20 μl using 10 units terminal transferase (BRL), 200 μM dATP for 10 min at 37° C., followed by 5 min at 65° C. The reaction was then diluted to 0.5 ml wi TE pH 8 and stored at 4° C. as the cDNA pool. cDNA clones were isolated by PCR amplification using the primers $R_oR_1dT_{17}$, $R_o$ and POTSBE24. The PCR was performed in 50 μL using a hot start technique: 10 μL of the cDNA pool was heated to 94° C. in water for 5 min with 25 pmol POTSBE24, 25 pmol $R_o$ and 2.5 pmol of $R_oR_1dT_{17}$ and cooled to 75° C. Five μL of 10 ×PCR buffer (Stratagene), 200 μM dNTPs and 1.25 units of Taq polymerase were added, the mixture heated at 45° C. for 2 min and 72° C. for 40 min followed by 35 cycles of 94° C. for 45 sec, 50° C. for 25 sec, 72° C. for 1.5 min and a final incubation at 72° C. for 10 min. PCR products were separated by electrophoresis on 1% low melting agarose gels and the smear covering the range 600–800 bp fragments was excised and used in a second PCR amplification with 25 pmol of $R_1$ and POTSBE25 primers in a 50 μL reaction (28 cycles of 94° C. for 1 min, 50° C. 1 min, 72° C. 2 min). Products were purified by chloroform extraction and cloned into pT7 Blue. PCR was used to screen the colonies and the longest clones were sequenced.

The first round of RACE only extended the length of the SBE sequence approximately 100 bases, therefore a new A-tailed cDNA library was constructed using the class A SBE specific oligo POTSBE24 (10 pmol) in an attempt to recover longer RACE products. The first and second round PCR reactions were performed using new class A SBE primers (POTSBE 28 and 29 respectively) derived from the new sequence data. Conditions were as before except that the elongation step in the first PCR was for 3 min and the second PCR consisted of 28 cycles at 94° C. for 45 seconds, 55° C. for 25 sec and 72° C. for 1 min 45 sec.

Clones ranging in size from 400 bp to 1.4 kb were isolated and sequenced. The combined sequence of the longest RACE products and cDNA clones predicted a full length gene of about 3150 nucleotides, excluding the poly(A) tail (psbe 2con.seq in FIG. 8).

As the sequence of the 5' half of the gene was compiled from the sequence of several RACE products generated using Taq polymerase, it was possible that the compiled sequence did not represent that of a single mRNA species and/or had nucleotide sequence changes. The 5' 1600 bases of the gene was therefore re-isolated by PCR using Ultma, a thermostable DNA polymerase which, because it possesses a 3'–5' exonuclease activity, has a lower error rate compared to Taq polymerase. Several PCR products were cloned and restriction mapped and found to differ in the number of Hind III, Ssp I, and EcoR I sites. These differences do not represent PCR artefacts as they were observed in clones obtained from independent PCR reactions (data not shown) and indicate that there are several forms of the class A SBE gene transcribed in potato tubers.

In order to ensure that the sequence of the full length cDNA clone was derived from a single mRNA species it was therefore necessary to PCR the entire gene in one piece. cDNA was prepared according to the RACE protocol except that the adaptor oligo $R_oR_1dT_{17}$ (5 pmol) was used as a primer and after synthesis the reaction was diluted to 200 μL with TE pH 8 and stored at 4° C. Two μL of the cDNA was used in a PCR reaction of 50 μL using 25 pmol of class A SBE specific primers PBER1 and PBERT (see below), and thirty cycles of 94° for 1 min, 60° C. for 1 min and 72° C. for 3 min. If Taq polymerase was used the PCR products were cloned into pT7Blue whereas if Ultma polymerase was used the PCR products were purified by chloroform extraction, ethanol precipitation and kinased in a volume of 20 µL (and then cloned into pBSSK IIP which had been cut with EcoRV and dephosphorylated). At least four classes of cDNA were isolated, which again differed in the presence or absence of Hind III, Ssp I and EcoR I sites. Three of these clones were sequenced fully, however one clone could not be isolated in sufficient quantity to sequence.

The sequence of one of the clones (number 19) is shown in FIG. 5. The first methionine (initiation) codon starts a short open reading frame (ORF) of 7 amino acids which is out of frame with the next predicted ORF of 882 amino acids which has a molecular mass (Mr) of approximately 100 Kd. Nucleotides 6-2996 correspond to SBE sequence—the rest of the sequence shown is vector derived. FIG. 6 shows a comparison of the most highly conserved part of the amino acid sequence of potato class A SBE (residues 180–871, top, row) and potato class B SBE (bottom row, residues 98–792); the middle row indicates the degree of similarity, identical residues being denoted by the common letter, conservative changes by two dots and neutral changes by a single dot. Dashes indicate gaps introduced to optimise the alignment. The class A SBE protein has 44% identity over the entire length with potato class B SBE, and 56% identity therewith in the central conserved domain (FIG. 6), as judged by the "Megalign" program (DNASTAR). However, FIG. 7 shows a comparison betwteen potato class A SBE (top row, residues 1–873) and pea class A SBE (bottom row, residues 1–861), from which it can be observed that cloned potato gene is more homologous to the class A pea enzyme, where the identity is 70% over nearly the entire length, and this increases to 83% over the central conserved region (starting at IPPP at position ~170). It is clear from this analysis that this cloned potato SBE gene belongs to the class A family of SBE genes.

An *E coli* culture, containing the plasmid pSJ78 (which directs the expression of a full length potato SBE Class A gene), has been deposited (on 3rd Jan. 1996) under the terms of the Budapest Treaty at The National Collections of Industrial and Marine Bacteria Limited (23 St Machar Drive, Aberdeen, AB2 1RY, United Kingdom), under accession number NCIMB 40781. Plasmid pSJ78 is equivalent to clone 19 described above. It represents a full length SBE A cDNA blunt-end ligated into the vector pBSSKIIP.

Polymorphism of Class A SBE Genes

Sequence analysis of the other two full length class A SBE genes showed that they contain frameshift mutations and are therefore unable to encode full length proteins and indeed they were unable to complement the branching enzyme deficiency in the KV832 mutant (described below). An alignment of the full length DNA sequences is shown in FIG. 8: "10con.seq" (Seq ID No. 12), "19con.seq" (Seq ID No. 14) and "11con.seq" (Seq ID No. 13) represent the sequence of full length clones 10, 19 and 11 obtained by PCR using the PBER1 and PBERT primers (see below), whilst "psbe2con.seq" (Seq ID No. 18) represents the consensus sequence of the RACE clones and cDNA clone 3.2.1. Those nucleotides which differ from the overall consensus sequence (not shown) are shaded. Dashes indicate gaps introduced to optimise the alignment. Apart from the frameshift mutations these clones are highly homologous. It should be noted that the 5' sequence of psbe2con is longer because this is the longest RACE product and it also contains several changes compared to the other clones. The upstream methionine codon is still present in this clone but the upstream ORF is shortened to just 3 amino acids and in addition there is a 10 base deletion in the 5' untranslated leader.

The other significant area of variation is in the carboxy terminal region of the protein coding region. Closer examination of this area reveals a GAA trinucleotide repeat structure which varies in length between the four clones. These are typical characteristics of a microsatellite repeat region. The most divergent clone is #11 which has only one GAA triplet whereas clone 19 has eleven perfect repeats and the other two clones have five and seven GAA repeats. All of these deletions maintain the ORF but change the number of glutamic acid residues at the carboxy terminus of the protein.

Most of the other differences between the clones are single base changes. It is quite possible that some of these are PCR errors. To address this question direct sequencing of PCR fragments amplified from first strand cDNA was performed. FIG. 9 shows the DNA sequence, and predicted amino acid sequence, obtained by such direct sequencing. Certain restriction sites are also marked. Nucleotides which could not be unambiguously assigned are indicated using standard 1UPAC notation and, where this uncertainty affects the predicted amino acid sequence, a question mark is used. Sequence at the extreme 5' and 3' ends of the gene could not be determined because of the heterogeneity observed in the different cloned genes in these regions (see previous paragraph). However this can be taken as direct evidence that these differences are real and are not PCR or cloning artefacts.

There is absolutely no evidence for the frameshift mutations in the PCR derived sequence and it would appear that these mutations are an artefact of the cloning process, resulting from negative selection pressure in *E. coli*. This is supported by the fact that it proved extremely difficult to clone the full length PCR products intact as many large deletions were seen and the full length clones obtained were all cloned in one orientation (away from the LacZ promoter), perhaps suggesting that expression of the gene is toxic to the cells. Difficulties of this nature may have been responsible, at least in part, for the previous failure of other researchers to obtain the present invention.

A comparison of all the full length sequences is shown in FIG. 10. In addition to clones 10, 11 and 19 are shown the sequences of a Bgl II—Xho I product cloned directly into the QE32 expression vector ("86CON.SEQ", Seq ID No. 16) and the consensus sequence of the directly sequenced PCR products ("pcrsbe2con.seq", Seq ID No. 17). Those nucleotides which differ from the consensus sequence (not shown) are shaded. Dashes indicate gaps introduced to optimise the alignment. There are 11 nucledtide differences predicted to be present in the mRNA population, which are indicated by asterisks above and below the sequence. The other differences are probably PCR artefacts or possibly sequencing errors.

Complementation of a Branching Enzyme Deficient *E. coli* Mutant

Figure 12:
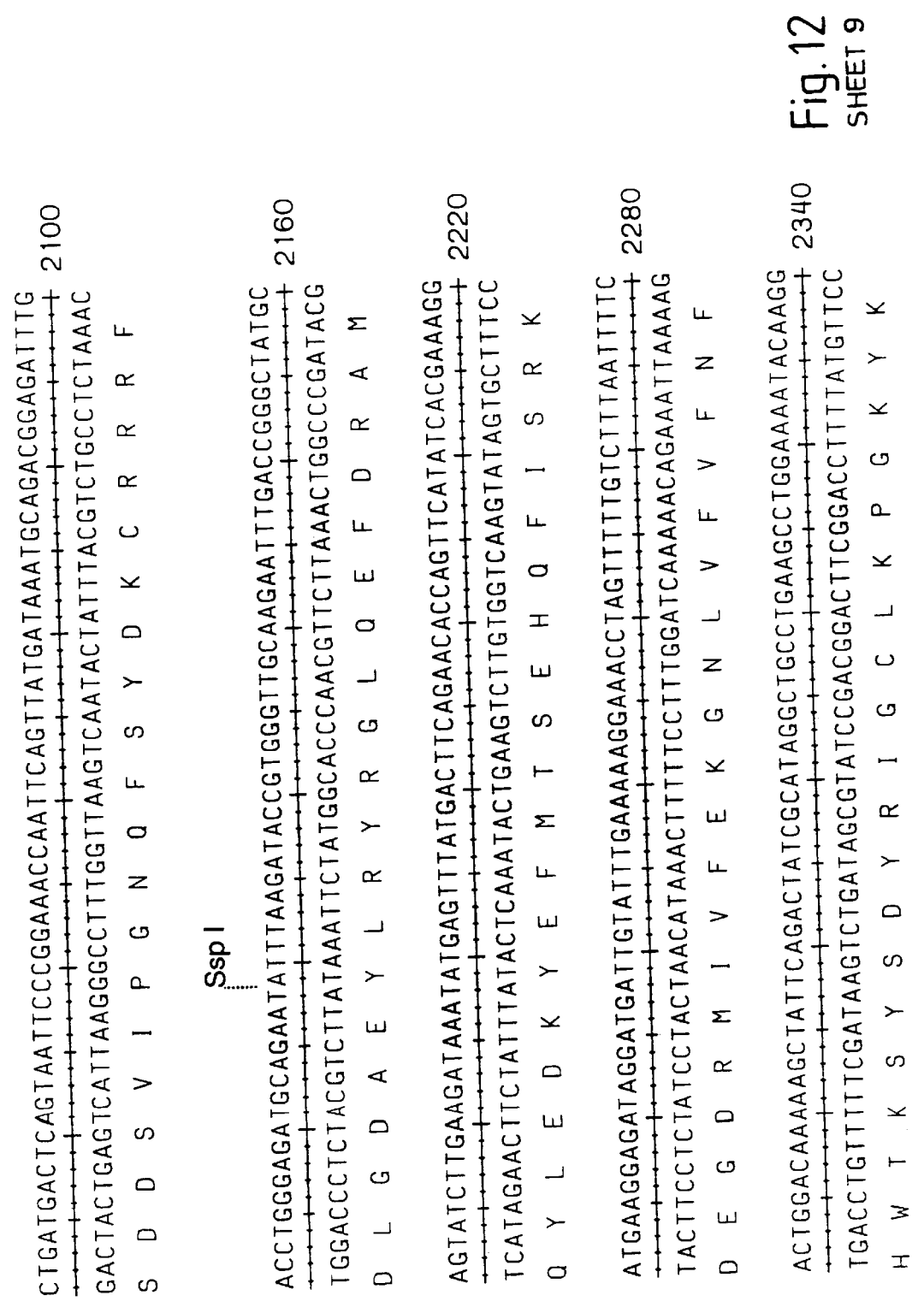

To determine if the isolated SBE gene encodes an active protein i.e. one that has branching enzyme activity, a complementation test was performed in the *E. coli* strain KV832. This strain is unable to make bacterial glycogen as the gene for the glycogen branching enzyme has been deleted (Keil et al., 1987 Mol. Gen. Genet. 207, 294–301). When wild type cells are grown in the presence of glucose they synthesise glycogen (a highly branched glucose polymer) which stains a brown colour with iodine, whereas the KV832 cells make only a linear chain glucose polymer which stains bluish green with iodine. To determine if the cloned SBE gene could restore the ability of the KV832 cells to make a branched polymer, the clone pSJ90 (Seq ID No. 19) was used and constructed as below. The construct is a PCR-derived, substantially full length fragment (made using primers PBE 2B and PBE 2X, detailed below), which was cut with Bgl II and Xho I and cloned into the BamH I/Sal I sites of the His-tag expression vector pQE32 (Qiagen). This clone, pSJ86, was sequenced and found to have a frameshift mutation of two bases in the 5' half of the gene. This frameshift was removed by digestion with Nsi I and SnaB I and replaced with the corresponding fragment from a Taq-generated PCR clone to produce the plasmid pSJ90 (sequence shown in FIG. 12; the first 10 amino acids are derived from the expression vector). The polypeptide encoded by pSJ90 would be predicted to correspond to amino acids 46–882 of the full SBE coding sequence. The construct pSJ90 was transformed into the branching enzyme deficient KV832 cells and transformants were grown on solid PYG medium (0.85% $KH_2PO_4$, 1.1% $K_2HPO_4$, 0.6% yeast extract) containing 1.0% glucose. To test for complementation, a loop of cells was scraped off and resuspended in 150 µl of water, to which was added 15 µl Lugol's solution (2 g KI and 1 g $I_2$ per 300 ml water). It was found that the potato SBE fragment-transformed KV832 cells now stained a yellow-brown colour with iodine whereas control cells containing only the pQE32 vector continued to stain bluegreen.

Expression of Potato Class A SBE in *E. coli*

Single colonies of KV832, containing one of the plasmids pQE32, pAGCR1 or pSJ90, were picked into 50 ml of 2×YT medium containing carbenicillin, kanamycin and streptomycin as appropriate (100, 50 and 25 mg/L, respectively) in a 250 ml flask and grown for 5 hours, with shaking, at 37° C. IPTG was then added to a final concentration of 1 mM to induce expression and the flasks were further incubated overnight at 25° C. The cells were harvested by centrifugation and resuspended in 50 mM sodium phosphate buffer (pH 8.0), containing 300 mM NaCl, 1 mg/ml lysozyme and 1 mM PMSF and left on ice for 1 hour. The cell lysates were then sonicated (3 pulses of 10 seconds at 40% power using a microprobe) and cleared by centrifugation at 12,000 g for 10 minutes at 4° C. Cleared lysates were concentrated approximately 10 fold in a Centricon™ 30 filtration unit. Duplicate 10 µl samples of the resulting extract were assayed for SBE activity by the phosphorylation stimulation method, as described in International Patent Application No. PCT/GB95/00634. In brief, the standard assay reaction mixture (0.2 ml) was 200 mM 2-(N-morpholino) ethanesulphonic acid (MES) buffer pH6.5, containing 100 nCi of $^{14}C$ glucose-1-phosphate at 50 mM, 0.05 mg rabbit phosphorylase A, and *E. coli* lysate. The reaction mixture was incubated for 60 minutes at 30° C. and the reaction terminated and glucan polymer precipitated by the addition of 1 ml of 75% (v/v) methanol, 1% (w/v) potassium hydroxide, and then 0.1 ml glycogen (10 mg/ml). The results are presented below:

| Construct | SBE Activity (cpm) |
|---|---|
| pQE32 (control) | 1,829 |
| pSJ90 (potato class A SBE) | 14,327 |
| pAGCR1 (pea class A SBE) | 29,707 |

The potato class A SBE activity is 7–8 fold above background levels. It was concluded therefore that the potato class A SBE gene was able to complement the BE mutation in the phosphorylation stimulation assay and that the cloned gene does indeed code for a protein with branching enzyme activity.

Oligonucleotides

The following synthetic oligonucleotides (Seq ID No.s 1–11 respectively) were used:

| | |
|---|---|
| $R_OR_IdT_{17}$ | AAGGATCCGTCGACATCGATAATACGACTCACTATAGGGA(T)$_{17}$ |
| $R_O$ | AAGGATCCGTCGACATC |
| $R_I$ | GACATCGATAATACGAC |
| POTSBE24 | CATCCAACCACCATCTCGCA |
| POTSBE25 | TTGAGAGAAGATACCTAAGT |
| POTSBE28 | ATGTTCAGTCCATCTAAAGT |
| POTSBE29 | AGAACAACAATTCCTAGCTC |
| PBER 1 | GGGGCCTTGAACTCAGCAAT |
| PBERT | CGTCCCAGCATTCGACATAA |
| PBE 2B | CTTGGATCCTTGAACTCAGCAATTTG |
| PBE 2X | TAACTCGAGCAACGCGATCACAAGTTCGT |

Example 2

Production of Transgenic Plants

Figure 11:
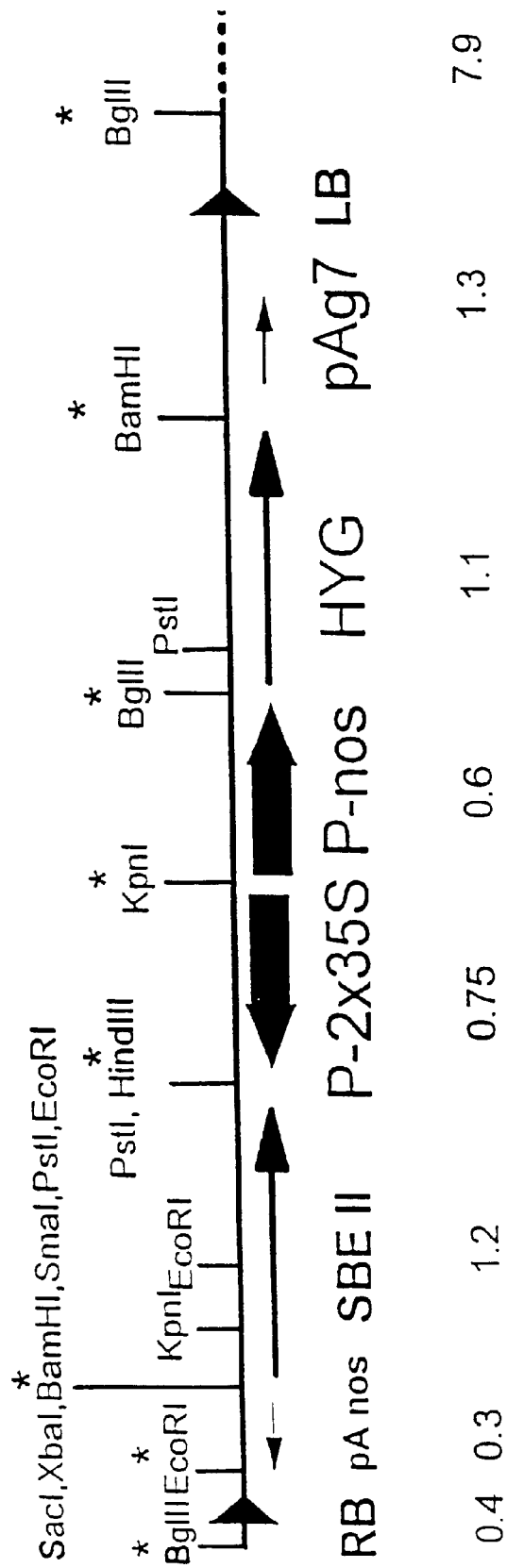
FIG. 11 is a schematic illustration of the plasmid pSJ64.

Construction of Plant Transformation Vectors with Antisense Starch Branching Enzyme Genes A 1200 bp Sac I-Xho I fragment, encoding approximately the —COOH half of the potato class A SBE (isolated from the rescued λZap clone 3.2.1), was cloned into the Sac I-Sal I sites of the plant transformation vector pSJ29 to create plasmid pSJ64, which is illustrated schematically in FIG. 11. In the figure, the black line represents the DNA sequence. The broken line represents the bacterial plasmid backbone (containing the origin of replication and bacterial selection marker), which is not shown in full. The filled triangles on the line denote the T-DNA borders (RB=right border, LB=left border). Relevant restriction sites are shown above the black line, with the approximate distances (in kilobases) between the sites (marked by an asterisk) given by the numerals below the line. The thinnest arrows indicate polyadenylation signals (pAnos=nopaline synthase, pAg7= Agrobacterium gene 7), the arrows intermediate in thickness denote protein coding regions (SBE II=potato class A SBE, HYG=hygromycin resistance gene) and the thickest arrows represent promoter regions (P-2×35 =double CaMV 35S promoter, Pnos=nopaline synthase promoter). Thus pSJ64 contained the class A SBE gene fragment in an antisense orientation between the 2X 35S CaMV promoter and the nopaline synthase polyadenylation signal.

For information, pSJ29 is a derivative of the binary vector pGPTV-HYG (Becker et al., 1992 Plant Molecular Biology 20, 1195–1197) modified as follows: an approximately 750 bp (Sac I, T4 DNA polymerase blunted—Sal I) fragment of pJIT60 (Guerineau et al., 1992 Plant Mol. Biol. 18, 815–818) containing the duplicated cauliflower mosaic virus (CaMV) 35S promoter (Cabb-JI strain, equivalent to nucleotides 7040 to 7376 duplicated upstream of 7040 to 7433, Frank et al., 1980 Cell 21, 285–294) was cloned into the Hind III (Klenow polymerase repaired)—Sal I sites of pGPTV-HYG to create pSJ29.

Plant Transformation

Transformation was conducted on two types of potato plant explants; either wild type untransformed minitubers (in order to give single transformants containing the class A antisense construct alone) or minitubers from three tissue culture lines (which gave rise to plants #12, #15, #17 and #18 indicated in Table 1) which had already been successfully transformed with the class B (SBE I) antisense construct containing the tandem 35S promoter (so as to obtain double transformant plants, containing antisense sequences for both the class A and class B enzymes).

Details of the method of Agrobacterium transformation, and of the growth of transformed plants, are described in International Patent Application No. WO 95/26407, except that the medium used contained 3% sucrose (not 1%) until the final transfer and that the initial incubation with Agrobacterium (strain 3850) was performed in darkness. Transformants containing the class A antisense sequence were selected by growth in medium containing 15 mg/L hygromycin (the class A antisense construct comprising the HYG gene, i.e. hygromycin phosphotransferase).

Transformation was confirmed in all cases by production of a DNA fragment from the antisense gene after PCR in the presence of appropriate primers and a crude extract of genomic DNA from each regenerated shoot.

Characterisation of Starch from Potato Plants

Starch was extracted from plants as follows: potato tubers were homogenised in water for 2 minutes in a Waring blender operating at high speed. The homogenate was washed and filtered (initially through 2 mm, then through 1 mm filters) using about 4 liters of water per 100 gms of tubers (6 extractions). Washed starch granules were finally extracted with acetone and air dried.

Starch extracted from singly transformed potato plants (class A/SBE II antisense, or class B/SBE I antisense), or from double transformants (class A/SBE II and class B/SBE I antisense), or from untransformed control plants, was partially characterised. The results are shown in Table 1. The table shows the amount of SBE activity (units/gram tissue) in tubers from each transformed plant. The endotherm peak temperature (° C.) of starch extracted from several plants was determined by DSC, and the onset temperature (° C) of pasting was determined by reference to a viscoamylograph ("RVA"), as described in WO 95/26407. The viscoamylograph profile was as follows: step 1—50° C. for 2 minutes; step 2—increase in temperature from 50° C. to 95° C. at a rate of 1.5° C. per minute; step 3—holding at 95° C. for 15 minutes; step 4—cooling from 95° C. to 50° C. at a rate of 1.5° C. per minute; and finally, step 5—holding at 50° C. for 15 minutes. Table 1 shows the peak, pasting and set-back viscosities in stirring number units (SNUs), which is a measure of the amount of torque required to stir the suspensions. Peak viscosity may be defined for present purposes as the maximum viscosity attained during the heating phase (step 2) or the holding phase (step 3) of the viscoamylograph. Pasting viscosity may be defined as the viscosity attained by the starch suspensions at the end of the holding phase (step 3) of the viscoamylograph. Set-back viscosity may be defined as the viscosity of the starch suspension at the end of step 5 of the viscoamylograph.

A determination of apparent amylose content (% w/w) was also performed, using the iodometric assay method of Morrison & Laignelet (1983 J. Cereal Sci. 1, 9–20). The results (percentage apparent amylose) are shown in Table 1. The untransformed and transformed control plants gave rise to starches having apparent amylose contents in the range 29(+/−3)%.

Generally similar values for amylose content were obtained for starch extracted from most of the singly transformed plants containing the class A (SBE II) antisense sequence. However, some plants (#152, 249) gave rise to starch having an apparent amylose content of 37–38%, notably higher than the control value. Starch extracted from these plants had markedly elevated pasting onset temperatures, and starch from plant 152 also exhibited an elevated endotherm peak temperature (starch from plant 249 was not tested by DSC).

TABLE 1

| Sample description | Sample. number | Tuber SBE activity (U/g starch) | DSC Peak temperature (° C.) | Viscoamylograph (RVA) Onset temperature (° C.) | Peak viscosity (SNU) | Pasting viscosity (SNU) | Set-back viscosity (SNU) | Apparent amylose content (% w/w) | Phosphorus content (mg/100 g) |
|---|---|---|---|---|---|---|---|---|---|
| Untransformed control | 146 | 7.6 | 65.8 | 65.5 | 545 | 161 | 260 | 31.2 | 68 |
|  | 243 | 22.2 | nd | 62.6 | 761 | 135 | 241 | 29.1 |  |
| AS-Class A SBE | 152 | 12.7 | 69.5 | 70.9 | 467 | 380 | 529 | 37.5 | 89 |
|  | 249 | 13.9 | nd | 70.0 | 497 | 434 | 518 | 38.5 |  |
| AS-Class B SBE (17) (control) | 145 | 0.7 | 66.9 | 66.8 | 669 | 177 | 305 | 29.8 | 111 |
| AS-Class B SBE (17) + AS-Class A SBE | 150 | 0.6 | 74.0 | 86.0 | 214 | 214 | 303 | 53.1 | 198 |
|  | 161 | 0.5 | 73.0 | 76.6 | 349 | 324 | 618 | 40.9 | 206 |
| AS-Class B SBE (18) (control) | 144 | 1.6 | 64.5 | 64.7 | 714 | 154 | 258 | 29.0 | 97 |
| AS-Class B SBE (18) + AS-Class A SBE | 149 | 3.0 | 68.5 | 69.9 | 474 | 267 | 482 | 35.6 | 127 |
| AS-Class B SBE (15) (control) | 172 | 0.22 | nd | 65.4 | 707 | 167 | 290 | 28.8 | 130 |
| AS-Class B SBE (15) + AS-Class A SBE | 201 | 0.10 | nd | >95 | no peak | 12 | 13 | 66.4 | 210 |
|  | 208a | 0.10 | nd | >95 | no peak | 15 | 17 | 64.1 |  |
|  | 208 | 0.30 | 72.8–80.5 | >95 | no peak | 14 | 19 | 62.8 | 240 |
|  | 202 | 0.02 | nd | 89.4 | no peak | 172 | 245 | 57.9 |  |
|  | 212 | 1.40 | nd | 78.0 | 308 | 296 | 541 | 49.5 |  |
|  | 220 | 1.40 | nd | 75.8 | 355 | 345 | 593 | 44.1 |  |
| AS-Class B SBE (12) (control) | 170 | 0.2 | nd | 66.5 | 768 | 202 | 303 | 27.8 |  |
| AS-Class B SBE (12) + AS-Class A SBE | 236 | 0.7 | nd | 95.0 | no peak | 23 | 14 | 60.4 |  |

TABLE 1-continued

| Sample description | Sample number | Tuber SBE activity (U/g starch) | DSC Peak temperature (° C.) | Viscoamylograph (RVA) | | | | |
|---|---|---|---|---|---|---|---|---|
| | | | | Onset temperature (° C.) | Peak viscosity (SNU) | Pasting viscosity (SNU) | Set-back viscosity (SNU) | Apparent amylose content (% w/w) | Phosphorus content (mg/100 g) |
| | 236a | 0.9 | nd | 91.2 | no peak | 139 | 192 | 56.7 | |
| | 230a | 0.8 | nd | 77.6 | 244 | 239 | 450 | 48.2 | |

RVA profile 50° C. (2 min), 50–95° C. (1.5° C./min), 95° C. (15 min), 95–50° C. (1.5° C./min), 50° C. (15 min)
Pasting viscosity (47 min) at end of 50° C. (2 min), 50–95° C. (1.5° C./min), 95° C. (15 min)
Set-back viscosity (92 min) at end of profile
SBE Starch Branching Enzyme
SNU Instrument "Stirring Number Units" (arbitrary units)
nd not determined It should be noted that, even if other single transformants were not to provide starch with an altered amylose/amylopectin ratio, the starch from such plants might still have different properties relative to starch from conventional plants (e.g. different average molecular weight or different amylopectin branching patterns), which might be useful.

Double transformant plants, containing antisense sequences for both the class A and class B enzymes, had greatly reduced SBE activity (units/gm) compared to untransformed plants or single anti-sense class A transformants, (as shown in Table 1). Moreover, certain of the double transformant plants contained starch having very significantly altered properties. For example, starch extracted from plants #201, 202, 208, 208a, 236 and 236a had drastically altered amylose/amylopectin ratios, to the extent that amylose was the main constituent of starch from these plants. The pasting onset temperatures of starch from these plants were also the most greatly increased (by about 25–30° C.). Starch from plants such as #150, 161, 212, 220 and 230a represented a range of intermediates, in that such starch displayed a more modest rise in both amylose content and pasting onset temperature. The results would tend to suggest that there is generally a correlation between % amylose content and pasting onset temperature, which is in agreement with the known behaviour of starches from other sources, notably maize.

The marked increase in amylose content obtained by inhibition of class A SBE alone, compared to inhibition of class B SBE alone (see PCT/GB95/00634) might suggest that it would be advantageous to transform plants first with a construct to suppress class A SBE expression (probably, in practice, an antisense construct), select those plants giving rise to starch with the most altered properties, and then to re-transform with a construct to suppress class B SBE expression (again, in practice, probably an antisense construct), so as to maximise the degree of starch modification.

Figure 13:
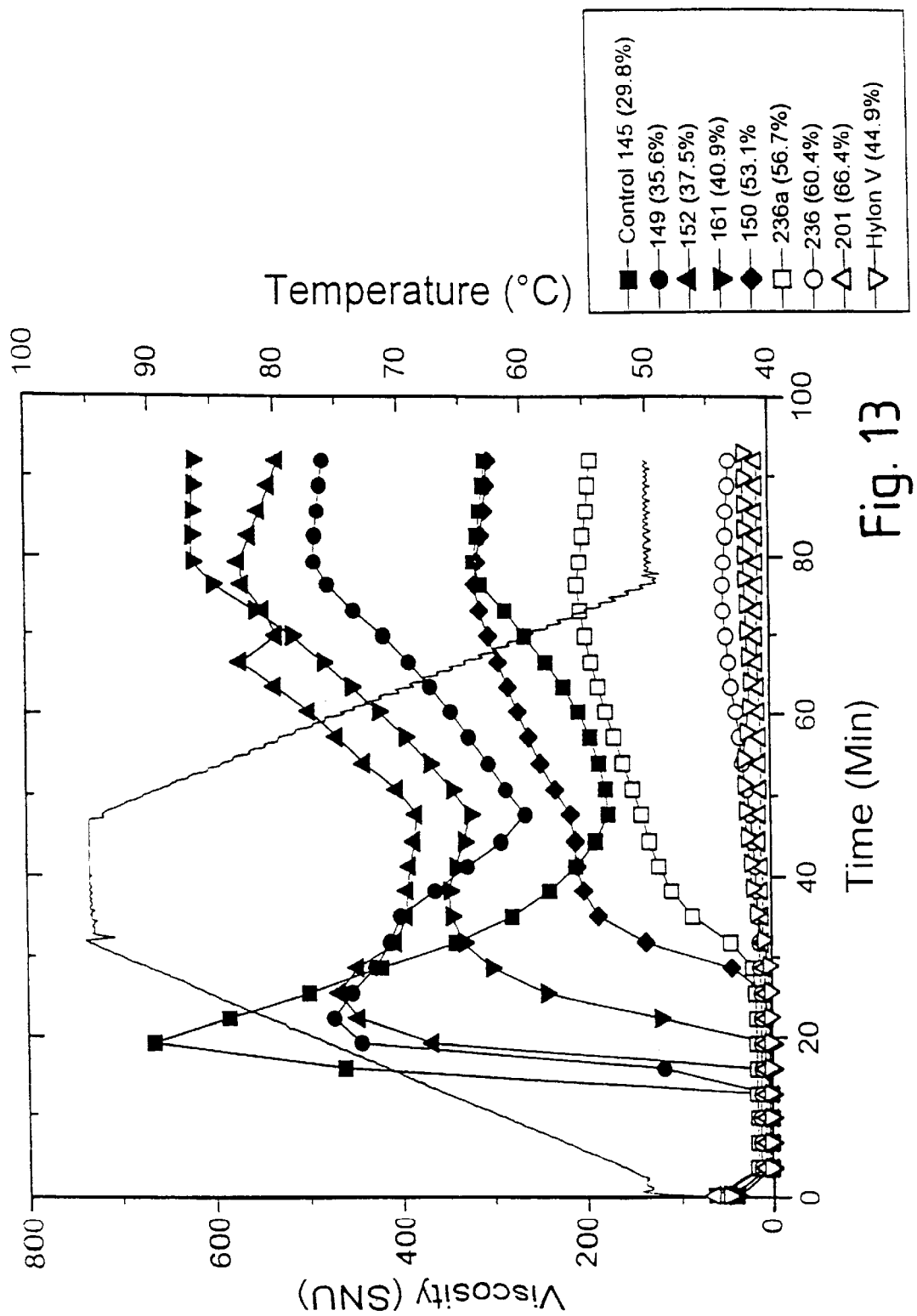
FIG. 13 shows vsicoamylographs for 10% w/w suspensions of starch from various transgenic potato plants made by the relevant method aspect of the invention.

In addition to pasting onset temperatures, other features of the viscoamylograph profile e.g. for starches from plants #149, 150, 152, 161, 201, 236 and 236a showed significant differences to starches from control plants, as illustrated in FIG. 13. Referring to FIG. 13, a number of viscoamylograph traces are shown. The legend is as follows: shaded box—normal potato starch control (29.8% amylose content); shaded circle—starch from plant 149 (35.6% amylose); shaded triangle, pointing upwards—plant 152 (37.5%); shaded triangle, pointing downwards—plant 161 (40.9%); shaded diamond—plant 150 (53.1%); unshaded box—plant 236a (56.7%); unshaded circle—plant 236 (60.4%); unshaded triangle, pointing upwards—plant 201 (66.4%); unshaded triangle, pointing downwards—HYLON® V starch, from maize (44.9% amylose). The thin line denotes the heating profile.

With increasing amylose content, peak viscosities during processing to 95° C. decrease, and the drop in viscosity from the peak until the end of the holding period at 95° C. also generally decreases (indeed, for some of the starch samples there is an increase in viscosity during this period). Both of these results are indicative of reduced granule fragmentation, and hence increased granule stability during pasting. This property has not previously been available in potato starch without extensive prior chemical or physical modification. For applications where a maximal viscosity after processing to 95° C. is desirable (i.e. corresponding to the viscosity after 47 minutes in the viscoamylograph test), starch from plant #152 would be selected as starches with both lower (Controls, #149) and higher (#161, #150) amylose contents have lower viscosities following this gelatinization and pasting regime (FIG. 13 and Table 1). It is believed that the viscosity at this stage is determined by a combination of the extent of granule swelling and the resistance of swollen granules to mechanical fragmentation. For any desired viscosity behaviour, one skilled in the art would select a potato starch from a range containing different amylose contents produced according to the invention by performing suitable standard viscosity tests.

Figure 2:
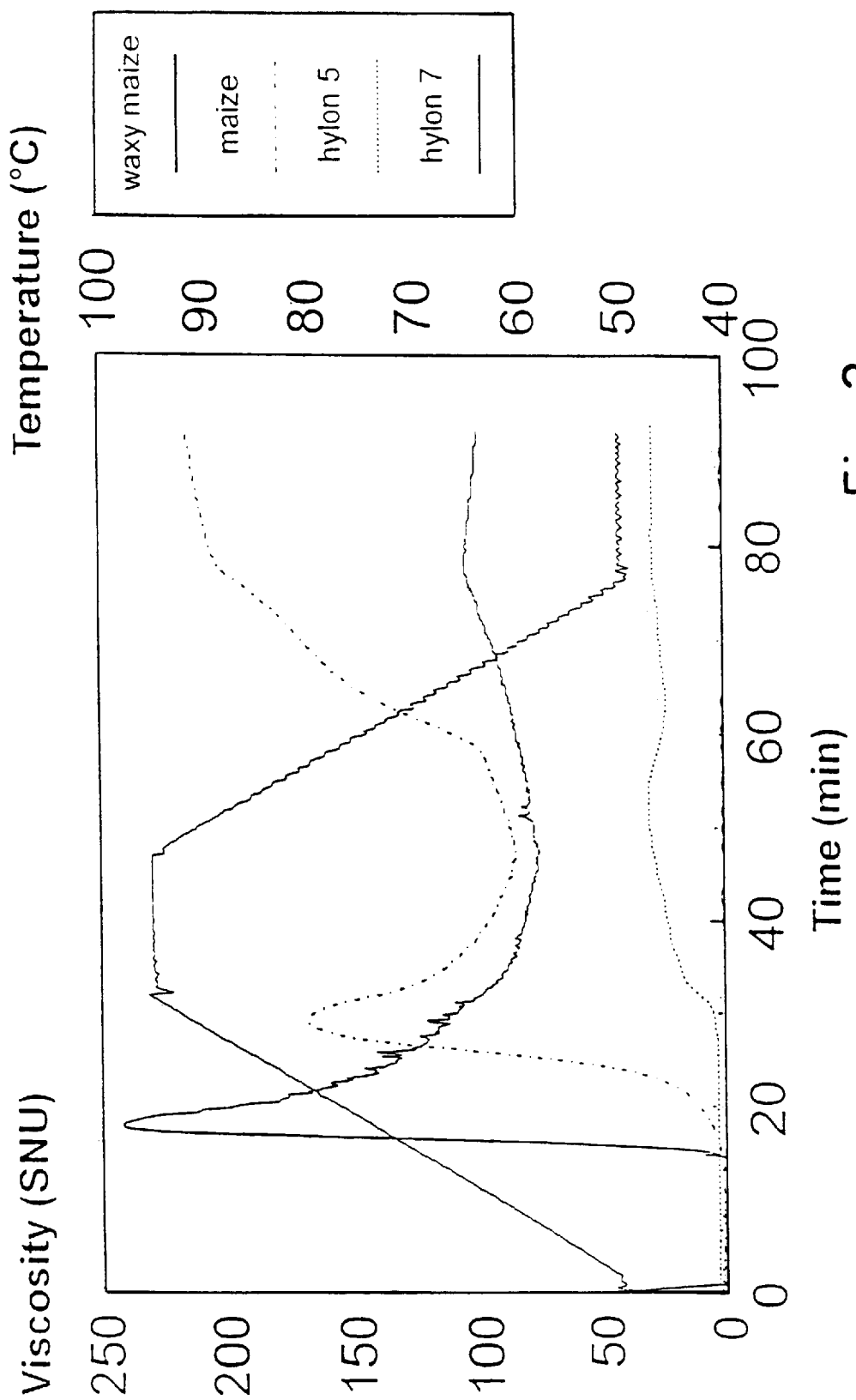
FIG. 2 shows vsicoamylographs for 10% suspensions of starch from various maize varieties.

Upon cooling pastes from 95° C. to 50° C., potato starches from most plants transformed in accordance with the invention showed an increase in viscoamylograph viscosity as expected for partial reassociation of amylose. Starches from plants #149, 152 and 161 all show viscosities at 50° C. significantly in excess of those for starches from control plants (FIG. 13 and Table 1). This contrasts with the effect of elevated amylose contents in starches from maize plants (FIG. 2) which show very low viscosities throughout the viscoamylograph test. Of particular note is the fact that, for similar amylose contents, starch from potato plant 150 (53% amylose) shows markedly increased viscosity compared with HYLON® V starch (44.9% amylose) as illustrated in FIG. 13. This demonstrates that useful properties which require elevated (35% or greater) amylose levels can be obtained by processing starches from potato plants below 100° C., whereas more energy-intensive processing is required in order to generate similarly useful properties from high amylose starches derived from maize plants.

Final viscosity in the viscoamylograph test (set-back viscosity after 92 minutes) is greatest for starch from plant #161 (40.9% amylose) amongst those tested (FIG. 13 and Table 1). Decreasing final viscosities are obtained for starches from plant #152 (37.5% amylose), #149 (35.6% amylose) and #150 (53.1% amy Set-back viscosity occurs where amylose molecules, exuded from the starch granule during pasting, start to re-associate outside the granule and form a viscous gel-like substance. It is believed that the set-back viscosity values of starches from transgenic potato plants represent a balance between the inherent amylose content of the starches and the ability of the amylose fraction to be exuded from the granule during pasting and therefore be available for the reassociation process which results in viscosity increase. For starches with low amylose content, increasing the amylose content tends to make more amylose available for re-association, thus increasing the set-back viscosity. However, above a threshold value, increased amylose content is thought to inhibit granule swelling, thus preventing exudation of amylose from the starch granule and reducing the amount of amylose available for re-association. This is supported by the RVA results obtained for the very high amylose content potato starches seen in the viscoamylograph profiles in FIG. 13. For any desired viscosity behaviour following set-back or retrogradation to any desired temperature over any desired timescale, one skilled in the art would select a potato starch from a range containing different amylose contents produced according to the invention by performing standard viscosity tests.

Further experiments with starch from plants #201 and 208 showed that this had an apparent amylose content of over 62% (see Table 1). Viscoamylograph studies showed that starch from these plants had radically altered properties and behaved in a manner similar to HYLON® V starch from maize plants (FIG. 13). Under the conditions employed in the viscoamylograph, this starch exhibited extremely limited (nearly undetectable) granule swelling. Thus, for example, unlike starch from control plants, starch from plants 201, 208 and 208a did not display a clearly defined pasting viscosity peak during the heating phase. Microscopic analysis confirmed that the starch granule structure underwent only minor swelling during the experimental heating process. This property may well be particularly useful in certain applications, as will be apparent to those skilled in the art.

Some re-grown plants have so far been found to increase still further the apparent amylose content of starch extracted therefrom. Such increases may be due to:- i) Growth and development of the first generation transformed plants may have been affected to some degree by the exogenous growth hormones present in the tissue culture system, which exogenous hormones were not present during growth of the second generation plants; and ii) Subsequent generations were grown under field conditions, which may allow for attainment of greater maturity than growth under laboratory conditions, it being generally held that amylose content of potato starch increases with maturity of the potato tuber.

Accordingly, it should be possible to obtain potato plants giving rise to tubers with starch having an amylose content in excess of the 66% level so far attained, simply by analysing a greater number of transformed plants and/or by re-growing transgenic plants through one or more generations under field conditions.

Table 1 shows that another characteristic of starch which is affected by the presence of anti-sense sequences to SBE is the phosphorus content. Starch from untransformed control plants had a phosphorus content of about 60–70 mg/100 gram dry weight (as determined according to the AOAC Official Methods of Analysis, 15th Edition, Method 948.09 "Phosphorus in Flour"). Introduction into the plant of an anti-sense SBE B sequence was found to cause a modest increase (about two-fold) in phosphorus content, which is in agreement with the previous findings reported at scientific meetings. Similarly, anti-sense to SBE A alone causes only a small rise in phosphorus content relative to untransformed controls. However, use of anti-sense to both SBE A and B in combination results in up to a four-fold increase in phosphorus content, which is far greater than any in planta phosphorus content previously demonstrated for potato starch.

This is useful in that, for certain applications, starch must be phosphorylated in vitro by chemical modification. The ability to obtain potato starch which, as extracted from the plant, already has a high phosphorus content will reduce the amount of in vitro phosphorylation required suitably to modify the starch. Thus, in another aspect the invention provides potato starch which, as extracted from the plant, has a phosphorus content in excess of 200 mg/100 gram dry weight starch. Typically the starch will have a phosphorus content in the range 200–240 mg/100 gram dry weight starch.

We claim:

1. A potato starch comprising amylose in an amount of at least about 35% to about 66%, as judged by the iodometric assay method of Morrison & Laignelet, and amylopectin.

2. A potato starch comprising amylose in an amount of at least about 35%, as judged by the iodometric assay method of Morrison & Laignelet, wherein the starch forms a suspension in water at 10% w/w at about 40° C.

3. The starch according to claim 1 or 2, having an amylose content of at least 37%.

4. The starch according to claim 1 or 2, having an amylose content of at least 40%.

5. The starch according to claim 1 or 2, or having an amylose content of at least 50%.

6. The starch according to claim 2, having an amylose content of about 66%.

7. The starch according to claim 2, having an amylose content of about 35%–about 66%.

8. The starch according to claim 1 or 2, which as extracted from a potato plant by wet milling at ambient temperature has a viscosity onset temperature in the range 70–95° C., as judged by viscoamylograph of a 10% w/w aqueous suspension thereof, performed at atmospheric pressure using the Newport Scientific Rapid Visco Analyser 3C with a heating profile of holding at 50° C. for 2 minutes, heating from 50 to 95° C. at a rate of 1.5° C. per minute, holding at 95° C. for 15 minutes, cooling from 95 to 50° C. at a rate of 1.5° C. per minute, and then holding at 50° C. for 15 minutes.

9. The starch according to claim 1 or 2, which as extracted from a potato plant by wet milling at ambient temperature has peak viscosity in the range 500–12 stirring number units (SNUs), as judged by viscoamylograph of a 10% w/w aqueous suspension thereof, performed at atmospheric pressure using the Newport Scientific Rapid Visco Analyser 3C with a beating profile of holding at 50° C. for 2 minutes, heating from 50 to 95° C. at a rate of 1.5° C. per minute, holding at 95° C. for 15 minutes, cooling from 95 to 50° C. at a rate of 1.5° C. per minute, and then holding at 50° C. for 15 minutes.

10. The starch according to claim 1 or 2, which as extracted from a potato plant by wet milling at ambient temperature has a pasting viscosity in the range 214–434 SNUs, as judged by viscoamylograph of a 10% w/w aqueous suspension thereof, performed at atmospheric pressure using the Newport Scientific Rapid Visco Analyser 3C with a heating profile of holding at 50° C. for 2 minutes, heating from 50 to 95° C. at a rate of 1.5° C. per minute, holding at 95° C. for 15 minutes, cooling from 95 to 50° C. at a rate or 1.5° C. per minute, and then holding at 50° C. for 15 minutes.

11. The starch according to claim 1 or 2, which as extracted from a potato plant by wet milling at ambient temperature has a set-back viscosity in the range 450–618 SNUs, as judged by viscoamylograph of a 10% ww aqueous suspension thereof, performed at atmospheric pressure using the Newport Scientific Rapid Visco Analyser 3C with a beating profile of holding at 50° C. for 2 minutes, heating from 50 to 95° C. at a rate of 1.5° C. per minute, holding at 95° C. for 15 minutes, cooling from 95 to 50° C. at a rate of 1.5° C. per minute, and then holding at 50° C. for 15 minutes.

12. The starch according to claim 1 or 2, which as extracted from a potato plant by wet milling at ambient temperature has a peak viscosity in the range 14–192 SNUs, as judged by viscoamylograph of a 10% w/w aqueous suspension thereof, performed at atmospheric pressure using the New Port Scientific Rapid Visco Analyser 3C with a heating profile of holding at 50° C. for 2 minutes, heating from 50 to 95° C. at a rate of 1.5° C. per minute, holding at 95° C. for 15 minutes, cooling from 95 to 50° C. at a rate of 1.5° C. per minute, and then holding at 50° C. for 15 minutes.

13. The starch according to claim 1 or 2, which as extracted from a potato plant by wet milling at ambient temperature has a peak viscosity in the range 200–500 SNUs and a set-back viscosity in the range 275–618 SNUs as judged by viscoamylograph of a 10% w/w aqueous suspension thereof, performed at atmospheric pressure using the Newport Scientific Rapid Visco Analyser 3C with a heating profile of holding at 50° C. for 2 minutes, beating from 50 to 95° C. at a rate of 1.5° C. per minute, holding at 95° C. for 15 minutes, cooling from 95 to 50° C. at a rate of 1.5° C. per minute, and then holding at 50° C. for 15 minutes.

14. The starch according to claim 1 or 2, or which as extracted from a potato plant by wet milling at ambient temperature has a viscosity which does not decrease between the start of the heating phase (step 2) and the start of the final holding phase (step 5) and has a set-back viscosity of 303 SNUs or less as judged by viscoamylograph of a 10% w/w aqueous suspension thereof, performed at atmospheric pressure using the Newport Scientific Rapid Visco Analyser 3C with a heating profile of holding at 50° C. for 2 minutes, heating from 50 to 95° C. at a rate of 1.5° C. per minute, holding at 95° C. for 15 minutes, cooling from 95 to 50° C. at a rate of 1.5° C. per minute, and then holding at 50° C. for 15 minutes.

15. The starch according to claim 1 or 2, which as extracted from a potato plant by wet milling at ambient temperature displays no significant increase in viscosity as judged by viscoamylograph conducted of a 10% w/w aqueous suspension thereof, performed at atmospheric pressure using the Newport Scientific Rapid Visco Analyser 3C with a heating profile of holding at 50° C. for 2 minutes, heating from 50 to 95° C. at a rate of 1.5° C. per minute, holding at 95° C. for 15 minutes, cooling from 95 to 50° C. at a rate of 1.5° C. per minute, and then holding at 50° C. for 15 minutes.

16. The starch according to claim 1 or 2, which as extracted from a potato plant, has a phosphorus content in excess of 200 mg/100 grams dry weight starch.

17. The starch according to claim 16, having a phosphorus content in the range 200–240 mg/100 grams dry weight starch.

18. The starch according to claim 1 or 2, wherein the starch has been further treated physically, chemically, and/or enzynmatically.

19. The starch according to claim 18, wherein the starch is a resistant starch.

20. The starch according to claim 19, wherein the starch has in excess of 5% total dietary fiber, as determined according to the Protsky method.

21. A potato starch obtainable from a plant having characteristics altered by a method selected from the group consisting of (a) introducing into the plant a portion of a nucleotide sequence encoding an effective portion of a class A starch branching enzyme (SBE) obtainable from potato plants to complement the branching enzyme mutation in *E coli* KV 832 cells and which is active when expressed in *E. coli* in the phosphorylation stimulation assay operably linked to a suitable promoter active in the plant so as to affect the expression of a gene present in plant;

(b) introducing into the plant a portion of a nucleotide sequence encoding an effective portion of a class A starch branching enzyme (SBE) obtainable from potato plants operably linked to a suitable promoter active in the plant so as to affect the expression of a gene present in the plant, wherein the nucleotide sequence is operably linked in the anti-sense orientation to a suitable promoter active in the plant;

(c) introducing into the plant a portion of a nucleotide sequence encoding an effective portion of a class A starch branching enzyme (SBE) obtainable from potato plants operably linked to a suitable promoter active in the plant so as to affect the expression of a gene present in the plant, wherein the introduced sequence comprises at least one region selected from the group consisting of a 5' untranslated region, a 3' untranslated region, and a coding region of the potato SBE class A SBE operably linked in the sense orientation to a promoter active in the plant;

(d) introducing into the plant a portion of a nucleotide sequence encoding an effective portion of a class A starch branching enzyme (SBE) obtainable from potato plants operably linked to a suitable promoter active in the plant so as to affect the expression of a gene present in the plant further comprising introducing into the plant one or more further sequences;

(e) introducing into the plant a portion of a nucleotide sequence encoding an effective portion of a class A starch branching enzyme (SBE) obtainable from potato plants operably linked to a suitable promoter active in the plant so as to affect the expression of a gene present in the plant further comprising introducing into the plant one or more further sequences operably linked in the anti-sense orientation to a suitable promoter active in the plant; and (f) introducing into the plant a portion of a nucleotide sequence encoding an effective portion of a class A starch branching enzyme (SBE) obtainable from potato plants operably linked to a suitable promoter active in the plant so as to affect the expression of a gene present in the plant further comprising introducing into the plant a portion of a class B SBE nucleotide sequence wherein the portion is effective to complement the branching enzyme mutation in *E. coli* KV 832 cells and which is active when expressed in *E. coli* in the phosphorylation stimulation assay, and the starch has an amylose content of at least 35% as judged by the iodometric assay method of Morrison & Laignelet, wherein the starch forms a suspension in water at 10% w/w at about 40° C.

22. A potato starch obtainable from a plant having characteristics altered by a method selected from the group consisting of (a) introducing into the plant a portion of a nucleotide sequence encoding an effective portion of a class A starch branching enzyme (SBE) obtainable from potato plants to complement the branching enzyme mutation in *E coli* KV 832 cells and which is active when expressed in *E. coli* in the phosphorylation stimulation assay operably linked to a suitable promoter active in the plant so as to affect the expression of a gene present in the plant;

(b) introducing into the plant a portion of a nucleotide sequence encoding an effective portion of a class A starch branching enzyme (SBE) obtainable from potato plants operably linked to a suitable promoter active in the plant so as to affect the expression of a gene present in the plant, wherein the nucleotide sequence is operably linked in the anti-sense orientation to a suitable promoter active in the plant;

(c) introducing into the plant a portion of a nucleotide sequence encoding an effective portion of a class A starch branching enzyme (SBE) obtainable from potato plants operably linked to a suitable promoter active in the plant so as to affect the expression of a gene present in the plant, wherein the introduced sequence comprises at least one region selected from the group consisting of a 5' untranslated region, a 3' untranslated region, and a coding region of the potato SBE class A SBE operably linked in the sense orientation to a promoter active in the plant;

(d) introducing into the plant a portion of nucleotide sequence encoding an effective portion of a class A starch branching enzyme (SBE) obtainable from potato plants operably linked to a suitable promoter active in the plant so as to affect the expression of a gene present in the plant further comprising introducing into the plant one or more further sequences;

(e) introducing into the plant a portion of a nucleotide sequence encoding an effective portion of a class A starch branching enzyme (SBE) obtainable front potato plants operably linked to a suitable promoter active in the plant so as the affect the expression of a gene present in the plant further comprising introducing into the plant one or more further sequences operably linked in the anti-sense orientation to a suitable promoter active in the plant; and (f) introducing into the plant a portion of a nucleotide sequence encoding an effective portion of a class A starch branching enzyme (SBE) obtainable from potato plants operably linked to a suitable promoter active in the plant so as to affect the expression of a gene present in the plant further comprising introducing into the plant a portion of a class B SBE nucleotide sequence wherein the portion is effective to complement the branching enzyme mutation in *E. coli* KV 832 cells and which is active when expressed in *E. coli* in the phosphorylation stimulation assay, and the starch has an amylose content of at least about 35% to about 66% as judged by the iodometric assay method of Morrison & Laignelet.

23. A method of modifying starch in vitro, comprising treating starch with an effective amount of a class A starch branching enzyme (SBE) polypeptide obtainable from potato plants and encoded by a nucleotide sequence encoding an effective portion of a class A SBE obtainable from potato plants, wherein the amount is effective to complement the branching enzyme mutation in *E coli* KV 832 cells and which is active when expressed in *E. coli* in the phosphorylation stimulation assay.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 57 base pairs
      (B) TYPE: nucleic acid
      (C) STRANDEDNESS: single
      (D) TOPOLOGY: linear (xi) SEQUENCE DESCRIPTION: SEQ ID NO: 1:

```
AAGGATCCGT CGACATCGAT AATACGACTC ACTATAGGGA TTTTTTTTTT TTTTTTT      57
```

(2) INFORMATION FOR SEQ ID NO: 2:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 2:

AAGGATCCGT CGACATC                                              17

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 3:

GACATCGATA ATACGAC                                              17

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 4:

CATCCAACCA CCATCTCGCA                                           20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 5:

TTGAGAGAAG ATACCTAAGT                                           20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 6:

ATGTTCAGTC CATCTAAAGT                                           20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 7:

AGAACAACAA TTCCTAGCTC                                           20

(2) INFORMATION FOR SEQ ID NO: 8:

(i) SEQUENCE CHARACTERISTICS:

```
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 8:

GGGGCCTTGA ACTCAGCAAT                                                20

(2) INFORMATION FOR SEQ ID NO: 9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 9:

CGTCCCAGCA TTCGACATAA                                                20

(2) INFORMATION FOR SEQ ID NO: 10:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 10:

CTTGGATCCT TGAACTCAGC AATTTG                                         26

(2) INFORMATION FOR SEQ ID NO: 11:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO: 11:

TAACTCGAGC AACGCGATCA CAAGTTCGT                                      29

(2) INFORMATION FOR SEQ ID NO: 12:

(i) SEQUENCE CHARACTERISTICS:
            (A) LENGTH: 3003 base pairs
            (B) TYPE: nucleic acid
            (C) STRANDEDNESS: single
            (D) TOPOLOGY: linear (xi) SEQUENCE DESCRIPTION: SEQ ID NO: 12:

GATGGGGCCT TGAACTCAGC AATTTGACAC TCAGTTAGTT ACACTGCCAT CACTTATCAG     60

ATCTCTATTT TTTCTCTTAA TTCCAACCAA GGAATGAATA AAAAGATAGA TTTGTAAAAA    120

CCCTAAGGAG AGAAGAAGAA AGATGGTGTA TACACTCTCT GGAGTTCGTT TTCCTACTGT    180

TCCATCAGTG TACAAATCTA ATGGATTCAG CAGTAATGGT GATCGGAGGA ATGCTAATAT    240

TTCTGTATTC TTGAAAAAAC ACTCTCTTTC ACGGAAGATC TTGGCTGAAA AGTCTTCTTA    300

CAATTCCGAA TCCCGACCTT CTACAATTGC AGCATCGGGG AAAGTCCTTG TGCCTGGAAT    360

CCAGAGTGAT AGCTCCTCAT CCTCAACAGA TCAATTTGAG TTCGCTGAGA CATCTCCAGA    420

AAATTCCCCA GCATCAACTG ATGTAGATAG TTCAACAATG GAACACGCTA GCCAGATTAA    480

AACTGAGAAC GATGACGTTG AGCCGTCAAG TGATCTTACA GGAAGTGTTG AAGAGCTGGA    540

TTTTGCTTCA TCACTACAAC TACAAGAAGG TGGTAAACTG GAGGAGTCTA AAACATTAAA    600
```

-continued

| | |
|---|---|
| TACTTCTGAA GAGACAATTA TTGATGAATC TGATAGGATC AGAGAGAGGG GCATCCCTCC | 660 |
| ACCTGGACTT GGTCAGAAGA TTTATGAAAT AGACCCCCTT TTGACAAACT ATCGTCAACA | 720 |
| CCTTGATTAC AGGTATTCAC AGTACAAGAA ACTGAGGGAG GCAATTGACA AGTATGAGGG | 780 |
| TGGTTTGGAA GCTTTTTCTC GTGGTTATGA AAGAATGGGT TTCACTCGTA GTGCTACAGG | 840 |
| TATCACTTAC CGTGAGTGGG CTCCTGGTGC CCAGTCAGCT GCCCTCATTG GGGATTTCAA | 900 |
| CAATTGGGAC GCAAATGCTG ACTTTATGAC TCGGAATGAA TTTGGTGTCT GAGAGATTTT | 960 |
| TCTGCCAAAT AATGTGGATG GTTCTCCTGC AATTCCTCAT GGGTCCAGAG TGAAGATACG | 1020 |
| TATGGACACT CCATCAGGTG TTAAGGATTC CATTCCTGCT TGGATCAACT ACTCTTTACA | 1080 |
| GCTTCCTGAT GAAATTCCAT ATAATGGAAT ATATTATGAT CCACCCGAAG AGGAGAGGTA | 1140 |
| TATCTTCCAA CACCCACGGC CAAAGAAACC AAAGTCGGTG AGAATATATG AATCTCATAT | 1200 |
| TGGAATGAGT AGTCCGGAGC CTAAAATTAA CTCATACGTG AATTTTAGAG ATGAAGTTCT | 1260 |
| TCCTCGCATA AAAAAAGCTT GGGTACAATG CGGTGCAAAT TATGGCTATT CAAGAGCATT | 1320 |
| CTTATTATGC TAGTTTTGGT TATCATGTCA CAAATTTTTT TGCACCAAGC AGCCGTTTTG | 1380 |
| GAACGCCCGA CGACCTTAAG TCTTTGATTG ATAAAGCTCA TGAGCTAGGA ATTGTTGTTC | 1440 |
| TCATGGACAT TGTTCACAGC CATGCATCAA ATAATACTTT AGATGGACTG AACATGTTTG | 1500 |
| ACGGCACAGA TAGTTGTTAC TTTCACTCTG GAGCTCGTGG TTATCATTGG ATGTGGGATT | 1560 |
| TCCGCCTCTT TAACTATGGA AACTGGGAGG TACTTAGGTA TCTTCTCTCA AATGCGAGAT | 1620 |
| GGTGGTTGGA TGAGTTCAAA TTTGATGGAT TTAGATTTGA TGGTGTGACA TCAATGATGT | 1680 |
| GTACTCACCA CGGATTATCG GTGGGATTCA CTGGGAACTA CGAGGAATAC TTTGGACTCG | 1740 |
| CAACTGATGT GGATGCTGTT GTGTATCTGA TGCTGGTCAA CGATCTTATT CATGGGCTTT | 1800 |
| TCCCAGATGC AATTACCATT GGTGAAGATG TTAGCGGAAT GCCGACATTT TGTGTTCCCG | 1860 |
| TTCAAGATGG GGGTGTTGGC TTTGACTATC GGCTGCATAT GGCAATTGCT GATAAATGGA | 1920 |
| TTGAGTTGCT CAAGAAACGG GATGAGGATT GGAGAGTGGG TGATATTGTT CATACACTGA | 1980 |
| CAAATAGAAG ATGGTCGGAA AAGTGTGTTT CATACGCTGA AAGTCATGAT CAAGCTCTAG | 2040 |
| TCGGTGATAA AACTATAGCA TTCTGGCTGA TGGACAAGGA TATGTATGAT TTTATGGCTC | 2100 |
| TGGATAGACC GTCAACATCA TTAATAGATC GTGGGATAGC ATTACACAAG ATGATTAGGC | 2160 |
| TTGTAACTAT GGGATTAGGA GGAGAAGGGT ACCTAAATTT CATGGGAAAT GAATTCGGCC | 2220 |
| ACCCTGAGTG GATTGATTTC CCTAGGGCTG AACAACACCT CTCTGATGGC TCAGTAATTC | 2280 |
| CCAGAAACCA ATTCAGTTAT GATAAATGCA GACGGAGATT TGACCTGGGA GATGCAGAAT | 2340 |
| ATTTAAGATA CCGTGGGTTG CAAGAATTTG ACCGGGCTAT GCAGTATCTT GAAGATAAAT | 2400 |
| ATGAGTTTAT GACTTCAGAA CACCAGTTCA TATCACGAAA GGATGAAGGA GATAGGATGA | 2460 |
| TTGTATTTGA AAAAGGAAAC CTAGTTTTTG TCTTTAATTT TCACTGGACA AAAGGCTATT | 2520 |
| CAGACTATCG CATAGGCTGC CTGAAGCCTG GAAAATACAA GGTTGCCTTG GACTCAGATG | 2580 |
| ATCCACTTTT TGGTGGCTTC GGGAGAATTG ATCATAATGC CGAATATTTC ACCTTTGAAG | 2640 |
| GATGGTATGA TGATCGTCCT CGTTCAATTA TGGTGTATGC ACCTAGTAGA ACAGCAGTGG | 2700 |
| TCTATGCACT AGTAGACAAA GAAGAAGAAG AAGAAGAAGA AGTAGCAGTA GTAGAAGAAG | 2760 |
| TAGTAGTAGA AGAAGAATGA ACGAACTTGT GATCGCGTTG AAAGATTTGA ACGCCACATA | 2820 |
| GAGCTTCTTG ACGTATCTGG CAATATTGCA TTAGTCTTGG CGGAATTTCA TGTGACAACA | 2880 |
| GGTTTGCAAT TCTTTCCACT ATTAGTAGTG CAACGATATA CGCAGAGATG AAGTGCTGAA | 2940 |
| CAAAAACATA TGTAAAATCG ATGAATTTAT GTCGAATGCT GGGACGATCG AATTCCTGCA | 3000 |

```
GCC                                                                  3003

(2) INFORMATION FOR SEQ ID NO: 13:

(i) SEQUENCE CHARACTERISTICS:
        (A) LENGTH: 2975 base pairs
        (B) TYPE: nucleic acid
        (C) STRANDEDNESS: single
        (D) TOPOLOGY: linear (xi) SEQUENCE DESCRIPTION: SEQ ID NO: 13:

TTGATGGGCC TTGAACTCAG CAATTTGACA CTCAGTTAGT TACACTCCTA TCACTTATCA      60

GATCTCTATT TTTTCTCTTA ATTCCAACCA GGGGAATGAA TAAAAGGATA GATTTGTAAA     120

AACCCTAAGG AGAGAAGAAG AAAGATGGTG TATATACTCT CTGGAGTTCG TTTTCCTACT     180

GTTCCATCAG TGTACAAATC TAATGGATTC AGCAGTAATG GTGATCGGAG GAATGCTAAT     240

GTTTCTGTAT TCTTGAAAAA GCACTCTCTT TCACGGAAGA TCTTGGCTGA AAAGTCTTCT     300

TACAATTCCG AATTCCGACC TTCTACAGTT GCAGCATCGG GGAAAGTCCT TGTGCCTGGA     360

ACCCAGAGTG ATAGCTCCTC ATCCTCAACA GACCAATTTG AGTTCACTGA ACATCTCCA     420

GAAAATTCCC CAGCATCAAC TGATGTAGAT AGTTCAACAA TGGAACACGC TAGCCAGATT     480

AAAACTGAGA ACGATGACGT TGAGCCGTCA AGTGATCTTA CAGGAAGTGT TGAAGAGCTG     540

GATTTTGCTT CATCACTACA ACTACAAGAA GGTGGTAAAC TGGAGGAGTC TAAAACATTA     600

AATACTTCTG AAGAGACAAT TATTGATGAA TCTGATAGGA TCAGAGAGAG GGCATCCCT     660

CCACCTGGAC TTGGTCAGAA GATTTATGAA ATAGACCCCC TTTTGACAAA CTATCGTCAA     720

CACCTTGATT ACAGGTATTC ACAGTACAAG AAACTGAGGG AGGCAATTGA CAAGTATGAG     780

GGTGGTTTGG AAGCTTTTCT CGTGGTTATG AAAAAATGGG TTTCACTCGT AGTGCTACAG     840

GTATCACTTA CCGTGAGTGG GCTCCTGGTG CCCAGTCAGC TGCCCTCATT GGAGATTTCA     900

ACAATTGGGA CGCAAATGCT GACATTATGA CTCGGAATGA ATTTGGTGTC TGGGAGATTT     960

TTCTGCCAAA TAATGTGGAT GGTTCTCCTG CAATTCCTCA TGGGTCCAGA GTGAAGATAC    1020

GTATGGACAC TCCATCAGGT GTTAAGGATT CCATTCCTGC TTGGATCAAC TACTCTTTAC    1080

AGCTTCCTGA TGAAATTCCA TATAATGGAA TATATTATGA TCCACCCGAA GAGGAGAGGT    1140

ATATCTTCCA ACACCCACGG CCAAAGAAAC CAAAGTCGCT GAGAATATAT GAATCTCATA    1200

TTGGAATGAG TAGTCCGGAG CCTAAAATTA ACTCATACGT GAATTTTAGA GATGAAGTTC    1260

TTCCTCGCAT AAAAAAGCTT GGGTACAATG CGCTGCGAAT TATGGCTATT CAAGAGCATT    1320

CTTATTATGC TAGTTTTGGT TATCATGTCA CAAATTTTTT TGCACCAAGC AGCCGTTTTG    1380

GAACGCCCGA CGACCTTAAG TCTTCGATTG ATAAAGCTCA TGAGCTAGGA ATTGTTGTTC    1440

TCATGGACAT CGTTCACAGC CATGCATCAA ATAATACTTT AGATGGACTG AACATGTTTG    1500

ACGGCACCGA TAGTTGTTAC TTTCACTCTG GAGCTCGTGG TTATCATTGG ATGTGGGATT    1560

CCGCCTCTTT AACTATGGAA ACTGGGAGGT ACTTAGGTAT CTTCTCTCAA ATGCGAGATG    1620

GTGGTTGGAT GAGTTCAAAT TTGATGGATT TAGATTCGAT GGTGTGACAT CAATGATGTA    1680

TACTCACCAC GGATTATCGG TGGGATTCAC TGGGAACTAC GAGGAATACT TTGGACTCGC    1740

AACTGATGTG GATGCTGTTG TGTATCTGAT GCTGGTCAAC GATCTTATTC ATAGGCTTTT    1800

CCCAGATGCA ATTACCATTG GTGAAGATGT TAGCGGAATG CCGACATTTT GTATTCCCGT    1860

TCAAGATGGG GGTGTTGGCT TTGACTATCG GCTGCATATG GCAATTGCTG ATAAATGGAT    1920

TGAGTTGCTC AAGAAACGGG ATGAGGATTG GAGAGTGGGT GATATTGTTC ATACACTGAC    1980
```

-continued

```
AAATAGAAGA TGGTCGGAAA AGTGTGTTTC ATACGCTGAA AGTCATGATC AAGCTCTAGT    2040

CGGTGATAAA ACTATAGCAT TCTGGCTGAT GGACAAGGAT ATGTATGATT TTATGGCTCT    2100

GGATAGACCG CCAACATCAT TAATAGATCG TGGGATAGCA TTGCACAAGA TGATTAGGCT    2160

TGTAACTATG GGATTAGGAG GAGAAGGGTA CCTAAATTTC ATGGGAAATG AATTCGGCCA    2220

CCCTGAGTGG ATTGATTTCC CTAGGGCTGA GCCACACCTT TCTGATGGCT CAGTAATTCC    2280

CGGAAACCAA TTCAGTTATG ATAAATGCAG ACGGAGATTT GACCTGGGAG ATGCAGAATA    2340

TTTAAGATAC CATGGGTTAC AAGAATTTGA CTGGGCTATG CAGTATCTTG AAGATAAATA    2400

TGAGTTTATG ACTTCAGAAC ACCAGTTCAT ATCACGAAAG GATGAAGGAG ATAGGATGAT    2460

TGTATTTGAA AGAGGAAACC TAGTTTTCGT CTTTAATTTT CACTGGACAA ATAGCTATTC    2520

AGACTATCGC ATAGGCTGCC TGAAGCCTGG AAAATACAAG GTTGTCTTGG ACTCAGATGA    2580

TCCACTTTTT GGTGGCTTCG GGAGAATTGA TCATAATGCC GAATATTTCA CCTCTGAAGG    2640

ATCGTATGAT GATCGTCCTT GTTCAATTAT GGTGTATGCA CCTAGTAGAA CAGCAGTGGT    2700

CTATGCACTA GTAGACAAAC TAGAAGTAGC AGTAGTAGAA GAACCCATTG AAGAATGAAC    2760

GAACTTGTGA TCGCGTTGAA AGATTTGAAC GTTACTTGGT CATCCACATA GAGCTTCTTG    2820

ACATCAGTCT TGGCGGAATT GCATGTGACA ACAAGGTTTG CAGTTCTTTC CACTATTAGT    2880

AGTCCACCGA TATACGCAGA GATGAAGTGC TGAACAAACA TATGTAAAAT CGATGAATTT    2940

ATGTCGAATG CTGGGACGAT CGAATTCCTG CAGCC                              2975

(2) INFORMATION FOR SEQ ID NO: 14:

(i) SEQUENCE CHARACTERISTICS:
        (A) LENGTH: 3033 base pairs
        (B) TYPE: nucleic acid
        (C) STRANDEDNESS: single
        (D) TOPOLOGY: linear (ix) FEATURE:
        (A) NAME/KEY: CDS
        (B) LOCATION:145..2790

(xi) SEQUENCE DESCRIPTION: SEQ ID NO: 14:

TTGATGGGGC CTTGAACTCA GCAATTTGAC ACTCAGTTAG TTACACTCCT ATCACTTATC    60

AGATCTCTAT TTTTTCTCTT AATTCCAACC AAGGAATGAA TAAAAGGATA GATTTGTAAA    120

AACCCTAAGG AGAGAAGAAG AAAG ATG GTG TAT ACA CTC TCT GGA GTT CGT      171
                          Met Val Tyr Thr Leu Ser Gly Val Arg
                           1               5

TTT CCT ACT GTT CCA TCA GTG TAC AAA TCT AAT GGA TTC AGC AGT AAT    219
Phe Pro Thr Val Pro Ser Val Tyr Lys Ser Asn Gly Phe Ser Ser Asn
 10              15                  20                  25

GGT GAT CGG AGG AAT GCT AAT GTT TCT GTA TTC TTG AAA AAG CAC TCT    267
Gly Asp Arg Arg Asn Ala Asn Val Ser Val Phe Leu Lys Lys His Ser
             30                  35                  40

CTT TCA CGG AAG ATC TTG GCT GAA AAG TCT TCT TAC AAT TCC GAA TTC    315
Leu Ser Arg Lys Ile Leu Ala Glu Lys Ser Ser Tyr Asn Ser Glu Phe
         45                  50                  55

CGA CCT TCT ACA GTT GCA GCA TCG GGG AAA GTC CTT GTG CCT GGA ACC    363
Arg Pro Ser Thr Val Ala Ala Ser Gly Lys Val Leu Val Pro Gly Thr
     60                  65                  70

CAG AGT GAT AGC TCC TCA TCC TCA ACA GAC CAA TTT GAG TTC ACT GAG    411
Gln Ser Asp Ser Ser Ser Ser Thr Asp Gln Phe Glu Phe Thr Glu
 75                  80                  85

ACA TCT CCA GAA AAT TCC CCA GCA TCA ACT GAT GTA GAT AGT TCA ACA    459
```

```
      Thr Ser Pro Glu Asn Ser Pro Ala Ser Thr Asp Val Asp Ser Ser Thr
       90              95              100             105

ATG GAA CAC GCT AGC CAG ATT AAA ACT GAG AAC GAT GAC GTT GAG CCG         507
Met Glu His Ala Ser Gln Ile Lys Thr Glu Asn Asp Asp Val Glu Pro
            110             115             120

TCA AGT GAT CTT ACA GGA AGT GTT GAA GAG CTG GAT TTT GCT TCA TCA         555
Ser Ser Asp Leu Thr Gly Ser Val Glu Glu Leu Asp Phe Ala Ser Ser
            125             130             135

CTA CAA CTA CAA GAA GGT GGT AAA CTG GAG GAG TCT AAA ACA TTA AAT         603
Leu Gln Leu Gln Glu Gly Gly Lys Leu Glu Glu Ser Lys Thr Leu Asn
        140             145             150

ACT TCT GAA GAG ACA ATT ATT GAT GAA TCT GAT AGG ATC AGA GAG AGG         651
Thr Ser Glu Glu Thr Ile Ile Asp Glu Ser Asp Arg Ile Arg Glu Arg
        155             160             165

GGC ATC CCT CCA CCT GGA CTT GGT CAG AAG ATT TAT GAA ATA GAC CCC         699
Gly Ile Pro Pro Pro Gly Leu Gly Gln Lys Ile Tyr Glu Ile Asp Pro
170             175             180             185

CTT TTG ACA AAC TAT CGT CAA CAC CTT GAT TAC AGG TAT TCA CAG TAC         747
Leu Leu Thr Asn Tyr Arg Gln His Leu Asp Tyr Arg Tyr Ser Gln Tyr
            190             195             200

AAG AAA CTG AGG GAG GCA ATT GAC AAG TAT GAG GGT GGT TTG GAA GCC         795
Lys Lys Leu Arg Glu Ala Ile Asp Lys Tyr Glu Gly Gly Leu Glu Ala
            205             210             215

TTT TCT CGT GGT TAT GAA AAA ATG GGT TTC ACT CGT AGT GCT ACA GGT         843
Phe Ser Arg Gly Tyr Glu Lys Met Gly Phe Thr Arg Ser Ala Thr Gly
            220             225             230

ATC ACT TAC CGT GAG TGG GCT CTT GGT GCC CAG TCA GCT GCC CTC ATT         891
Ile Thr Tyr Arg Glu Trp Ala Leu Gly Ala Gln Ser Ala Ala Leu Ile
        235             240             245

GGA GAT TTC AAC AAT TGG GAC GCA AAT GCT GAC ATT ATG ACT CGG AAT         939
Gly Asp Phe Asn Asn Trp Asp Ala Asn Ala Asp Ile Met Thr Arg Asn
250             255             260             265

GAA TTT GGT GTC TGG GAG ATT TTT CTG CCA AAT AAT GTG GAT GGT TCT         987
Glu Phe Gly Val Trp Glu Ile Phe Leu Pro Asn Asn Val Asp Gly Ser
            270             275             280

CCT GCA ATT CCT CAT GGG TCC AGA GTG AAG ATA CGT ATG GAC ACT CCA        1035
Pro Ala Ile Pro His Gly Ser Arg Val Lys Ile Arg Met Asp Thr Pro
            285             290             295

TCA GGT GTT AAG GAT TCC ATT CCT GCT TGG ATC AAC TAC TCT TTA CAG        1083
Ser Gly Val Lys Asp Ser Ile Pro Ala Trp Ile Asn Tyr Ser Leu Gln
            300             305             310

CTT CCT GAT GAA ATT CCA TAT AAT GGA ATA CAT TAT GAT CCA CCC GAA        1131
Leu Pro Asp Glu Ile Pro Tyr Asn Gly Ile His Tyr Asp Pro Pro Glu
        315             320             325

GAG GAG AGG TAT ATC TTC CAA CAC CCA CGG CCA AAG AAA CCA AAG TCG        1179
Glu Glu Arg Tyr Ile Phe Gln His Pro Arg Pro Lys Lys Pro Lys Ser
330             335             340             345

CTG AGA ATA TAT GAA TCT CAT ATT GGA ATG AGT AGT CCG GAG CCT AAA        1227
Leu Arg Ile Tyr Glu Ser His Ile Gly Met Ser Ser Pro Glu Pro Lys
            350             355             360

ATT AAC TCA TAC GTG AAT TTT AGA GAT GAA GTT CTT CCT CGC ATA AAA        1275
Ile Asn Ser Tyr Val Asn Phe Arg Asp Glu Val Leu Pro Arg Ile Lys
            365             370             375

AAG CTT GGG TAC AAT GCG CTG CAA ATT ATG GCT ATT CAA GAG CAT TCT        1323
Lys Leu Gly Tyr Asn Ala Leu Gln Ile Met Ala Ile Gln Glu His Ser
            380             385             390

TAT TAC GCT AGT TTT GGT TAT CAT GTC ACA AAT TTT TTT GCA CCA AGC        1371
Tyr Tyr Ala Ser Phe Gly Tyr His Val Thr Asn Phe Phe Ala Pro Ser
        395             400             405
```

```
                                                    -continued
AGC CGT TTT GGA ACG CCC GAC GAC CTT AAG TCT TTG ATT GAT AAA GCT      1419
Ser Arg Phe Gly Thr Pro Asp Asp Leu Lys Ser Leu Ile Asp Lys Ala
410                 415                 420                 425

CAT GAG CTA GGA ATT GTT GTT CTC ATG GAC ATT GTT CAC AGC CAT GCA      1467
His Glu Leu Gly Ile Val Val Leu Met Asp Ile Val His Ser His Ala
                430                 435                 440

TCA AAT AAT ACT TTA GAT GGA CTG AAC ATG TTT GAC TGC ACC GAT AGT      1515
Ser Asn Asn Thr Leu Asp Gly Leu Asn Met Phe Asp Cys Thr Asp Ser
        445                 450                 455

TGT TAC TTT CAC TCT GGA GCT CGT GGT TAT CAT TGG ATG TGG GAT TCC      1563
Cys Tyr Phe His Ser Gly Ala Arg Gly Tyr His Trp Met Trp Asp Ser
460                 465                 470

CGC CTC TTT AAC TAT GGA AAC TGG GAG GTA CTT AGG TAT CTT CTC TCA      1611
Arg Leu Phe Asn Tyr Gly Asn Trp Glu Val Leu Arg Tyr Leu Leu Ser
        475                 480                 485

AAT GCG AGA TGG TGG TTG GAT GCG TTC AAA TTT GAT GGA TTT AGA TTT      1659
Asn Ala Arg Trp Trp Leu Asp Ala Phe Lys Phe Asp Gly Phe Arg Phe
490                 495                 500                 505

GAT GGT GTG ACA TCA ATG ATG TAT ATT CAC CAC GGA TTA TCG GTG GGA      1707
Asp Gly Val Thr Ser Met Met Tyr Ile His His Gly Leu Ser Val Gly
                510                 515                 520

TTC ACT GGG AAC TAC GAG GAA TAC TTT GGA CTC GCA ACT GAT GTG GAT      1755
Phe Thr Gly Asn Tyr Glu Glu Tyr Phe Gly Leu Ala Thr Asp Val Asp
        525                 530                 535

GCT GTT GTG TAT CTG ATG CTG GTC AAC GAT CTT ATT CAT GGG CTT TTC      1803
Ala Val Val Tyr Leu Met Leu Val Asn Asp Leu Ile His Gly Leu Phe
                540                 545                 550

CCA GAT GCA ATT ACC ATT GGT GAA GAT GTT AGC GGA ATG CCG ACA TTT      1851
Pro Asp Ala Ile Thr Ile Gly Glu Asp Val Ser Gly Met Pro Thr Phe
        555                 560                 565

TGT ATT CCC GTC CAA GAG GGG GGT GTT GGC TTT GAC TAT CGG CTG CAT      1899
Cys Ile Pro Val Gln Glu Gly Gly Val Gly Phe Asp Tyr Arg Leu His
570                 575                 580                 585

ATG GCA ATT GCT GAT AAA CGG ATT GAG TTG CTC AAG AAA CGG GAT GAG      1947
Met Ala Ile Ala Asp Lys Arg Ile Glu Leu Leu Lys Lys Arg Asp Glu
                590                 595                 600

GAT TGG AGA GTG GGT GAT ATT GTT CAT ACA CTG ACA AAT AGA AGA TGG      1995
Asp Trp Arg Val Gly Asp Ile Val His Thr Leu Thr Asn Arg Arg Trp
        605                 610                 615

TCG GAA AAG TGT GTT TCA TAC GCT GAA AGT CAT GAT CAA GCT CTA GTC      2043
Ser Glu Lys Cys Val Ser Tyr Ala Glu Ser His Asp Gln Ala Leu Val
        620                 625                 630

GGT GAT AAA ACT ATA GCA TTC TGG CTG ATG GAC AAG GAT ATG TAT GAT      2091
Gly Asp Lys Thr Ile Ala Phe Trp Leu Met Asp Lys Asp Met Tyr Asp
635                 640                 645

TTT ATG GCT CTG GAT AGA CCG TCA ACA TCA TTA ATA GAT CGT GGG ATA      2139
Phe Met Ala Leu Asp Arg Pro Ser Thr Ser Leu Ile Asp Arg Gly Ile
650                 655                 660                 665

GCA TTG CAC AAG ATG ATT AGG CTT GTA ACT ATG GGA TTA GGA GGA GAA      2187
Ala Leu His Lys Met Ile Arg Leu Val Thr Met Gly Leu Gly Gly Glu
                670                 675                 680

GGG TAC CTA AAT TTC ATG GGA AAT GAA TTC GGC CAC CCT GAG TGG ATT      2235
Gly Tyr Leu Asn Phe Met Gly Asn Glu Phe Gly His Pro Glu Trp Ile
        685                 690                 695

GAT TTC CCT AGG GCT GAA CAA CAC CTC TCT GAT GGC TCA GTA ATC CCC      2283
Asp Phe Pro Arg Ala Glu Gln His Leu Ser Asp Gly Ser Val Ile Pro
        700                 705                 710

GGA AAC CAA TTC AGT TAT GAT AAA TGC AGA CGG AGA TTT GAC CTG GGA      2331
Gly Asn Gln Phe Ser Tyr Asp Lys Cys Arg Arg Arg Phe Asp Leu Gly
        715                 720                 725
```

```
GAT GCA GAA TAT TTA AGA TAC CGT GGG TTG CAA GAA TTT GAC CGG CCT    2379
Asp Ala Glu Tyr Leu Arg Tyr Arg Gly Leu Gln Glu Phe Asp Arg Pro
730                 735                 740                 745

ATG CAG TAT CTT GAA GAT AAA TAT GAG TTT ATG ACT TCA GAA CAC CAG    2427
Met Gln Tyr Leu Glu Asp Lys Tyr Glu Phe Met Thr Ser Glu His Gln
            750                 755                 760

TTC ATA TCA CGA AAG GAT GAA GGA GAT AGG ATG ATT GTA TTT GAA AAA    2475
Phe Ile Ser Arg Lys Asp Glu Gly Asp Arg Met Ile Val Phe Glu Lys
                765                 770                 775

GGA AAC CTA GTT TTT GTC TTT AAT TTT CAC TGG ACA AAA AGC TAT TCA    2523
Gly Asn Leu Val Phe Val Phe Asn Phe His Trp Thr Lys Ser Tyr Ser
            780                 785                 790

GAC TAT CGC ATA GCC TGC CTG AAG CCT GGA AAA TAC AAG GTT GCC TTG    2571
Asp Tyr Arg Ile Ala Cys Leu Lys Pro Gly Lys Tyr Lys Val Ala Leu
                795                 800                 805

GAC TCA GAT GAT CCA CTT TTT GGT GGC TTC GGG AGA ATT GAT CAT AAT    2619
Asp Ser Asp Asp Pro Leu Phe Gly Gly Phe Gly Arg Ile Asp His Asn
810                 815                 820                 825

GCC GAA TAT TTC ACC TTT GAA GGA TGG TAT GAT GAT CGT CCT CGT TCA    2667
Ala Glu Tyr Phe Thr Phe Glu Gly Trp Tyr Asp Asp Arg Pro Arg Ser
            830                 835                 840

ATT ATG GTG TAT GCA CCT TGT AAA ACA GCA GTG GTC TAT GCA CTA GTA    2715
Ile Met Val Tyr Ala Pro Cys Lys Thr Ala Val Val Tyr Ala Leu Val
                845                 850                 855

GAC AAA GAA GAA GAA GAA GAA GAA GAA GAA GAA GAA GAA GTA GCA GCA    2763
Asp Lys Glu Glu Glu Glu Glu Glu Glu Glu Glu Glu Glu Val Ala Ala
860                 865                 870

GTA GAA GAA GTA GTA GTA GAA GAA GAA TGAACGAACT TGTGATCGCG          2810
Val Glu Glu Val Val Val Glu Glu Glu
            875                 880

TTGAAAGATT TGAACGCTAC ATAGAGCTTC TTGACGTATC TGGCAATATT GCATCAGTCT   2870

TGGCGGAATT TCATGTGACA CAAGGTTTGC AATTCTTTCC ACTATTAGTA GTGCAACGAT   2930

ATACGCAGAG ATGAAGTGCT GAACAAACAT ATGTAAAATC GATGAATTTA TGTCGAATGC   2990

TGGGACGATC GAATTCCTGC AGGCCGGGGG ACCCCTTAGT TCT                     3033

(2) INFORMATION FOR SEQ ID NO: 15:

(i) SEQUENCE CHARACTERISTICS:
        (A) LENGTH: 882 amino acids
        (B) TYPE: amino acid
        (D) TOPOLOGY: linear (ii) MOLECULE TYPE: protein (xi) SEQUENCE DESCRIPTION: SEQ ID NO: 15:

Met Val Tyr Thr Leu Ser Gly Val Arg Phe Pro Thr Val Pro Ser Val
1               5                   10                  15

Tyr Lys Ser Asn Gly Phe Ser Ser Asn Gly Asp Arg Arg Asn Ala Asn
            20                  25                  30

Val Ser Val Phe Leu Lys Lys His Ser Leu Ser Arg Lys Ile Leu Ala
        35                  40                  45

Glu Lys Ser Ser Tyr Asn Ser Glu Phe Arg Pro Ser Thr Val Ala Ala
    50                  55                  60

Ser Gly Lys Val Leu Val Pro Gly Thr Gln Ser Asp Ser Ser Ser Ser
65                  70                  75                  80

Ser Thr Asp Gln Phe Glu Phe Thr Glu Thr Ser Pro Glu Asn Ser Pro
            85                  90                  95
```

-continued

```
Ala Ser Thr Asp Val Asp Ser Ser Thr Met Glu His Ala Ser Gln Ile
         100                 105                 110

Lys Thr Glu Asn Asp Asp Val Glu Pro Ser Ser Asp Leu Thr Gly Ser
         115                 120                 125

Val Glu Glu Leu Asp Phe Ala Ser Ser Leu Gln Leu Gln Glu Gly Gly
     130                 135                 140

Lys Leu Glu Glu Ser Lys Thr Leu Asn Thr Ser Glu Glu Thr Ile Ile
145                 150                 155                 160

Asp Glu Ser Asp Arg Ile Arg Glu Arg Gly Ile Pro Pro Pro Gly Leu
                 165                 170                 175

Gly Gln Lys Ile Tyr Glu Ile Asp Pro Leu Leu Thr Asn Tyr Arg Gln
             180                 185                 190

His Leu Asp Tyr Arg Tyr Ser Gln Tyr Lys Lys Leu Arg Glu Ala Ile
         195                 200                 205

Asp Lys Tyr Glu Gly Gly Leu Glu Ala Phe Ser Arg Gly Tyr Glu Lys
     210                 215                 220

Met Gly Phe Thr Arg Ser Ala Thr Gly Ile Thr Tyr Arg Glu Trp Ala
225                 230                 235                 240

Leu Gly Ala Gln Ser Ala Ala Leu Ile Gly Asp Phe Asn Asn Trp Asp
                 245                 250                 255

Ala Asn Ala Asp Ile Met Thr Arg Asn Glu Phe Gly Val Trp Glu Ile
             260                 265                 270

Phe Leu Pro Asn Asn Val Asp Gly Ser Pro Ala Ile Pro His Gly Ser
         275                 280                 285

Arg Val Lys Ile Arg Met Asp Thr Pro Ser Gly Val Lys Asp Ser Ile
     290                 295                 300

Pro Ala Trp Ile Asn Tyr Ser Leu Gln Leu Pro Asp Glu Ile Pro Tyr
305                 310                 315                 320

Asn Gly Ile His Tyr Asp Pro Pro Glu Glu Glu Arg Tyr Ile Phe Gln
                 325                 330                 335

His Pro Arg Pro Lys Lys Pro Lys Ser Leu Arg Ile Tyr Glu Ser His
             340                 345                 350

Ile Gly Met Ser Ser Pro Glu Pro Lys Ile Asn Ser Tyr Val Asn Phe
         355                 360                 365

Arg Asp Glu Val Leu Pro Arg Ile Lys Lys Leu Gly Tyr Asn Ala Leu
     370                 375                 380

Gln Ile Met Ala Ile Gln Glu His Ser Tyr Tyr Ala Ser Phe Gly Tyr
385                 390                 395                 400

His Val Thr Asn Phe Phe Ala Pro Ser Ser Arg Phe Gly Thr Pro Asp
                 405                 410                 415

Asp Leu Lys Ser Leu Ile Asp Lys Ala His Glu Leu Gly Ile Val Val
             420                 425                 430

Leu Met Asp Ile Val His Ser His Ala Ser Asn Asn Thr Leu Asp Gly
         435                 440                 445

Leu Asn Met Phe Asp Cys Thr Asp Ser Cys Tyr Phe His Ser Gly Ala
     450                 455                 460

Arg Gly Tyr His Trp Met Trp Asp Ser Arg Leu Phe Asn Tyr Gly Asn
465                 470                 475                 480

Trp Glu Val Leu Arg Tyr Leu Leu Ser Asn Ala Arg Trp Trp Leu Asp
                 485                 490                 495

Ala Phe Lys Phe Asp Gly Phe Arg Phe Asp Gly Val Thr Ser Met Met
             500                 505                 510

Tyr Ile His His Gly Leu Ser Val Gly Phe Thr Gly Asn Tyr Glu Glu
```

-continued

```
            515                 520                 525
Tyr Phe Gly Leu Ala Thr Asp Val Asp Ala Val Val Tyr Leu Met Leu
        530                 535                 540

Val Asn Asp Leu Ile His Gly Leu Phe Pro Asp Ala Ile Thr Ile Gly
545                 550                 555                 560

Glu Asp Val Ser Gly Met Pro Thr Phe Cys Ile Pro Val Gln Glu Gly
                565                 570                 575

Gly Val Gly Phe Asp Tyr Arg Leu His Met Ala Ile Ala Asp Lys Arg
                580                 585                 590

Ile Glu Leu Leu Lys Lys Arg Asp Glu Asp Trp Arg Val Gly Asp Ile
                595                 600                 605

Val His Thr Leu Thr Asn Arg Arg Trp Ser Glu Lys Cys Val Ser Tyr
610                 615                 620

Ala Glu Ser His Asp Gln Ala Leu Val Gly Asp Lys Thr Ile Ala Phe
625                 630                 635                 640

Trp Leu Met Asp Lys Asp Met Tyr Asp Phe Met Ala Leu Asp Arg Pro
                645                 650                 655

Ser Thr Ser Leu Ile Asp Arg Gly Ile Ala Leu His Lys Met Ile Arg
                660                 665                 670

Leu Val Thr Met Gly Leu Gly Gly Glu Gly Tyr Leu Asn Phe Met Gly
                675                 680                 685

Asn Glu Phe Gly His Pro Glu Trp Ile Asp Phe Pro Arg Ala Glu Gln
690                 695                 700

His Leu Ser Asp Gly Ser Val Ile Pro Gly Asn Gln Phe Ser Tyr Asp
705                 710                 715                 720

Lys Cys Arg Arg Arg Phe Asp Leu Gly Asp Ala Glu Tyr Leu Arg Tyr
                725                 730                 735

Arg Gly Leu Gln Glu Phe Asp Arg Pro Met Gln Tyr Leu Glu Asp Lys
                740                 745                 750

Tyr Glu Phe Met Thr Ser Glu His Gln Phe Ile Ser Arg Lys Asp Glu
                755                 760                 765

Gly Asp Arg Met Ile Val Phe Glu Lys Gly Asn Leu Val Phe Val Phe
770                 775                 780

Asn Phe His Trp Thr Lys Ser Tyr Ser Asp Tyr Arg Ile Ala Cys Leu
785                 790                 795                 800

Lys Pro Gly Lys Tyr Lys Val Ala Leu Asp Ser Asp Pro Leu Phe
                805                 810                 815

Gly Gly Phe Gly Arg Ile Asp His Asn Ala Glu Tyr Phe Thr Phe Glu
                820                 825                 830

Gly Trp Tyr Asp Asp Arg Pro Arg Ser Ile Met Val Tyr Ala Pro Cys
                835                 840                 845

Lys Thr Ala Val Val Tyr Ala Leu Val Asp Lys Glu Glu Glu Glu
850                 855                 860

Glu Glu Glu Glu Glu Val Ala Ala Val Glu Val Val Val Glu
865                 870                 875                 880

Glu Glu
```

(2) INFORMATION FOR SEQ ID NO: 16:

(i) SEQUENCE CHARACTERISTICS:
        (A) LENGTH: 2576 base pairs
        (B) TYPE: nucleic acid
        (C) STRANDEDNESS: single
        (D) TOPOLOGY: linear (xi) SEQUENCE DESCRIPTION: SEQ ID NO: 16:

```
TCATTAAAGA GGAGAAATTA ACTATGAGAG GATCTCACCA TCACCATCAC CATGGGATCT        60

TGGCTGAAAA GTCTTCTTAC AATTCCGAAT TCCGACCTTC TACAGTTGCA GCATCGGGGA       120

AAGTCCTTGT GCCTGGAACC CAGAGTGATA GCTCCTCATC CTCAACAAAC CAATTTGAGT       180

TCACTGAGAC ATCTCCAGAA AATTCCCCAG CATCAACTGA TGTAGATAGT TCAACAATGG       240

AACACGCTAG CCAGATTAAA ACTGAGAACG ATGACGTTGA GCCGTCAAGT GATCTTACAG       300

GAAGTGTTGA AGAGCTGGAT TTTGCTTCAT CACTACAACT ACAAGAAGGT GGTAAACTGG       360

AGGAGTCTAA AACATTAAAT ACTTCTGAAG AGACAATTAT TGATGAATCT GATAGGATCA       420

GAGAGAGGGG CATCCCTCCA CCTGGACTTG GTCAGAAGAT TTATGAAATA GACCCCCTTT       480

TGACAAACTA TCGTCAACAC CTTGATTACA GGTATTCACA GTACAAGAAA CTGAGGGAGG       540

CAATTGACAA GTATGAGGGT GGTTTGGAAG CTTTTTCTCG TGGTTATGAA AAAATGGGTT       600

TCACTCGTAG TGCTACAGGT ATCACTTACC GTGAGTGGGC TCCTGGTGCC CAGTCAGCTG       660

CCCTCATTGG AGATTTCAAC AATTGGGACG CAAATGCTGA CATTATGACT CGGAATGAAT       720

TTGGTGTCTG GGAGATTTTT CTGCCAAATA ATGTGGATGG TTCTCCTGCA ATTCCTCATG       780

GGTCCAGAGT GAAGATACGT ATGGACACTC CATCAGGTGT TAAGGATTCC ATTCCTGCTT       840

GGATCAACTA CTCTACAGCT TCCTGATGAA ATTCCATATA ATGGAATATA TTATGATCCA       900

CCCGAAGAGG AGAGGTATAT CTTCCAACAC CCACGGCCAA AGAAACCAAA GTCGCTGAGA       960

ATATATGAAT CTCATATTGG AATGAGTAGT CCGGAGCCTA AAATTAACTC ATACGTGAAT      1020

TTTAGAGATG AAGTTCTTCC TCGCATAAAA AAGCTTGGGT ACAATGCGCT GCAAATTATG      1080

GCTATTCAAG AGCATTCTTA TTATGCTAGT TTTGGTTATC ATGTCACAAA TTTTTTTGCA      1140

CCAAGCAGCC GTTTTGGAAC GCCCGACGAC CTTAAGTCTT TGATTGATAA AGCTCATGAG      1200

CTAGGAATTG TTGTTCTCAT GGACATTGTT CACAGCCATG CATCAAATAA TACTTTAGAT      1260

GGACTGAACA TGTTTGACGG CACCGATAGT TGTTACTTTC ACTCTGGAGC TCGTGGTTAT      1320

CATTGGATGT GGGATTCCCG CCTTTTTAAC TATGGAAACT GGGAGGTACT TAGGTATCTT      1380

CTCTCAAATG CGAGATGGTG GTTGGATGAG TTCAAATTTG ATGGATTTAG ATTTGATGGT      1440

GTGACATCAA TGATGTATAC TCACCACGGA TTATCGGTGG GATTCACTGG GAACTACGAG      1500

GAATACTTTG GACTCGCAAC TGATGTGGAT GCTGTTGTGT ATCTGATGCT GGTCAACGAT      1560

CTTATTCATG GGCTTTTCCC AGATGCAATT ACCATTGGTG AAGATGTTAG CGGAATGCCG      1620

ACATTTGTA TTCCCGTTCA AGATGGGGGT GTTGGCTTTG ACTATCGGCT GCATATGGCA       1680

ATTGCTGATA AATGGATTGA GTTGCTCAAG AAACGGGATG AGGATTGGAG AGTGGGTGAT      1740

ATTGTTCATA CACTGACAAA TAGAAGATGG TCGGAAAAGT GTGTTTCATA CGCTGAAAGT      1800

CATGATCAAG CTCTAGTCGG TGATAAAACT ATAGCATTCT GGCTGATGGA CAAGGATATG      1860

TATGATTTTA TGGCTCTGGA TAGACCGCCA ACATCATTAA TAGATCGTGG GATAGCATTG      1920

CACAAGATGA TTAGGCTTGT AACTATGGGA TTAGGAGGAG AAGGGTACCT AAATTTCATG      1980

GGAAATGAAT TCGGCCACCC TGAGTGGATT GATTTCCCTA GGGCTGAACA ACACCTCTCT      2040

GATGACTCAG TAATTCCCGG AAACCAATTC AGTTATGATA AATGCAGACG GAGATTTGAC      2100

CTGGGAGATG CAGAATATTT AAGATACCGT GGGTTGCAAG AATTTGACCG GGCTATGCAG      2160

TATCTTGAAG ATAAATATGA GTTTATGACT TCAGAACACC AGTTCATATC ACGAAAGGAT      2220

GAAGGAGATA GGATGATTGT ATTTGAAAAA GGAAACCTAG TTTTTGTCTT TAATTTTCAC      2280

TGGACAAAAA GCTATTCAGA CTATCGCATA GGCTGCCTGA AGCCTGGAAA ATACAAGGTT      2340
```

```
GCCTTGGACT CAGATGATCC ACTTTTTGGT GGCTTCGGGA GAATTGATCA TAATGCCGAA      2400

TATTTCACCT TTGAAGGATG GTATGATGAT CGTCCTCGTT CAATTATGGT GTATGCACCT      2460

TGTAGAACAG CAGTGGTCTA TGCACTAGTA GACAAAGAAG AAGAAGAAGA AGAAGAAGAA      2520

GAAGAAGTAG CAGTAGTAGA AGAAGTAGTA GTAGAAGAAG AATGAACGAA CTTGTG          2576

(2) INFORMATION FOR SEQ ID NO: 17:

(i) SEQUENCE CHARACTERISTICS:
         (A) LENGTH: 2529 base pairs
         (B) TYPE: nucleic acid
         (C) STRANDEDNESS: single
         (D) TOPOLOGY: linear (xi) SEQUENCE DESCRIPTION: SEQ ID NO: 17:

GGATGCTAAT GTTTCTGTAT TCTTGAAAAA GCACTCTCTT TCACGGAAGA TCTTGGCTGA       60

AAAGTCTTCT TACAATTCCG AATCCCGACC TTCTACAGTT GCAGCATCGG GGAAAGTCCT      120

TGTGCCTGGA AYCCAGAGTG ATAGCTCCTC ATCCTCAACA GACCAATTTG AGTTCACTGA      180

GACATCTCCA GAAAATTCCC CAGCATCAAC TGATGTAGAT AGTTCAACAA TGGAACACGC      240

TAGCCAGATT AAAACTGAGA ACGATGACGT TGAGCCGTCA AGTGATCTTA CAGGAAGTGT      300

TGAAGAGCTG GATTTTGCTT CATCACTACA ACTACAAGAA GGTGGTAAAC TGGAGGAGTC      360

TAAAACATTA AATACTTCTG AAGAGACAAT TATTGATGAA TCTGATAGGA TCAGAGAGAG      420

GGGCATCCCT CCACCTGGAC TTGGTCAGAA GATTATGAAA ATAGACCCCC TTTTGACAAA      480

CTATCGTCAA CACCTTGATT ACAGGTATTC ACAGTACAAG AAACTGAGGG AGGCAATTGA      540

CAAGTATGAG GGTGGTTTGG AAGCTTTTTC TCGTGGTTAT GAAAAAATGG GTTTCACTCG      600

TAGTGCTACA GGTATCACTT ACCGTGAGTG GGCTCCTGGT GCCCAGTCAG CTGCCCTCAT      660

TGGAGATTTC AACAATTGGG ACGCAAATGC TGACATTATG ACTCGGAATG AATTTGGTGT      720

CTGGGAGATT TTTCTGCCAA ATAATGTGGA TGGTTCTCCT GCAATTCCTC ATGGGTCCAG      780

AGTGAAGATA CGYATGGACA CTCCATCAGG TGTTAAGGAT TCCATTCCTG CTTGGATCAA      840

CTACTCTTTA CAGCTTCCTG ATGAAATTCC ATATAATGGA ATATATTATG ATCCACCCGA      900

AGAGGAGAGG TATRTCTTCC AACACCCACG GCCAAAGAAA CCAAAGTCGC TGAGAATATA      960

TGAATCTCAT ATTGGAATGA GTAGTCCGGA GCCTAAAATT AACTCATACG TGAATTTTAG     1020

AGATGAAGTT CTTCCTCGCA TAAAAAASCT TGGGTACAAT GCGGTGCAAA TTATGGCTAT     1080

TCAAGAGCAT TCTTATTATG CTAGTTTTGG TTATCATGTC ACAAATTTTT TTGCACCAAG     1140

CAGCCGTTTT GGAACGCCCG ACGACCTTAA GTCTTTGATT GATAAAGCTC ATGAGCTAGG     1200

AATTGTTGTT CTCATGGACA TTGTTCACAG CCATGCATCA AATAATACTT TAGATGGACT     1260

GAACATGTTT GACGGCACAG ATAGTTGTTA CTTTCACTCT GGAGCTCGTG GTTATCATTG     1320

GATGTGGGAT TCCCGCCTCT TTAACTATGG AAACTGGGAG GTACTTAGGT ATCTTCTCTC     1380

AAATGCGAGA TGGTGGTTGG ATGAGTTCAA ATTTGATGGA TTTAGATTTG ATGGTGTGAC     1440

ATCAATGATG TATACTCACC ACGGATTATC GGTGGGATTC ACTGGGAACT ACGAGGAATA     1500

CTTTGGACTC GCAACTGATG TGGATGCTGT TGTGTATCTG ATGCTGGTCA ACGATCTTAT     1560

TCACGGGCTT TTCCCAGATG CAATTACCAT TGGTGAAGAT GTTAGCGGAA TGCCGACATT     1620

TTGTATTCCC GTTCAAGATG GGGGTGTTGG CTTTGACTAT CGGCTGCATA TGGCAATTGC     1680

TGATAAATGG ATTGAGTTGC TCAAGAAACG GGATGAGGAT TGGAGAGTGG GTGATATTGT     1740

TCATACACTG ACAAATAGAA GATGGTCGGA AAAGTGTGTT TCATMCGCTG AAAGTCATGA     1800
```

| | |
|---|---|
| TCAAGCTCTA GTCGGTGATA AAACTATAGC ATYCTGGCTG ATGGACAAGG ATATGTATGA | 1860 |
| TTTTATGGCT CTGGATAGAC CGYCAACAYC ATTAATAGAT CGTGGGATAG CATTGCACAA | 1920 |
| GATGATTAGG CTTGTAACTA TGGGATTAGG AGGAGAAGGG TACCTAAATT TCATGGGAAA | 1980 |
| TGAATTCGGC CACCCTGAGT GGATTGATTT CCCTAGGGCT GARCAACACC TCTCTGATGG | 2040 |
| CTCAGTAATT CCCGGAAACC AATTCAGTTA TGATAAATGC AGACGGAGAT TTGACCTGGG | 2100 |
| AGATGCAGAA TATTTAAGAT ACCATGGGTT GCAAGAATTT GACCGGGCTA TGCAGTATCT | 2160 |
| TGAAGATAAA TATGAGTTTA TGACTTCAGA ACACCAGTTC ATATCACGAA AGGATGAAGG | 2220 |
| AGATAGGATG ATTGTATTTG AAARAGGAAA CCTAGTTTTT GTCTTTAATT TTCACTGGAC | 2280 |
| AAATAGCTAT TCAGACTATC GCATAGGCTG CCTGAAGCCT GGAAAATACA AGGTTGGCTT | 2340 |
| GGACTCAGAT GATCCACTTT TTGGTGGCTT CGGGAGAATT GATCATAATG CCGAATATTT | 2400 |
| CACCTCTGAA GGATCGTATG ATGATCGTCC TCGTTCAATT ATGGTGTATG CACCTAGTAG | 2460 |
| AACAGCAGTG GTCTATGCAC TAGTAGACAA ANTAGAAGNA GAAGAAGAAG AAGAANCCGN | 2520 |
| NGAAGAATT | 2529 |

(2) INFORMATION FOR SEQ ID NO: 18:

(i) SEQUENCE CHARACTERISTICS:
        (A) LENGTH: 3231 base pairs
        (B) TYPE: nucleic acid
        (C) STRANDEDNESS: single
        (D) TOPOLOGY: linear (xi) SEQUENCE DESCRIPTION: SEQ ID NO: 18:

| | |
|---|---|
| GATTTAATAC GACTCACTAT AGGGATTTTT TTTTTTTTTT TTTTAAAAAC CTCCTCCACT | 60 |
| CAGTCTTGGG ATCTCTCTCT CTCTTCACGC TTCTCTTGGG GCCTTGAACT CAGCAATTTG | 120 |
| ACACTCAGTT AGTTACACTC CTATCACTCA TCAGATCTCT ATTTTTTCTC TTAATTCCAA | 180 |
| CCAAGGAATG AATTAAAAGA TTAGATTTGA AGGAGAGAAG AAGAAAGATG GTGTATACAC | 240 |
| TCTCTGGAGT TCGTTTTCCT ACTGTTCCAT CAGTGTACAA ATCTAATGGA TTCAGCAGTA | 300 |
| ATGGTGATCG GAGGAATGCT AATGTTTCTG TATTCTTGAA AAAGCACTCT CTTTCACGGA | 360 |
| AGATCTTGGC TGAAAAGTCT TCTTACGATT CCGAATCCCG ACCTTCTACA GTTGCAGCAT | 420 |
| CGGGGAAAGT CCTTGTACCT GGAATCCAGA GTGATAGCTC CTCATCCTCA ACAGACCAAT | 480 |
| TTGAGTTCAC TGAGACAGCT CCAGAAAATT CCCCAGCATC AACTGATGTG ATAGTTCAA | 540 |
| CAATGGAACA CGCTAGCCAG ATTAAAACTG AGAACGATGA CGTTGAGCCG TCAAGTGATC | 600 |
| TTACAGGAAG TGTTGAAGAG TTGGATTTTG CTTCATCACT ACAACTACAA GAAGGTGGTA | 660 |
| AACTGGAGGA GTCTAAAACA TTAAATACTT CTGAAGAGAC AATTATTGAT GAATCTGATA | 720 |
| GGATCAGAGA GAGGGGCATC CCTCCACCTG GACTTGGTCA GAAGATTTAT GAAATAGACC | 780 |
| CCCTTTTGAC AAACTATCGT CAACACCTTG ATTACAGGTA TTCACAGTAC AAGAAAATGA | 840 |
| GGGAGGCAAT TGACAAGTAT GAGGGTGGTT TGGAAGCTTT TTCTCGTGGT TATGAAAAAA | 900 |
| TGGGTTTCAC TCGTAGTGCT ACAGGTATCA CTTACCGTGA GTGGGCTCCT GGTGCCCAGT | 960 |
| CAGCTGCTCT CATTGGAGAT TTCAACAATT GGGACGCAAA TGCTGACATT ATGACTCGGA | 1020 |
| ATGAATTTGG TGTCTGGGAG ATTTTTCTGC CAAATAATGT GGATGGTTCT CCTGCAATTC | 1080 |
| CTCATGGGTC CAGAGTGAAG ATACGCATGG ACACTTCATC AGGTGTTAAG GATTCCATTC | 1140 |
| CTGCTTGGAT CAACTACTCT TTACAGCTTC CTGATGAAAT TCCATATAAT GGAATATATT | 1200 |
| ATGATCCACC CGAAGAGGAG AGGTATGTCT TCCAACACCC ACGGCCAAAG AAACCAAAGT | 1260 |

```
CGCTGAGAAT ATATGAATCT CATATTGGAA TGAGTAGTCC GGAGCCTAAA ATTAACTCAT      1320

ACGTGAATTT TAGAGATGAA GTTCTTCCTC GCATAAAAAA CCTTGGGTAC AATGCGGTGC      1380

AAATTATGGC TATTCAAGAG CATTCTTATT ATGCTAGTTT TGGTTATCAT GTCACAAATT      1440

TTTTTGCACC AAGCAGCCGT TTTGGAACGC CCGACGACCT TAAGTCTTTG ATTGATAAAG      1500

CTCATGAGCT AGGAATTGTT GTTCTCATGG ACATTGTTCA CAGCCATGCA TCAAATAATA      1560

CTTTAGATGG ACTGAACATG TTTGACGGCA CAGATAGTTG TTACTTTCAC TCTGGAGCTC      1620

GTGGTTATCA TTGGATGTGG GATTCCCGCC TCTTTAACTA TGGAAACTGG GAGGTACTTA      1680

GGTATCTTCT CTCAAATGCG AGATGGTGGT TGGATGAGTG CAAATTTGRT GGATTTAGAT      1740

TTGATGGTGT GACATCAATG ATGTATACTC ACCACGGATT ATCGGTGGGA TTCACTGGGA      1800

ACTACGAGGA ATACTTTGGA CTCGCAACTG ATGTRGATGC TGCCGTGTAT CTGATGCTGG      1860

CCAACGATCT TATTCATGGG CTTTTCCCAG ATGCAATTAC CATTGGTGAA GATGTTAGCG      1920

GAATGCCGAC ATTTTGTATT CCCGTTCAAG ATGGGGTGT TGGCTTTGAC TATCGGCTGC       1980

ATATGGCAAT TGCTGATAAA TGGATTGAGT TGCTCAAGAA ACGGGATGAG GATTGGAGAG      2040

TGGGTGATAT TGTTCATACA CTGACAAATA GAAGATGGTC GGAAAAGTGT GTTTCATACG      2100

CTGAAAGTCA TGATCAAGCT CTAGTCGGTG ATAAAACTAT AGCATTCTGG CTGATGGACA      2160

AGGATATGTA TGATTTTATG GCTTTGGATA GACCGTCAAC ATCATTAATA GATCGTGGGA      2220

TAGCATTGCA CAAGATGATT AGGCTTGTAA CTATGGGATT AGGAGGAGAA GGGTACCTAA      2280

ATTTCATGGG AAATGAATTC GGCCACCCTG AGTGGATTGA TTTCCCTAGG GCTGAACAAC      2340

ACCTCTCTGA TGGCTCAGTA ATTCCCGGAA ACCAATTCAG TTATGATAAA TGCAGACGGA      2400

GATTTGACCT GGGAGATGCA GAATATTTAA GATACCGTGG GTTGCAAGAA TTTGACCGGG      2460

CTATGCAGTA TCTTGAAGAT AAATATGAGT TTATGACTTC AGAACACCAG TTCATATCAC      2520

GAAAGGATGA AGGAGATAGG ATGATTGTAT TTGAAAAAGG AAACCTAGTT TTTGTCTTTA      2580

ATTTTCACTG GACAAAAAGC TATTCAGACT ATCGCATAGG CTGGCTGAAG CCTGGAAAAT      2640

ACAAGGTTGC CTTGGACTCA GATGATCCAC TTTTTGGTGG CTTCGGGAGA ATTGATCATA      2700

ATGCCGAATG TTTCACCTTT GAAGGATGGT ATGATGATCG TCCTCGTTCA ATTATGGTGT      2760

ATGCACCTAG TAGAACAGCA GTGGTCTATG CACTAGTAGA CAAAGAAGAA GAAGAAGAAG      2820

AAGTAGCAGT AGTAGAAGAA GTAGTAGTAG AAGAAGAATG AACGAACTTG TGATCGCGTT      2880

GAAAGATTTG AACGCTACAT AGAGCTTCTT GACGTATCTG GCAATATTGC ATCAGTCTTG      2940

GCGGAATTTC ATGTGACAAA AGGTTTGCAA TTCTTTCCAC TATTAGTAGT GCAACGATAT      3000

ACGCAGAGAT GAAGTGCTGA ACAAACATAT GTAAAATCGA TGAATTTATG TCGAATGCTG      3060

GGACGGGCTT CAGCAGGTTT TGCTTAGTGA GTTCTGTAAA TTGTCATCTC TTTANATGTA      3120

CAGCCCACTA GAAATCAATT ATGTGAGACC TAAAAAACAA TAACCATAAA ATGGAAATAG      3180

TGCTGATCTA ATGATGTTTT AANCCNNNNA AAAAAAAAA AAAAACTCGA G               3231
```

(2) INFORMATION FOR SEQ ID NO: 19:

(i) SEQUENCE CHARACTERISTICS:
        (A) LENGTH: 2578 base pairs
        (B) TYPE: nucleic acid
        (C) STRANDEDNESS: single
        (D) TOPOLOGY: linear (xi) SEQUENCE DESCRIPTION: SEQ ID NO: 19:

```
TCATTAAAGA GGAGAAATTA ACTATGAGAG GATCTCACCA TCACCATCAC CATGGGATCT       60
```

```
TGGCTGAAAA GTCTTCTTAC AATTCCGAAT TCCGACCTTC TACAGTTGCA GCATCGGGGA    120

AAGTCCTTGT GCCTGGAACC CAGAGTGATA GCTCCTCATC CTCAACAAAC CAATTTGAGT    180

TCACTGAGAC ATCTCCAGAA AATTCCCCAG CATCAACTGA TGTAGATAGT TCAACAATGG    240

AACACGCTAG CCAGATTAAA ACTGAGAACG ATGACGTTGA GCCGTCAAGT GATCTTACAG    300

GAAGTGTTGA AGAGCTGGAT TTTGCTTCAT CACTACAACT ACAAGAAGGT GGTAAACTGG    360

AGGAGTCTAA AACATTAAAT ACTTCTGAAG AGACAATTAT TGATGAATCT GATAGGATCA    420

GAGAGAGGGG CATCCCTCCA CCTGGACTTG GTCAGAAGAT TTATGAAATA GACCCCCTTT    480

TGACAAACTA TCGTCAACAC CTTGATTACA GGTATTCACA GTACAAGAAA CTGAGGGAGG    540

CAATTGACAA GTATGAGGGT GGTTTGGAAG CTTTTTCTCG TGGTTATGAA AAAATGGGTT    600

TCACTCGTAG TGCTACAGGT ATCACTTACC GTGAGTGGGC TCCTGGTGCC CAGTCAGCTG    660

CCCTCATTGG AGATTTCAAC AATTGGGACG CAAATGCTGA CATTATGACT CGGAATGAAT    720

TTGGTGTCTG GGAGATTTTT CTGCCAAATA ATGTGGATGG TTCTCCTGCA ATTCCTCATG    780

GGTCCAGAGT GAAGATACGT ATGGACACTC CATCAGGTGT TAAGGATTCC ATTCCTGCTT    840

GGATCAACTA CTCTTCACAG CTTCCTGATG AAATTCCATA TAATGGAATA TATTATGATC    900

CACCCGAAGA GGAGAGGTAT ATCTTCCAAC ACCCACGGCC AAAGAAACCA AAGTCGCTGA    960

GAATATATGA ATCTCATATT GGAATGAGTA GTCCGGAGCC TAAAATTAAC TCATACGTGA   1020

ATTTTAGAGA TGAAGTTCTT CCTCGCATAA AAAAGCTTGG GTACAATGCG GTGCAAATTA   1080

TGGCTATTCA AGAGCATTCT TATTATGCTA GTTTTGGTTA TCATGTCACA AATTTTTTTG   1140

CACCAAGCAG CCGTTTTGGA ACGCCCGACG ACCTTAAGTC TTTGATTGAT AAAGCTCATG   1200

AGCTAGGAAT TGTTGTTCTC ATGGACATTG TTCACAGCCA TGCATCAAAT AATACTTTAG   1260

ATGGACTGAA CATGTTTGAC GGCACCGATA GTTGTTACTT TCACTCTGGA GCTCGTGGTT   1320

ATCATTGGAT GTGGGATTCC CGCCTTTTTA ACTATGGAAA CTGGGAGGTA CTTAGGTATC   1380

TTCTCTCAAA TGCGAGATGG TGGTTGGATG AGTTCAAATT TGATGGATTT AGATTTGATG   1440

GTGTGACATC AATGATGTAT ACTCACCACG GATTATCGGT GGGATTCACT GGAACTACG    1500

AGGAATACTT TGGACTCGCA ACTGATGTGG ATGCTGTTGT GTATCTGATG CTGGTCAACG   1560

ATCTTATTCA TGGGCTTTTC CCAGATGCAA TTACCATTGG TGAAGATGTT AGCGGAATGC   1620

CGACATTTTG TATTCCCGTT CAAGATGGGG GTGTTGGCTT TGACTATCGG CTGCATATGG   1680

CAATTGCTGA TAAATGGATT GAGTTGCTCA AGAAACGGGA TGAGGATTGG AGAGTGGGTG   1740

ATATTGTTCA TACACTGACA AATAGAAGAT GGTCGGAAAA GTGTGTTTCA TACGCTGAAA   1800

GTCATGATCA AGCTCTAGTC GGTGATAAAA CTATAGCATT CTGGCTGATG GACAAGGATA   1860

TGTATGATTT TATGGCTCTG GATAGACCGC CAACATCATT AATAGATCGT GGGATAGCAT   1920

TGCACAAGAT GATTAGGCTT GTAACTATGG GATTAGGAGG AGAAGGGTAC CTAAATTTCA   1980

TGGGAAATGA ATTCGGCCAC CCTGAGTGGA TTGATTTCCC TAGGGCTGAA CAACACCTCT   2040

CTGATGACTC AGTAATTCCC GGAAACCAAT TCAGTTATGA TAAATGCAGA CGGAGATTTG   2100

ACCTGGGAGA TGCAGAATAT TTAAGATACC GTGGGTTGCA AGAATTTGAC CGGGCTATGC   2160

AGTATCTTGA AGATAAATAT GAGTTTATGA CTTCAGAACA CCAGTTCATA TCACGAAAGG   2220

ATGAAGGAGA TAGGATGATT GTATTTGAAA AAGGAAACCT AGTTTTTGTC TTTAATTTTC   2280

ACTGGACAAA AAGCTATTCA GACTATCGCA TAGGCTGCCT GAAGCCTGGA AAATACAAGG   2340

TTGCCTTGGA CTCAGATGAT CCACTTTTTG GTGGCTTCGG GAGAATTGAT CATAATGCCG   2400
```

-continued

```
AATATTTCAC CTTTGAAGGA TGGTATGATG ATCGTCCTCG TTCAATTATG GTGTATGCAC    2460

CTTGTAGAAC AGCAGTGGTC TATGCACTAG TAGACAAAGA AGAAGAAGAA GAAGAAGAAG    2520

AAGAAGAAGT AGCAGTAGTA GAAGAAGTAG TAGTAGAAGA AGAATGAACG AACTTGTG     2578

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 20:

AATTTYATGG GNAAYGARTT YGG                                              23
```